（12） United States Patent
Jansen et al.

(10) Patent No.: US 11,312,950 B2
(45) Date of Patent: Apr. 26, 2022

(54) 3D SYNTHETIC TISSUE HYDROGELS

(71) Applicant: University of Massachusetts, Boston, MA (US)

(72) Inventors: Lauren Jansen, East Boston, MA (US); Shelly Peyton, Amherst, MA (US)

(73) Assignee: University of Massachusetts, Boston, MA (US)

( * ) Notice: Subject to any disclaimer, the term of this patent is extended or adjusted under 35 U.S.C. 154(b) by 543 days.

(21) Appl. No.: 15/895,710

(22) Filed: Feb. 13, 2018

(65) Prior Publication Data

US 2018/0346902 A1 Dec. 6, 2018

Related U.S. Application Data

(60) Provisional application No. 62/459,815, filed on Feb. 16, 2017.

(51) Int. Cl.
*C12N 11/04* (2006.01)
*C12N 11/12* (2006.01)

(52) U.S. Cl.
CPC .............. *C12N 11/04* (2013.01); *C12N 11/12* (2013.01); *C12N 2513/00* (2013.01); *C12N 2533/30* (2013.01); *C12N 2533/74* (2013.01); *C12N 2533/76* (2013.01); *C12N 2533/78* (2013.01); *C12N 2533/80* (2013.01); *C12N 2533/90* (2013.01)

(58) Field of Classification Search
None
See application file for complete search history.

(56) References Cited

U.S. PATENT DOCUMENTS 9,061,050 B2 * 6/2015 Gobin .................. A61K 9/0048
2018/0318360 A1 * 11/2018 Shikanov ............. A61K 9/0024

OTHER PUBLICATIONS

Lam et al. "Design of experiments methodology to optimize hydrogel for iPSC-NPC culture" Adv. Healthc. Mater. 4:534-539. (Year: 2015).*
Patterson J and Hubbell JA "Enhances proteolytic degradation of molecularly engineered PEG hydrogels in response to MMP-1 and MMP-2" Biomaterials 31:7836-7845. (Year: 2010).*
Vat K and Benoit D "Dynamic Manipulation of Hydrogels to Control Cell Behavior: A Review" Tissue Engineering: Part B 19:455-469. (Year: 2013).*

* cited by examiner

*Primary Examiner* — Sudhakar Katakam
*Assistant Examiner* — Zachary J Miknis
(74) *Attorney, Agent, or Firm* — Schwegman Lundberg & Woessner, P.A.

(57) ABSTRACT

A method to prepare synthetic hydrogels having tissue-specific properties, and a hydrogel comprising a polymer matrix comprising a plurality of peptide, are provided.

10 Claims, 60 Drawing Sheets
Specification includes a Sequence Listing.

| Fibrinogen A | RGD | Laminin G | Osteopontin |
| Fibronectin | Laminin A | Fibrinogen G | Netrin-1 |
| Collagen I, IX | Laminin B | Tenascin C | Collagen I |

| | MMP 2 | | MMP 7 | | MMP 14 |
| | MMP 3 | | MMP 13 | | MMP 1,9 |

| MMP 1,9  | Netrin-1

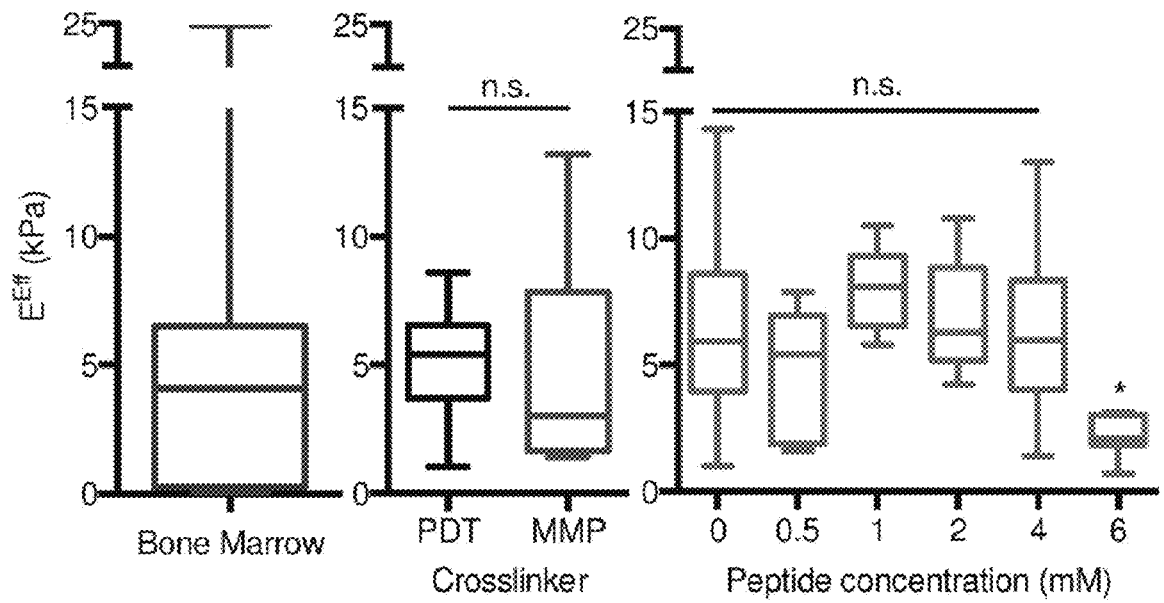
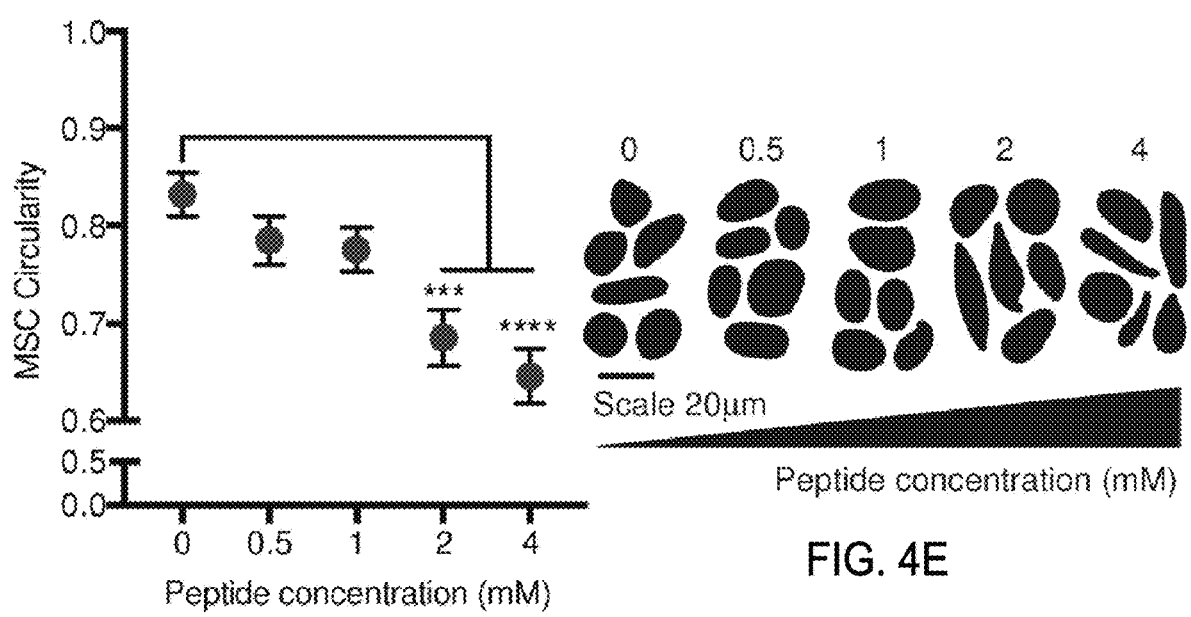

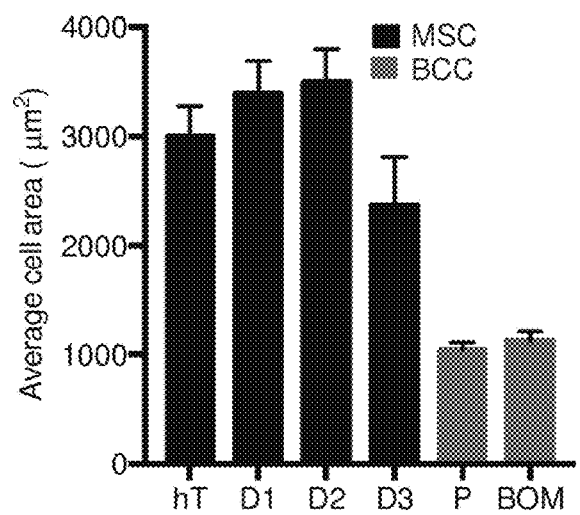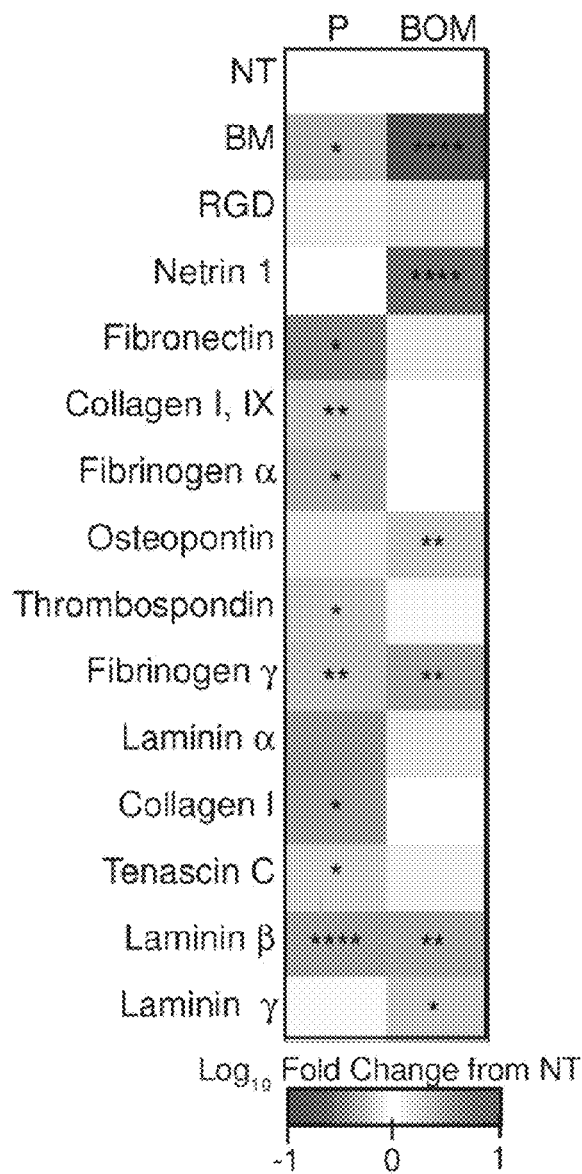
FIG. 7A
FIG. 7B

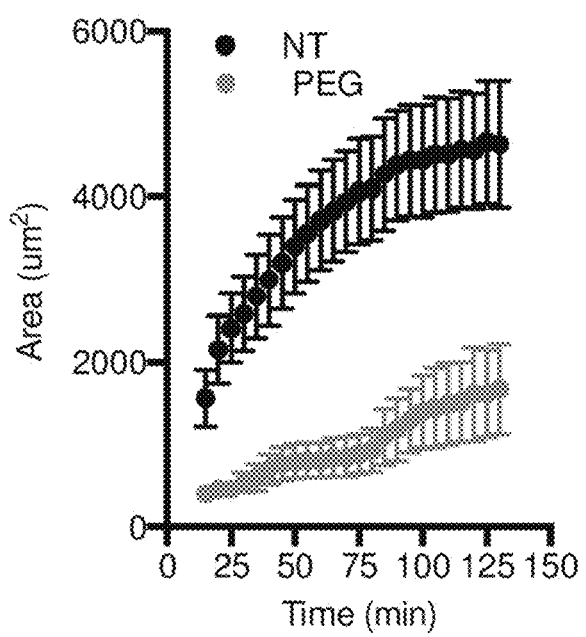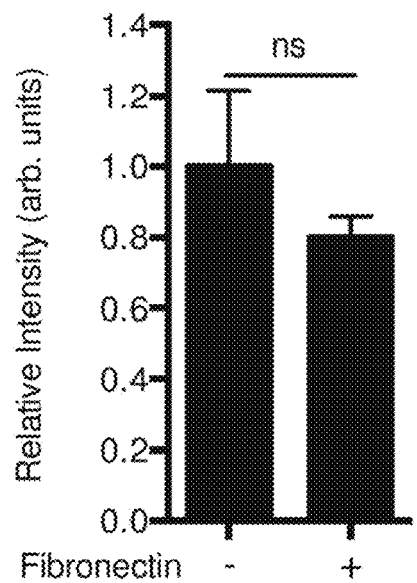
FIG. 7C
FIG. 7D
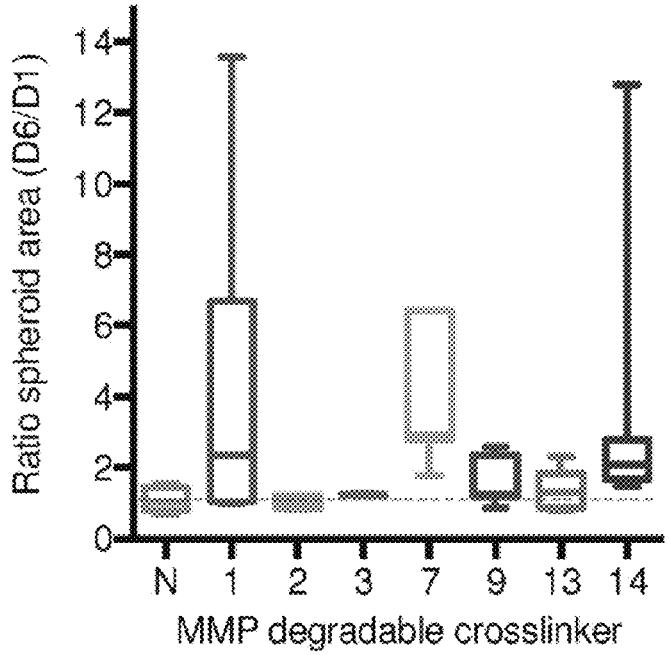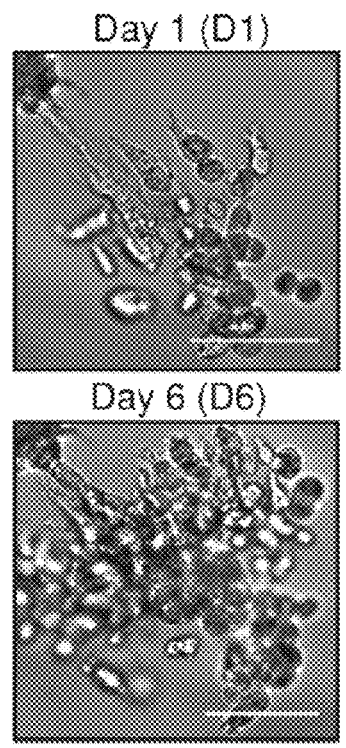
FIG. 8A
FIG. 8B

| Protein | Gene Code | Integrin Heterodimers | RNA Tissue Enhanced (*=enriched) [6] | Peptide Binding Motif |
|---|---|---|---|---|
| Collagen I | COL1A1 | $\alpha_1\beta_1$, $\alpha_2\beta_1$, $\alpha_{11}\beta_1$, $\alpha_X\beta_2$ | All | GFOGER, DGEA |
|  | COL1A2 |  | All |  |
| Collagen II | COL2A1 | $\alpha_{10}\beta_1$ | Prostate, stomach, testis |  |
| Collagen III | COL3A1 |  | Gallbladder |  |
| Collagen IV | COL4A1 |  | Placenta |  |
|  | COL4A2 |  | Placenta |  |
|  | COL4A3 | $\alpha_1\beta_1$, $\alpha_2\beta_1$ | Kidney | GFOGER, FYFDLR |
|  | COL4A4 |  | Mixed |  |
|  | COL4A5 |  | Mixed |  |
|  | COL4A6 |  | Smooth muscle |  |
| Collagen V | COL5A1 |  | Mixed |  |
|  | COL5A2 |  | Mixed |  |
|  | COL5A3 |  | Mixed |  |
| Collagen VI | COL6A1 |  | Mixed |  |
|  | COL6A2 |  | All |  |
|  | COL6A3 | $\alpha_1\beta_1$, $\alpha_2\beta_1$ | Smooth muscle |  |
|  | COL6A5 |  | Lung, skin |  |
|  | COL6A6 |  | Lung |  |
| Collagen VII | COL7A1 |  | Skin* |  |
| Collagen VIII | COL8A1 |  | Thyroid gland |  |
|  | COL8A2 |  | Mixed |  |
| Collagen IX | COL9A1 |  | Prostate |  |
|  | COL9A2 | $\alpha_1\beta_1$, $\alpha_2\beta_1$ | Mixed |  |
|  | COL9A3 |  | Salivary gland, thyroid gland |  |
| Collagen X | COL10A1 |  | Gallbladder |  |
| Collagen XI | COL11A1 |  | Placenta |  |
|  | COL11A2 |  | Mixed |  |
| Collagen XIV | COL14A1 |  | Mixed |  |
| COMP | COMP | $\alpha_5\beta_1$, $\alpha_V\beta_3$ | Gallbladder |  |
| Factor XII | F12 |  | Liver* |  |
| Factor X | F5 | $\alpha_M\beta_2$ | Liver, placenta |  |
| Fibulin | FBLN1 |  | Mixed |  |
|  | FBLN2 |  | Mixed |  |
|  | FBLN5 |  | All |  |
|  | FBLN7 |  | Mixed |  |
| Fibrillin | FBN1 |  | All |  |
|  | FBN2 | $\alpha_V\beta_3$ | Placenta* | RGD |
|  | FBN3 |  | Lung |  |
|  | FGA |  | Liver* | GPR, KRLDGS |
|  | FGB |  | Liver* | RGD |

FIG. 9A

| Protein | Gene Code | Integrin Heterodimers | RNA Tissue Enhanced (*=enriched) [6] | Peptide Binding Motif |
|---|---|---|---|---|
| Fibrinogen | FGG | $\alpha_M\beta_2, \alpha_X\beta_2, \alpha_{IIb}\beta_3, \alpha_V\beta_1$ | Liver* | YSMKKTTMKIIP FNRLTIG, GWTVFQKRLD GS |
| Fibronectin | FN1 | $\alpha_4\beta_1, \alpha_5\beta_1, \alpha_8\beta_1, \alpha_4\beta_7, \alpha_V\beta_3, \alpha_V\beta_6, \alpha_{IIb}\beta_3, \alpha_V\beta_1$ | All | RGD, PHSRN-RGD, LDV, IDA, REDV |
| Laminin α | LAMA1 LAMA2 LAMA3 LAMA4 LAMA5 | (chain composition) $\alpha_1\beta_1$ (1,2), $\alpha_2\beta_1$ (1,2), $\alpha_3\beta_1$ (2,5,10,11), $\alpha_6\beta_1$ (8,9,10,11), $\alpha_7\beta_1$ (1), $\alpha_6\beta_4$ (1,10,11), $\alpha_{10}\beta_1$ (10,11) | Testis Placenta Mixed Mixed All | IKVAV, YGYYGDALR, RGD |
| Laminin β | LAMB1 LAMB2 LAMB3 LAMB4 | | All All Mixed Skin* | YIGSR, PDSGR, RYVVLPR |
| Laminin γ | LAMC1 LAMC2 LAMC3 | | All Mixed Placenta | LRE |
| Elastin | ELN | $\alpha_V\beta_3$ | Mixed | GRKRK, VGVAPG |
| Entactin/Nidogen | NID-1 | $\alpha_3\beta_1$ | All | RGD |
| Netrin-1 | NTN1 | $\alpha_3\beta_1, \alpha_6\beta_4$ | Mixed | QWRDTWARRL RKFQQREKKG KCRKA |
| Reelin | RELN | $\alpha_3\beta_1$ | Liver | |
| Osteopontin | SPP1 | $\alpha_9\beta_1, \alpha_4\beta_1, \alpha_5\beta_1, \alpha_8\beta_1, \alpha_4\beta_7, \alpha_V\beta_1, \alpha_V\beta_6, \alpha_V\beta_3, \alpha_V\beta_5$ | Cerebral cortex, gallbladder, kidney, placenta | SVVYGLR, LDV, RGD |
| Thrombospondin | THBS1 THBS2 THBS3 THBS4 | $\alpha_2\beta_1, \alpha_4\beta_1, \alpha_3\beta_1, \alpha_V\beta_3, \alpha_{IIb}\beta_3$ | Mixed Gallbladder All Adipose tissue, heart muscle, | RGD, VTXG |
| Tenascin C | TNC | $\alpha_9\beta_1, \alpha_V\beta_6, \alpha_8\beta_1, \alpha_V\beta_3$ | Smooth muscle | AEIDGIEL, DLXXL |
| Vitronectin | VTN | $\alpha_V\beta_3, \alpha_V\beta_5, \alpha_8\beta_1, \alpha_{IIb}\beta_3$ | Liver | RGD |
| von Willebrand factor | vWF | $\alpha_V\beta_3, \alpha_{IIb}\beta_3$ | Mixed | RGD |

FIG. 9B

| Enzyme | Gene Code | ECM Protein Degradation [5] | RNA Tissue Enhanced (*=enriched) [6] | Peptide Degrading Sequences [4] |
|---|---|---|---|---|
| Collagenase-1 | MMP1 | Aggrecan<br>Collagen I<br>Collagen II<br>Collagen III<br>Collagen VII<br>Collagen VIII<br>Collagen X<br>Collagen XI<br>Entactin/Nidogen<br>Fibronectin<br>Gelatin I<br>Laminin<br>Myelin Basic<br>Link Protein<br>Tenascin<br>Vitronectin<br>Alpha1-PI<br>Alpha1-AC<br>Alpha2-M<br>Casein<br>C1q<br>Fibrinogen<br>IL-1beta | Gallbladder | VPMS/MRGG |
| Gelatinase A | MMP2 | Aggrecan<br>Collagen I<br>Collagen III<br>Collagen IV<br>Collagen V<br>Collagen VII<br>Collagen X<br>Collagen XI<br>Decorin<br>Elastin<br>Entactin/Nidogen<br>Fibrillin<br>Fibronectin<br>Fibulins<br>Gelatin I<br>Laminin<br>Link Protein<br>Myelin Basic<br>Osteonectin | Gallbladder, urinary bladder | IPVS/L RSG SGESP AY/YTA |

FIG. 10A

| Enzyme | Gene Code | ECM Protein Degradation [5] | RNA Tissue Enhanced (*=enriched) [6] | Peptide Degrading Sequences [4] |
|---|---|---|---|---|
| Stromelysin-1 | MMP3 | Tenascin<br>Vitronectin<br>Alpha1-PI<br>Alpha1-AC<br>C1q<br>Fibrinogen<br>IL-1beta<br>Plasminogen<br>Substance P<br>Aggrecan<br>Collagen III<br>Collagen IV<br>Collagen V<br>Collagen VII<br>Collagen IX<br>Collagen X<br>Collagen XI<br>Decorin<br>Elastin<br>Entactin/Nidogen<br>Fibrillin<br>Fibronectin<br>Gelatin I<br>Laminin<br>Link Protein<br>Myelin Basic<br>Osteonectin<br>Tenascin<br>Vitronectin<br>Alpha1-PI<br>Alpha1-AC<br>Alpha2-M<br>Casein<br>C1q<br>E-cadherin<br>Fibrinogen<br>IL-1beta<br>Plasminogen<br>Substance P<br>T kininogen<br>Aggrecan<br>Collagen I | Appendix, edometrium | RPFS/MIMG |

FIG. 10B

| Enzyme | Gene Code | ECM Protein Degradation [5] | RNA Tissue Enhanced (*=enriched) [6] | Peptide Degrading Sequences [4] |
|---|---|---|---|---|
| Matrilysin | MMP7 | Collagen IV<br>Decorin<br>Elastin<br>Entactin/Nidogen<br>Fibronectin<br>Fibulins<br>Gelatin I<br>Laminin<br>Link Protein<br>Myelin Basic<br>Osteonectin<br>Tenascin<br>Vitronectin | Gallbladder | VPLS/LTMG |
| Collagenase 2 | MMP8 | Alpha1-PI<br>Casein<br>E-cadherin<br>Fibrinogen<br>Plasminogen<br>Aggrecan<br>Collagen I<br>Collagen II<br>Collagen III<br>Alpha1-PI<br>Alpha2-M<br>C1q<br>Fibrinogen<br>Substance P | Bone marrow* | |
| Gelatinase B | MMP9 | Aggrecan<br>Collagen IV<br>Collagen V<br>Collagen XI<br>Collagen XIV<br>Decorin<br>Elastin<br>Fibrillin<br>Fibronectin<br>Gelatin I<br>Laminin<br>Link Protein<br>Myelin Basic<br>Osteonectin<br>Vitronectin | Bone marrow,<br>Lymph node | VPLS/LYSG |

FIG. 10C

| Enzyme | Gene Code | ECM Protein Degradation [5] | RNA Tissue Enhanced (*=enriched) [6] | Peptide Degrading Sequences [4] |
|---|---|---|---|---|
| Stromelysin-2 | MMP10 | Alpha1-PI<br>Alpha2-M<br>Casein<br>C1q<br>Fibrinogen<br>IL-1beta<br>Plasminogen<br>Substance P<br>Aggrecan<br>Collagen III<br>Collagen IV<br>Collagen V<br>Elastin<br>Fibronectin<br>Gelatin I<br>Link Protein | Endometrium* | |
| Stromelysin-3 | MMP11 | Casein<br>Fibrinogen<br>Alpha1-PI<br>Alpha2-M | Endometrium, placenta* | GGYAE/LRMGG |
| Machrophage metalloelastase | MMP12 | Aggrecan<br>Collagen I<br>Collagen IV<br>Elastin<br>Entactin/Nidogen<br>Fibrillin<br>Fibronectin<br>Gelatin I<br>Laminin<br>Myelin Basic<br>Vitronectin<br>Alpha2-M<br>Alpha1-PI<br>Factor XII<br>Fibrinogen<br>Plasminogen<br>Substance P<br>Aggrecan<br>Collagen I<br>Collagen II<br>Collagen III<br>Collagen VI | N/A | |

FIG. 10D

| Enzyme | Gene Code | ECM Protein Degradation [5] | RNA Tissue Enhanced (*=enriched) [6] | Peptide Degrading Sequences [4] | |
|---|---|---|---|---|---|
| Collagenase-3 | MMP13 | Collagen IX Collagen X Collagen XIV Fibrillin Fibronectin Gelatin I Osteonectin Alpha2-M Casein | Urinary bladder | GPLG/LWAR | |
| MT1-MMP | MMP14 | C1q Factor XII Fibrinogen Aggrecan Collagen I Collagen II Collagen III Entactin/Nidogen Fibrillin Fibronectin Gelatin I Laminin Vitronectin Alpha1-PI Alpha2-M Factor XII Fibrinogen | All | IPES/L RAG | GGPLG /LYAG G |
| MT2-MMP | MMP15 | Collagen III Fibronectin | Mixed | | |
| MT3-MMP | MMP16 | Collagen I | Cerebral cortex | | |
| MT4-MMP | MMP17 | Collagen I | Cerebral cortex | | |
| Collagenase-4 | MMP18 | Collagen IV Fibronectin Gelatin I | N/A | | |
| RASI-1 | MMP19 | Tenascin Casein | Adipose tissue, gallbladder | | |
| Enamelysin | MMP20 | | Testis | | |
| XMMP | MMP21 | | N/A | | |
| MT5-MMP | MMP24 | | Kidney | | |
| MT6-MMP | MMP25 | | Appendix, bone marrow, spleen* | | |

FIG. 10E

| Enzyme | Gene Code | ECM Protein Degradation [5] | RNA Tissue Enhanced (*=enriched) [6] | Peptide Degrading Sequences [4] |
|---|---|---|---|---|
| Endometase, Matrilysin-2 | MMP26 | Collagen IV Fibronectin Gelatin I Alpha1-PI Fibrinogen | Endometrium* | |
| CMMP | MMP27 | | Skin | |
| Epilysin | MMP28 | | Mixed | |

| Protein | Gene Code | Average IHC score | Average RNA Expression (FPKM) | Protein Type | Tissue Enhanced (E=enriched) | Protein Reliability (S=supportive, U=uncertain) (#antibody) |
|---|---|---|---|---|---|---|
| alpha2-M | A2M | 0.0 | 3.7 | Secreted | ALL | S(2) |
| Aggrecan | ACAN | 0.0 | 0.0 | Secreted | Mixed | U(1) |
| Amyloid P Component | APCS | 2.0 | 0.0 | Secreted | Liver (E) | S(2) |
| C1q | C1QA | 0.5 | 30.2 | Secreted | ALL | S(2) |
| C1q | C1QB | 0.0 | 34.2 | Secreted | ALL | U(1) |
| C1q | C1QC | 2.0 | 24.1 | Secreted | ALL | U(2) |
| E-cadherin | CDH1 | 1.3 | 4.9 | Secreted | Mixed | S(3) |
| Collagen X | COL10A1 |  | 0.1 | Secreted | Gallbladder |  |
| Collagen XI | COL11A1 | 2.0 | 0.3 | Secreted | Placenta | U(1) |
| Collagen XI | COL11A2 |  | 0.2 | Secreted | Mixed | Pending |
| Collagen XIV | COL14A1 | 0.0 | 0.2 | Secreted | ALL | U(1) |
| Collagen 1 A1 | COL1A1 | 1.0 | 5.7 | Secreted | ALL | U(2) |
| Collagen 1 A2 | COL1A2 | 2.0 | 1.9 | Secreted | Prostate, stomach, testis | S(1) |
| Collagen II | COL2A1 | 0.0 | 0.2 | Secreted |  | U(1) |
| Collagen III | COL3A1 | 0.5 | 0.4 | Secreted | Gallbladder | U(2) |
| Collagen IV | COL4A1 | 0.0 | 0.2 | Secreted | Placenta | U(1) |
| Collagen IV | COL4A2 | 0.0 | 0.4 | Secreted | Placenta | S(1) |
| Collagen IV | COL4A3 | 0.0 | 0.3 | Secreted | Kidney | U(1) |
| Collagen IV | COL4A4 |  | 0.1 | Secreted | Mixed | Pending |
| Collagen IV | COL4A5 |  | 0.2 | Secreted | Mixed | Pending |
| Collagen IV | COL4A6 |  | 0.1 | Secreted | Smooth Muscle | Pending |
| Collagen V | COL5A1 | 0.0 | 0.6 | Secreted | Mixed | U(1) |
| Collagen V | COL5A2 |  | 0.1 | Secreted | Mixed | Pending |
| Collagen V | COL5A3 | 1.0 | 0.1 | Secreted | Mixed | U(1) |
| Collagen VI | COL6A1 | 0.0 | 0.8 | Secreted | Mixed | S(2) |
| Collagen VI | COL6A2 | 1.0 | 3.0 | Secreted | ALL | S(1) |
| Collagen VI | COL6A3 | 2.0 | 0.4 | Secreted | Smooth Muscle | U(1) |

FIG. 11B

| Protein | Gene Code | Average IHC score | Average RNA Expression (FPKM) | Protein Type | Tissue Enhanced (E=enriched) | Protein Reliability (S=supportive, U=uncertain) (#antibody) |
|---|---|---|---|---|---|---|
| Collagen VI | COL6A5 | 0.0 | 0.3 | Secreted | Lung, Skin | U(1) |
| Collagen VI | COL6A6 | 3.0 | 0.1 | Secreted | Lung | U(1) |
| Collagen VII | COL7A1 | 0.0 | 1.3 | Secreted | Skin (E) | S(2) |
| Collagen VIII | COL8A1 | 1.0 | 0.0 | Secreted | Thyroid gland | S(1) |
| Collagen VIII | COL8A2 | 1.0 | 0.3 | Secreted | Mixed | U(1) |
| Collagen IX | COL9A1 | 0.0 | 0.0 | Secreted | Prostate | Pending |
| Collagen IX | COL9A2 | 0.0 | 6.8 | Secreted | Mixed | U(1) |
| Collagen IX | COL9A3 | 1.0 | 5.2 | Secreted | Salivary gland, thyroid gland | U(1) |
| COMP | COMP | | 0.1 | Secreted | Gallbladder | Pending |
| iC3b | CR1 | 0.8 | 5.8 | Membrane, Secreted | Appendix | S(5) |
| Casein | CSN1S1 | 0.0 | 0.1 | Secreted | ALL | U(2) |
| Casein | CSN2 | 0.0 | 0.0 | Secreted | Salivary gland (E) | U(1) |
| Casein | CSN3 | 0.0 | 0.0 | Secreted | Salivary gland (E) | U(1) |
| Decorin | DCN | 0.0 | 1.7 | Secreted | ALL | S(2) |
| Elastin | ELN | 0.0 | 0.1 | Secreted | Mixed | S(3) |
| Elastin microfibril interfacer 1 | EMILIN1 | 1.0 | 0.9 | Secreted | Mixed | S(1) |
| Factor XII | F12 | 0.0 | 1.5 | Secreted | Liver (E) | S(1) |
| Factor X | F5 | 2.0 | 3.4 | Secreted | Liver, Placenta | U(1) |
| Fibulin | FBLN1 | 0.7 | 0.5 | Secreted | Mixed | S(4) |
| Fibulin | FBLN2 | 0.0 | 2.1 | Secreted | Mixed | S(2) |
| Fibulin | FBLN5 | 0.3 | 5.4 | Secreted | ALL | S(3) |
| Fibulin | FBLN7 | 3.0 | 0.5 | Secreted | Mixed | U(1) |
| Fibrillin | FBN1 | 0.0 | 4.3 | Secreted | ALL | S(5) |
| Fibrillin | FBN2 | 0.0 | 2.0 | Secreted | Placenta(E) | S(2) |
| Fibrillin | FBN3 | 0.0 | 0.0 | Secreted | Lung | U(1) |

FIG. 11C

| Protein | Gene Code | Average IHC score | Average RNA Expression (FPKM) | Protein Type | Tissue Enhanced (E=enriched) | Protein Reliability (S=supportive, U=uncertain) (#antibody) |
|---|---|---|---|---|---|---|
| Fibrinogen alpha | FGA | 1.5 | 0.0 | Secreted | Liver (E) | S(2) |
| Fibrinogen beta | FGB | 0.3 | 0.0 | Secreted | Liver (E) | S(3) |
| Fibrinogen gamma | FGG | 1.0 | 0.1 | Secreted | Liver (E) | S(1) |
| VEGF-D | FIGF | 2.0 | 0.0 | Secreted | Lung | U(1) |
| Fibronectin | FN1 | 2.0 | 4.5 | Secreted | ALL | S(2) |
| Link Protein | HAPLN1 | 0.0 | 0.0 | Secreted | Placenta | S(2) |
| ICAM | ICAM1 | 1.0 | 60.3 | Membrane, Secreted | ALL | S(3) |
| ICAM | ICAM2 | 1.0 | 15.3 | Membrane, Secreted | ALL | U(1) |
| ICAM | ICAM3 | 3.0 | 106.1 | Membrane, Secreted | ALL | S(1) |
| ICAM | ICAM4 |  | 7.7 | Membrane, Secreted | Bone Marrow, Lung | Pending |
| ICAM | ICAM5 | 0.3 | 1.2 | Membrane | Cerebral cortex, lung | S(3) |
| IGFBP-1 | IGFBP1 | 0.0 | 0.0 | Secreted | Liver, Placenta | S(3) |
| IL1beta | IL1B |  | 119.3 | Intracellular | Bone Marrow | Pending |
| T kininogen | KNG1 | 0.0 | 0.0 | Secreted | Kidney, Liver (E) | S(3) |
| Laminin Alpha | LAMA1 | 1.0 | 0.0 | Secreted | Testis | U(2) |
| Laminin Alpha | LAMA2 | 0.0 | 0.2 | Secreted | Placenta | U(1) |
| Laminin Alpha | LAMA3 | 0.5 | 0.0 | Secreted | Mixed | U(2) |
| Laminin Alpha | LAMA4 | 1.0 | 0.4 | Secreted | Mixed | U(1) |
| Laminin Alpha | LAMA5 |  | 3.7 | Secreted | ALL | Pending |
| Laminin Beta | LAMB1 | 0.3 | 2.1 | Secreted | ALL | S(3) |
| Laminin Beta | LAMB2 | 0.5 | 5.4 | Secreted | ALL | S(2) |
| Laminin Beta | LAMB3 | 0.0 | 22.2 | Secreted | Mixed | S(1) |
| Laminin Beta | LAMB4 | 0.5 | 0.0 | Secreted | Skin (E) | U(2) |

| Protein | Gene Code | Average IHC score | Average RNA Expression (FPKM) | Protein Type | Tissue Enhanced (E=enriched) | Protein Reliability (S=supportive, U=uncertain) (#antibody) |
|---|---|---|---|---|---|---|
| Laminin gamma | LAMC1 | 0.0 | 7.8 | Secreted | ALL | S(3) |
| Laminin gamma | LAMC2 | 1.5 | 0.0 | Secreted | Mixed | S(2) |
| Laminin gamma | LAMC3 | 0.0 | 0.1 | Secreted | Placenta | U(1) |
| Galectin-8 | LGALS8 | 2.0 | 52.0 | Intracellular | ALL | S(1) |
| LAP-TGF-beta | LTBP1 | 1.0 | 7.4 | Secreted | ALL | S(2) |
| LAP-TGF-beta | LTBP2 | 0.0 | 0.6 | Secreted | Mixed | U(1) |
| LAP-TGF-beta | LTBP3 | | 14.0 | Secreted | ALL | Pending |
| LAP-TGF-beta | LTBP4 | 2.0 | 10.4 | Secreted | ALL | S(1) |
| MAdCAM-1 | MADCAM1 | | 0.1 | Membrane | Appendix, Spleen | Pending |
| Myelin Basic | MBP | 0.0 | 17.6 | Intracellular | Cerebral Cortex (E) | S(2) |
| MFG-E8 | MFGE8 | 2.0 | 6.5 | Secreted | ALL | U(2) |
| Collagenase-1 | MMP1 | | 0.1 | Secreted | Gallbladder | Pending |
| Stromelysin-2 | MMP10 | 2.0 | 0.1 | Secreted | Endometrium (E) | U(1) |
| Stromelysin-3 | MMP11 | 0.0 | 0.6 | Secreted | Endometrium, Placenta (E) | S(1) |
| Macrophage metalloelastase | MMP12 | | | | | |
| Collagenase-3 | MMP13 | | 0.125 | Secreted | Urinary Bladder | Pending |
| MT1-MMP | MMP14 | 0.5 | 1.05 | Membrane,Secreted | ALL | U(2) |
| MT2-MMP | MMP15 | 1.5 | 0.25 | Membrane | Mixed | U(2) |
| MT3-MMP | MMP16 | 1.0 | 0 | Membrane | Cerebral Cortex | U(1) |
| MT4-MMP | MMP17 | | 3.225 | Secreted | Cerebral Cortex | Pending |
| Collagenase-4 | MMP18 | | | | | |
| RASI-1 | MMP19 | 2.0 | 1.25 | Secreted | Adipose tissue, Gallbladder | U(1) |

FIG. 11D

| Protein | Gene Code | Average IHC score | Average RNA Expression (FPKM) | Protein Type | Tissue Enhanced (E=enriched) | Protein Reliability (S=supportive, U=uncertain) (#antibody) |
|---|---|---|---|---|---|---|
| Gelatinase A | MMP2 | 1.0 | 0.8 | Secreted | Gallbladder, Urinary bladder | U(2) |
| Enamelysin | MMP20 | | 0 | Secreted | | Pending |
| XMMP | MMP21 | 1.0 | 0.05 | Secreted | Testis | U(1) |
| CMMP | MMP22 | | | | | |
| MT5-MMP | MMP24 | 3.0 | 0.175 | Membrane | | U(1) |
| MT6-MMP | MMP25 | 2.0 | 45.575 | Secreted | Kidney Appendix, Bone Marrow, Spleen (E) | U(1) |
| Endometase, Matrilysin-2 | MMP26 | 2.0 | 0 | Secreted | Endometrium (E) | U(1) |
| Epilysin | MMP28 | | 0.475 | Secreted | Mixed | Pending |
| Stromelysin-1 | MMP3 | 1.5 | 0.025 | Secreted | Appendix, Eddometrium | U(2) |
| Matrilysin | MMP7 | 0.0 | 0.125 | Secreted | Gallbladder | U(1) |
| Collagenase02 | MMP8 | 3.0 | 334.6 | Secreted | Bone Marrow (E) | S(2) |
| Gelatinase B | MMP9 | 2.8 | 181.775 | Secreted | Bone Marrow, Lymph node | S(6) |
| Entactin/Nidogen | NID-1 | 2.0 | 1.6 | Secreted | ALL | S(1) |
| Netrin-1 | NTN1 | 2.0 | 0.125 | Secreted | Mixed | U(1) |
| PECAM-1 | PECAM1 | | | | | |
| uPAR | PLAUR | 2.0 | 360.025 | Membrane, Secreted | Bone Marrow | U(1) |
| Plasminogen | PLG | 0.7 | 0.075 | Secreted Protein | Liver(E) | S(3) |
| Reelin | RELN | 0.0 | 0.3 | Secreted | Liver | U(1) |
| alpha1-PI | SERPINA1 | 1.6 | 101.625 | Secreted | Liver (E) | S(5) |

FIG. 11E

| Protein | Gene Code | Average IHC score | Average RNA Expression (FPKM) | Protein Type | Tissue Enhanced (E=enriched) | Protein Reliability (S=supportive, U=uncertain) (#antibody) |
|---|---|---|---|---|---|---|
| alpha1-AC | SERPINA3 | 1.0 | 0.35 | Secreted | Liver (E) | S(3) |
| Substance P | SP | | | | | |
| Osteonectin | SPARC | 2.0 | 37.675 | Secreted | ALL | S(3) |
| Osteopontin | SPP1 | 1.5 | 0.8 | Secreted | Cerebral Cortex, Gallbladder, Kidney, Placenta | U(2) |
| Thrombospondin | THBS1 | 2.0 | 79.15 | Secreted | Mixed | S(1) |
| Thrombospondin | THBS2 | 2.0 | 0.15 | Secreted | Gallbladder | U(1) |
| Thrombospondin | THBS3 | 0.0 | 9.325 | Secreted | ALL | U(1) |
| Thrombospondin | THBS4 | 0.0 | 16.6 | Secreted | Adipose tissue, heart muscle, smooth muscle | U(1) |
| Tenascin C | TNC | 0.5 | 0.675 | Secreted | Smooth Muscle | S(2) |
| Tenascin N | TNN | 0.5 | 0 | Secreted | Adipose Tissue | U(3) |
| Tenascin R | TNR | 0.8 | 0 | Secreted | Cerebral Cortex | S(4) |
| Tenascin XB | TNXB | 2.0 | 5.65 | Secreted | ALL | U(1) |
| VCAM-1 | VCAM1 | 2.5 | 5.95 | Membrane | Spleen | S(2) |
| VEGFA | VEGFA | 3.0 | 36.825 | Secreted | ALL | S(1) |
| VEGFB | VEGFB | 3.0 | 9.925 | Secreted | ALL | U(1) |
| VEGF-C | VEGFC | | 0.7 | Secreted | Mixed | Pending |
| Vitronectin | VTN | 1.5 | 0.15 | Secreted | Liver | S(4) |
| vWF | vWF | 2.0 | 0.675 | Secreted | Mixed | S(3) |

FIG. 11F

| Gene Code | Protein/Enzyme | Average Protein Score | Expression (FPKM) | % Included in Mimic | Synthesize Peptide Sequence | Binding/Degradable Moiety |
|---|---|---|---|---|---|---|
| NID-1 | Entactin/Nidogen | 2.0 | 1.6 | | | |
| VTN | Vitronectin | 1.5 | 0.2 | | GRGDSPCG | RGD |
| vWF | von Willebrand Factor | 2.0 | 0.7 | 30 | | |
| NTN1 | Netrin-1 | 2.0 | 0.1 | 11 | GCGGQWRDTWARRL RKFQQREKKGKCRKA CGPHSRNGGGGGGR | QWRDTWARRLRK FQQREKKGKCRKA |
| FN1 | Fibronectin | 2.0 | 4.5 | 11 | GDS | PHSRN-RGD |
| SPP1 | Osteopontin | 1.5 | 0.8 | 8 | CGGSVVYGLR | SVVYGLR |
| COL1A1,2 | Collagen I | 1.5 | 3.8 | 8 | CGP(GPP)5GFOGER(G PP)5 | GFOGER |
| FGA | Fibrinogen | 1.5 | 0.0 | 8 | GPRGGC | GPR |
| THBS1,2,3,4 | Thrombospondin | 1.0 | 26.3 | 5 | CSVTCG | VTXG |
| FGG | Fibrinogen | 1.0 | 0.1 | 5 | CGGYSMKKTTMKIIPF NRLTIG | YSMKKTTMKIIPFN RLTIG |
| TNC | Tenascin C | 0.5 | 0.7 | 3 | CGGAEIDGIEL | AEIDGIEL |
| COL9A1,2,3 | Collagen IX | 0.5 | 4.0 | 3 | GCGDGEA | DGEA |
| LAMA1,2,3,4,5 | Laminin Alpha | 0.6 | 0.9 | 3 | CSRARKQAASIKVAVA DR | IKVAV |
| LAMB1,2,3,4 | Laminin Beta | 0.3 | 7.4 | 2 | GCDPGYIGSR | YIGSR |
| LAMC1,2,3 | Laminin gamma | 0.5 | 2.6 | 1 | GCKQLREQ | LRE |

FIG. 12

| Gene Code | Protein/ Enzyme | Protein Degradation | Average Protein Score | Average RNA Expression (FPKM) | % Included in Mimic | Synthesize Petide Sequence | Binding/ Degradable Moiety | Protein Degradation |
|---|---|---|---|---|---|---|---|---|
| MMP1 | Collagenase-1 | C1q | 0.8 | 29.5 | | | | Collagen XI |
| | | Collagen XI | 1.0 | 0.3 | | | | Collagen XI |
| | | Collagen I | 1.5 | 3.8 | | | | Collagen XI |
| | | Collagen III | 0.5 | 0.4 | | | | Entactin |
| | | Collagen VIII | 1.0 | 0.2 | | | | Entactin |
| | | Fibrinogen | 0.9 | 0.0 | 17 | GCRDVPMSM RGGDRCG | VPMS/MRGG | Entactin |
| | | Laminins | 0.5 | 3.5 | | | | Entactin |
| | | Fibronectin | 2 | 4.5 | | | | Fibulin |
| | | Entactin | 2 | 1.6 | | | | Fibulin |
| | | Alpha1-PI | 1.6 | 101.625 | | | | Osteonectin |
| | | Tenascins | 0.9 | 1.58125 | | | | Osteonectin |
| | | Vitronectin | 1.5 | 0.15 | | | | Osteonectin |
| | | Entactin | 2 | 1.6 | | | | Osteonectin |
| | | Plasminogen | 0.7 | 0.075 | | | | Osteonectin |
| | | Alpha1-PI | 1.6 | 101.625 | | | | Plasminogen |
| | | Alpha1-AC | 1.0 | 0.35 | | | | Plasminogen |
| | | Osteonectin | 2.0 | 37.675 | | | | Plasminogen |
| | | Tenascins | 0.9 | 1.58125 | | | | Plasminogen |
| | | Vitronectin | 1.5 | 0.15 | | | | |
| MMP2 | Gelatinase A | Laminins | 0.5 | 3.5 | | | | |
| | | Fibronectin | 2 | 4.5 | 20 | GCRDSGESP AYYTADRCG | SGESPAY/YT A | |
| | | Fibulin | 1 | 2.10625 | | | | |
| | | Fibrinogen | 0.9 | 0.0 | | | | |
| | | Collagen I | 1.5 | 3.8 | | | | |
| | | C1q | 0.8333333333 | 29.5 | | | | |
| | | Collagen XI | 1.0 | 0.3 | | | | |
| | | Collagen III | 0.5 | 0.4 | | | | |
| | | Collagen V | 0.33 | 0.266666667 | | | | |
| | | Vitronectin | 1.5 | 0.15 | | | | |
| | | Tenascins | 0.9 | 1.58125 | | | | |
| | | Osteonectin | 2.0 | 37.675 | | | | |
| | | Alpha1-AC | 1.0 | 0.35 | | | | |

FIG. 13A

| Gene Code | Protein/ Enzyme | Protein Degradation | Average Protein Score | Average RNA Expression (FPKM) | % Included in Mimic | Synthesize Petide Sequence | Binding/ Degradable Moiety | Protein Degradation |
|---|---|---|---|---|---|---|---|---|
| | | Alpha1-PI | 1.6 | 101.625 | | | | |
| | | Plasminogen | 0.7 | 0.075 | | | | |
| | | Entactin | 2 | 1.6 | | | | |
| | | Laminins | 0.5 | 3.5 | | | | |
| | | Fibronectin | 2 | 4.5 | | | | |
| | | Fibrinogen | 0.9 | 0.0 | | | | |
| | | C1q | 0.833333333 | 29.5 | | | | |
| | | Collagen IX | 0.33 | 4 | | | | |
| | | Collagen V | 0.33 | 0.266666667 | | | | |
| | | Collagen III | 0.5 | 0.4 | | | | |
| MMP3 | Stromelysin-1 | Collagen XI | 1.0 | 0.3 | 19 | GCRDRPFSMI MGDRCG | RPFS/MIMG | |
| | | Entactin | 2 | 1.6 | | | | |
| | | Plasminogen | 0.7 | 0.075 | | | | |
| | | Alpha1-PI | 1.6 | 101.625 | | | | |
| | | Osteonectin | 2.0 | 37.675 | | | | |
| | | Tenascins | 0.9 | 1.58125 | | | | |
| | | Vitronectin | 1.5 | 0.15 | | | | |
| | | Fibronectin | 2 | 4.5 | | | | |
| | | Fibrinogen | 0.9 | 0.0 | | | | |
| | | Fibulin | 1 | 2.10625 | | | | |
| MMP7 | Matrilysin | Collagen I | 1.5 | 3.8 | 15 | GCRDVPLSLT MGDRCG | VPLS/LTMG | |
| | | Laminins | 0.5 | 3.5 | | | | |
| | | Plasminogen | 0.7 | 0.075 | | | | |
| | | Alpha1-PI | 1.6 | 101.625 | | | | |
| | | Osteonectin | 2.0 | 37.675 | | | | |
| | | Vitronectin | 1.5 | 0.15 | | | | |
| | | Collagen XI | 1.0 | 0.3 | | | | |
| | | Collagen V | 0.33 | 0.266666667 | | | | |
| | | Fibrinogen | 0.9 | 0.0 | | | | |
| MMP9 | Gelatinase B | C1q | 0.833333333 | 29.5 | 10 | GCRDVPLSY SGDRCG | VPLS/LYSG | |
| | | Osteonectin | 2.0 | 37.875 | | | | |
| | | Fibronectin | 2 | 4.5 | | | | |

FIG. 13B

| Gene Code | Protein/ Enzyme | Protein Degradation | Average Protein Score | Average RNA Expression (FPKM) | % Included in Mimic | Synthesize Petide Sequence | Binding/ Degradable Moiety | Protein Degradation |
|---|---|---|---|---|---|---|---|---|
| MMP13 | Collagenase-3 | Fibrinogen | 0.9 | 0.0 | | | | |
| | | Collagen IX | 0.33 | 4 | | | | |
| | | Collagen VI | 1.2 | 0.9095 | | | | |
| | | C1q | 0.833333333 | 29.5 | | | | |
| | | Collagen III | 0.5 | 0.4 | | | | |
| | | Collagen I | 1.5 | 3.8 | 10 | GCRDGPLGL WARDRCG | GPLG/LWAR | |
| | | Collagen III | 0.5 | 0.4 | | | | |
| | | Laminins | 0.5 | 3.5 | | | | |
| | | Entactin | 2 | 1.6 | | | | |
| | | Alpha1-PI | 1.6 | 101.625 | | | | |
| | | Vitronectin | 1.5 | 0.15 | | | | |
| | | Fibronectin | 2 | 4.5 | | | | |
| | | Fibrinogen | 0.9 | 0.0 | | | | |
| MMP14 | MT1-MMP | Collagen I | 1.5 | 3.8 | 10 | GCRDIPESLR AGDRCG | IPES/LRAG | |

FIG. 13C

| Score A3 | Coverage A | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| | | | | 16.1113331 | 21.8 | 4 | 8 | 367 | 39.3156893 | 5.71923828 |
| | | | | 24.32938 | 51.01 | 6 | 22 | 149 | 16.500353 | 8.08935547 |
| | | | | | | | | 2871 | 312.022496 | 4.93212891 |
| 102.805603 | 11.95 | 20 | 50 | 6.88508141 | 15.72 | 25 | 57 | 2296 | 252.662383 | 5.93505859 |
| 2.63111782 | 5.2 | 3 | 3 | | | | | 1039 | 113.30552 | 5.37646484 |
| 26.2351041 | 3.04 | 3 | 11 | | | | | 1152 | 127.098527 | 7.22507656 |
| 5.41475725 | 12.5 | 4 | 6 | | | | | 480 | 55.0105479 | 6.94677734 |
| 17.7374524 | 14.16 | 6 | 10 | | | | | 586 | 66.3676257 | 5.16064453 |
| | | | | 10.568528 | | | 8 | 92 | 10.568528 | 6.25244141 |
| | | | | 76.7063789 | 27.95 | 661 | 1413 | 33423 | 3711.28551 | 6.52197266 |
| 41.9115322 | 22.83 | 6 | 15 | 20.2826663 | 38.44 | 10 | 21 | 346 | 38.689981 | 7.02001953 |
| 22.1177251 | 16.22 | 3 | 8 | 14.7092767 | 31.27 | 9 | 14 | 339 | 38.5798164 | 7.75244141 |
| 58.5859183 | 27.55 | 8 | 21 | 32.4711623 | 39.63 | 11 | 22 | 323 | 36.3526603 | 5.92236328 |
| 23.1640447 | 11.56 | 4 | 9 | 22.0186863 | 31.25 | 10 | 29 | 320 | 35.9144026 | 5.04638672 |
| 101.679792 | 21.69 | 12 | 36 | 55.3306227 | 44.28 | 19 | 44 | 673 | 75.8255803 | 5.60498047 |
| 80.8051357 | 28.29 | 5 | 26 | 23.8372374 | 66.14 | 13 | 30 | 251 | 26.8685563 | 9.49560547 |
| 23.1918223 | 13.51 | 3 | 10 | 0 | 31.53 | 5 | 14 | 222 | 25.1892583 | 6.75634766 |
| 33.8128351 | 21.96 | 5 | 16 | 10.2305074 | 22.75 | 6 | 10 | 255 | 28.819071 | 11.1848242 |
| 0 | 1.46 | 1 | 2 | 3.35296297 | 22.18 | 12 | 20 | 1028 | 108.462017 | 5.42724609 |
| 1.69151211 | 8.08 | 6 | 6 | 4.57139385 | 26.52 | 31 | 50 | 1806 | 180.953694 | 5.17333984 |
| 10.1774035 | 4.94 | 4 | 4 | 5.77238917 | 24.05 | 32 | 46 | 1497 | 150.326498 | 8.79248047 |
| 0 | 18.33 | 6 | 8 | 39.6772741 | 37.41 | 13 | 52 | 540 | 51.9122689 | 7.25439453 |
| 52.2841781 | 7.25 | 7 | 21 | 36.6718194 | 31.11 | 26 | 63 | 1366 | 129.235451 | 8.95361328 |
| 36.2489007 | 5.79 | 3 | 10 | 1.69540627 | 31.5 | 27 | 40 | 1019 | 108.511941 | 6.21435547 |
| 33.8476468 | 4.33 | 6 | 19 | 19.1054124 | 23.27 | 27 | 56 | 1663 | 187.029884 | 6.40478516 |
| 3.53959799 | 1.2 | 2 | 2 | 0 | 23.05 | 24 | 48 | 1744 | 192.66448 | 7.07861328 |
| 0 | 3.17 | 1 | 1 | 16.9743094 | 20.86 | 8 | 18 | 537 | 60.0921297 | 5.84619141 |
| 37.8041885 | 4.73 | 3 | 12 | 1.61935699 | 27.25 | 20 | 31 | 866 | 94.9144192 | 6.01123047 |
| 69.3355619 | 21.38 | 10 | 29 | 22.8430486 | 47.66 | 18 | 41 | 491 | 55.8922633 | 8.26513672 |
| 57.1057235 | 22.08 | 7 | 19 | 4.54795432 | 31.13 | 8 | 14 | 453 | 51.4788689 | 5.61767578 |
| 13.3446093 | 11.44 | 5 | 10 | 7.8155055 | 28.09 | 15 | 33 | 769 | 84.7261308 | 6.94677734 |
| 12.9459109 | 3.17 | 2 | 4 | 0 | 10.04 | 9 | 14 | 946 | 106.396614 | 6.85888672 |

FIG. 14A-1

| Accession | Description | ΣCoverage | Σ# Proteins que Peptides | Σ# Peptides | Σ# PSMs |
|---|---|---|---|---|---|
| P11047;145309326 | Laminin subunit gamma-1 | 43.19 | 1 | 49 | 189 |
| P14780;74272287 | Matrix metalloproteinase-9 | 41.02 | 4 | 20 | 63 |
| P08246;4503549 | Neutrophil elastase | 34.83 | 2 | 4 | 21 |
| P05155;73858568 | Plasma protease C1 inhibitor | 38 | 4 | 13 | 23 |
| P49257;5031873 | Protein ERGIC-53 | 28.82 | 1 | 10 | 18 |
| P05109;21614544 | Protein S100-A8 | 47.31 | 6 | 9 | 39 |
| P06702;4506773 | Protein S100-A9 | 71.93 | 4 | 7 | 42 |
| Q9Y2Y8;223633965 | Proteoglycan 3 | 52.44 | 1 | 9 | 17 |
| P08575;18641347 | Receptor-type tyrosine-protein phosphatase | 41.64 | 8 | 41 | 113 |
| P07996;40317626 | Thrombospondin-1 | 31.79 | 3 | 25 | 50 |
| Q07283;148746195 | Trichohyalin | 63.66 | 1 | 137 | 316 |
| P04004;88853069 | Vitronectin | 23.01 | 2 | 9 | 19 |
| P12956;4503841 | X-ray repair cross-complementing protein 6 | 28.24 | 1 | 12 | 19 |

FIG. 14A-2

| Score A3 | Coverage A3 | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| | | | | 16.1113331 | 21.8 | 4 | 8 | 367 | 39.3156893 | 5.71923828 |
| | | | | 24.32938 | 51.01 | 6 | 22 | 149 | 16.500353 | 8.08935547 |
| 102.805603 | 11.95 | 20 | 50 | | | | | 2871 | 312.022496 | 4.93212891 |
| | | | | 6.88508141 | 15.72 | 25 | 57 | 2296 | 252.662383 | 5.93505859 |
| 2.63111782 | 5.2 | 3 | 3 | | | | | 1039 | 113.30552 | 5.37646484 |
| 26.2351041 | 3.04 | 3 | 11 | | | | | 1152 | 127.098527 | 7.22509766 |
| 5.41475725 | 12.5 | 4 | 6 | | | | | 480 | 55.0105479 | 6.94677734 |
| 17.7374524 | 14.16 | 6 | 10 | | | | | 586 | 66.3676257 | 5.16064453 |
| | | | | | | | 8 | 92 | 10.568528 | 6.25244141 |
| | | | | 16.7096295 | 51.09 | 4 | 1413 | 33423 | 3711.28551 | 6.52197266 |
| 41.9115322 | 22.83 | 6 | 15 | 76.7063789 | 27.95 | 661 | 21 | 346 | 38.689981 | 7.02001953 |
| 22.1177251 | 16.22 | 3 | 8 | 20.2826663 | 38.44 | 10 | 14 | 339 | 38.5798164 | 7.75244141 |
| 58.5859183 | 27.55 | 8 | 21 | 14.7092767 | 31.27 | 9 | 22 | 323 | 35.3526603 | 5.92236328 |
| 23.1640447 | 11.56 | 4 | 9 | 32.4711623 | 39.63 | 11 | 29 | 320 | 35.9144026 | 5.04638672 |
| 101.679792 | 21.69 | 12 | 36 | 22.0186863 | 31.25 | 10 | 44 | 673 | 75.8255803 | 5.60498047 |
| 80.8051357 | 28.29 | 5 | 26 | 55.3306227 | 44.28 | 19 | 30 | 251 | 26.8686563 | 9.49560547 |
| 23.1918223 | 13.51 | 3 | 10 | 23.8372374 | 66.14 | 13 | 14 | 222 | 25.1892583 | 6.75634766 |
| 33.8128351 | 21.96 | 5 | 16 | 0 | 31.53 | 5 | 10 | 255 | 28.819071 | 11.1948242 |
| 0 | 1.46 | 1 | 2 | 10.2305074 | 22.75 | 6 | 20 | 1028 | 108.462017 | 5.42724609 |
| 1.69151211 | 8.08 | 6 | 6 | 3.35296297 | 22.18 | 12 | 50 | 1806 | 180.953694 | 5.17333984 |
| 10.1774035 | 4.94 | 4 | 8 | 4.57139385 | 26.52 | 31 | 46 | 1497 | 150.326498 | 8.79248047 |
| 0 | 18.33 | 4 | 6 | 5.77238917 | 24.05 | 32 | 52 | 540 | 51.9122689 | 7.25439453 |
| 52.2841781 | 7.25 | 7 | 21 | 39.6772741 | 37.41 | 13 | 63 | 1366 | 129.235451 | 8.95361328 |
| 36.2489007 | 5.79 | 3 | 10 | 36.6718194 | 31.11 | 26 | 40 | 1019 | 108.511941 | 6.21435547 |
| 33.8476468 | 4.33 | 6 | 19 | 1.69540067 | 31.5 | 27 | 56 | 1663 | 187.029884 | 6.40478516 |
| 3.53959799 | 1.2 | 2 | 2 | 19.1054124 | 23.27 | 27 | 48 | 1744 | 192.66448 | 7.07861328 |
| 0 | 3.17 | 1 | 1 | 0 | 23.05 | 24 | 18 | 537 | 60.0921297 | 5.84619141 |
| 37.8041885 | 4.73 | 3 | 12 | 16.9743094 | 20.86 | 8 | 31 | 856 | 94.9144192 | 6.01123047 |
| 69.3355619 | 21.38 | 10 | 29 | 1.61935699 | 27.25 | 20 | 41 | 491 | 55.8922633 | 8.26513672 |
| 57.1057235 | 22.08 | 7 | 19 | 22.8430486 | 47.66 | 18 | 14 | 453 | 51.4788689 | 5.61767578 |
| 13.3446093 | 11.44 | 5 | 10 | 4.54795432 | 31.13 | 8 | 33 | 769 | 84.7261308 | 6.94677734 |
| 12.9459109 | 3.17 | 2 | 4 | 7.8155055 | 28.09 | 15 | 14 | 946 | 106.396614 | 6.85888672 |

FIG. 14A-3

| Score A3 | Coverage A3 | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| 2.30691266 | 5.84 | 7 | 7 | 21.8471038 | 40.46 | 46 | 182 | 1609 | 177.488558 | 5.12255859 |
| 30.5217959 | 9.19 | 5 | 13 | 19.3036189 | 39.46 | 16 | 50 | 707 | 78.4083601 | 6.06201172 |
| 8.14940643 | 6.37 | 2 | 9 | 5.96779764 | 32.21 | 3 | 12 | 267 | 28.4997899 | 9.34912109 |
| 33.3996553 | 14.4 | 5 | 12 | 0 | 26.8 | 9 | 11 | 500 | 55.1193964 | 6.55126953 |
| 0 | 5.88 | 2 | 2 | 10.5535419 | 22.94 | 8 | 16 | 510 | 57.5129839 | 6.77099609 |
| 65.8363081 | 37.63 | 6 | 33 | 9.92640162 | 35.48 | 4 | 6 | 93 | 10.8276497 | 7.03466797 |
| 55.4490516 | 43.86 | 4 | 24 | 32.1179693 | 71.93 | 7 | 18 | 114 | 13.2335088 | 6.12548828 |
| 7.13187206 | 2.67 | 1 | 5 | 5.71891892 | 52.44 | 9 | 12 | 225 | 25.3890121 | 4.80517578 |
| 21.5283154 | 12.81 | 10 | 17 | 18.0150539 | 35.35 | 35 | 96 | 1304 | 147.161817 | 6.15087891 |
| 34.1246862 | 9.91 | 6 | 12 | 11.6403794 | 25.3 | 21 | 38 | 1170 | 129.299561 | 4.94482422 |
| 6.49343 61 | 5.76 | 8 | 13 | 20.2807974 | 63.36 | 135 | 303 | 1943 | 253.776925 | 5.78271484 |
| 16.566921 | 2.51 | 1 | 5 | 1.86097383 | 23.01 | 8 | 14 | 478 | 54.27117 | 5.79541016 |
| 3.69802938 | 1.31 | 1 | 2 | 6.03111351 | 28.24 | 12 | 17 | 609 | 69.7990575 | 6.63916016 |

FIG. 14A-4

| Accession | Description | ΣCoverage | Σ# Proteins | Unique Peptid | Σ# Peptides | Σ# PSMs |
|---|---|---|---|---|---|---|
| 5292161 | 26S proteasome non-ATPase regulatory subunit 4 | 29.97 | 1 | 1 | 9 | 15 |
| 56121815 | A disintegrin and metalloproteinase with thrombospondin motifs 10 preproprote | 36.54 | 1 | 1 | 26 | 57 |
| 51558724 | A disintegrin and metalloproteinase with thrombospondin motifs 12 preproprote | 40.84 | 1 | 1 | 45 | 94 |
| 21265037 | A disintegrin and metalloproteinase with thrombospondin motifs 3 preproprotei | 60.5 | 1 | 1 | 55 | 114 |
| 53692189 | adipocyte enhancer-binding protein 1 precursor | 36.36 | 1 | 1 | 31 | 56 |
| 256017259 | aggrecan core protein isoform 1 precursor | 16.08 | 2 | 11 | 27 | 86 |
| 50659080 | alpha-1-antichymotrypsin precursor | 73.52 | 1 | 3 | 18 | 26 |
| 50363217 | alpha-1-antitrypsin precursor | 46.89 | 1 | 16 | 26 | 95 |
| 115583663 | alpha-2-antiplasmin isoform a precursor | 29.12 | 2 | 2 | 12 | 31 |
| 156523970 | alpha-2-HS-glycoprotein | 34.06 | 1 | 3 | 9 | 25 |
| 66932947 | alpha-2-macroglobulin precursor | 36.3 | 2 | 27 | 47 | 147 |
| 4557287 | angiotensinogen preproprotein | 10.72 | 1 | 1 | 4 | 12 |
| 4502101 | annexin A1 | 82.37 | 1 | 20 | 33 | 103 |
| 50845388 | annexin A2 isoform 1 | 84.31 | 2 | 14 | 39 | 104 |
| 4502107 | annexin A5 | 67.19 | 1 | 2 | 19 | 33 |
| 71773415 | annexin A6 isoform 2 | 53.67 | 2 | 4 | 36 | 53 |
| 4507065 | antileukoproteinase precursor | 78.03 | 1 | 7 | 19 | 51 |
| 4502261 | antithrombin-III precursor | 45.04 | 1 | 4 | 25 | 62 |
| 4502253 | asialoglycoprotein receptor 2 isoform a | 44.05 | 3 | 1 | 12 | 27 |
| 116734710 | ATP-binding cassette sub-family A member 3 | 41.73 | 1 | 10 | 55 | 116 |
| 11342670 | azurocidin preproprotein | 60.56 | 1 | 1 | 9 | 77 |
| 126012571 | basement membrane-specific heparan sulfate proteoglycan core protein precurs | 27.72 | 1 | 1 | 80 | 140 |
| 153266841 | beta-2-glycoprotein 1 precursor | 52.75 | 1 | 5 | 12 | 23 |
| 4502403 | biglycan preproprotein | 40.76 | 1 | 4 | 12 | 24 |
| 462768899 | bone marrow proteoglycan preproprotein | 65.32 | 1 | 4 | 13 | 33 |
| 260654089 | brorin precursor | 60.92 | 1 | 1 | 16 | 31 |
| 4885589 | C-X-C motif chemokine 11 precursor | 67.02 | 1 | 1 | 10 | 20 |
| 4502503 | C4b-binding protein alpha chain precursor | 68.68 | 1 | 15 | 38 | 140 |
| 62912462 | C4b-binding protein beta chain isoform 2 precursor | 29.08 | 2 | 1 | 7 | 18 |
| 7656967 | cadherin EGF LAG seven-pass G-type receptor 1 precursor | 37.86 | 1 | 1 | 84 | 183 |
| 256217721 | carboxypeptidase N subunit 2 | 23.67 | 1 | 2 | 8 | 19 |
| 4503139 | cathepsin B preproprotein | 30.38 | 1 | 1 | 8 | 13 |
| 4503143 | cathepsin D preproprotein | 41.75 | 1 | 2 | 12 | 23 |
| 4503149 | cathepsin G preproprotein | 71.76 | 1 | 6 | 20 | 45 |
| 89886217 | cerebellin-3 precursor | 54.63 | 1 | 1 | 6 | 13 |
| 4502907 | chymase preproprotein | 56.28 | 1 | 2 | 10 | 31 |

FIG. 14B-1

| Accession | Description | Coverage | # Proteins | Unique Peptid | # Peptides | # PSMs |
|---|---|---|---|---|---|---|
| 110349772 | collagen alpha-1(I) chain preproprotein | 59.63 | 1 | 6 | 52 | 120 |
| 111118974 | collagen alpha-1(II) chain isoform 2 precursor | 56.91 | 2 | 6 | 62 | 152 |
| 4502951 | collagen alpha-1(III) chain preproprotein | 54.98 | 1 | 2 | 56 | 107 |
| 148536825 | collagen alpha-1(IV) chain preproprotein | 31.76 | 1 | 1 | 38 | 72 |
| 89275751 | collagen alpha-1(V) chain preproprotein | 45.32 | 1 | 1 | 69 | 255 |
| 87196339 | collagen alpha-1(VI) chain precursor | 53.99 | 1 | 3 | 42 | 74 |
| 4502961 | collagen alpha-1(VIII) chain precursor | 56.15 | 1 | 1 | 113 | 220 |
| 112734845 | collagen alpha-1(XX) chain | 38.47 | 1 | 1 | 32 | 57 |
| 48762934 | collagen alpha-2(I) chain precursor | 40.7 | 1 | 3 | 39 | 102 |
| 89363017 | collagen alpha-2(V) chain preproprotein | 46.1 | 1 | 1 | 53 | 139 |
| 115527052 | collagen alpha-2(VIII) chain isoform 2C2 precursor | 66.54 | 1 | 1 | 49 | 91 |
| 89142733 | collagen alpha-3(V) chain isoform 2 precursor | 54.55 | 4 | 1 | 60 | 192 |
| 55743098 | collagen alpha-3(VI) chain isoform 1 precursor | 45.04 | 5 | 7 | 108 | 231 |
| 156616290 | collagen alpha-6(VI) chain precursor | 46.88 | 1 | 1 | 84 | 193 |
| 87298828 | complement C1q subcomponent subunit B precursor | 36.36 | 2 | 2 | 9 | 23 |
| 56786155 | complement C1q subcomponent subunit C precursor | 43.67 | 1 | 2 | 7 | 15 |
| 152298678 | complement C3 precursor | 48.53 | 1 | 20 | 73 | 157 |
| 178557739 | complement C4-B preproprotein | 39.05 | 4 | 3 | 59 | 123 |
| 67782358 | complement factor B preproprotein | 51.57 | 1 | 13 | 35 | 96 |
| 62739186 | complement factor H isoform a precursor | 55 | 2 | 13 | 62 | 128 |
| 118442839 | complement factor H-related protein 1 precursor | 57.58 | 2 | 1 | 18 | 43 |
| 28373119 | contactin-1 isoform 2 precursor | 29.79 | 2 | 1 | 22 | 29 |
| 4505463 | contactin-associated protein 1 precursor | 38.22 | 1 | 1 | 35 | 98 |
| 4503015 | copine-3 | 47.67 | 9 | 3 | 21 | 36 |
| 92110053 | CUB and sushi domain-containing protein 2 | 23.11 | 1 | 1 | 45 | 123 |
| 4503117 | cystatin-B | 52.04 | 1 | 3 | 4 | 19 |
| 4502271 | decorin isoform a preproprotein | 40.39 | 5 | 7 | 19 | 56 |
| 27735143 | discoidin, CUB and LCCL domain-containing protein 1 | 53.99 | 1 | 1 | 28 | 120 |
| 45433501 | EMILIN-3 | 39.3 | 1 | 1 | 21 | 39 |
| 191252816 | extracellular leucine-rich repeat and fibronectin type-III domain-containing prote | 35.51 | 1 | 1 | 21 | 45 |
| 256000767 | extracellular matrix protein FRAS1 isoform 1 precursor | 26.32 | 1 | 2 | 69 | 118 |
| 281485550 | fibrillin-1 precursor | 37.51 | 1 | 22 | 78 | 200 |
| 4503689 | fibrinogen alpha chain isoform alpha-E preproprotein | 58.2 | 2 | 36 | 75 | 352 |
| 70905435 | fibrinogen beta chain isoform 1 preproprotein | 74.54 | 1 | 31 | 47 | 264 |
| 70906437 | fibrinogen gamma chain isoform gamma-A precursor | 89.24 | 2 | 33 | 46 | 244 |
| 47132549 | fibronectin isoform 6 preproprotein | 45.82 | 7 | 33 | 74 | 198 |

FIG. 14B-2

| Accession | Description | %Coverage | # Proteins | Unique Peptide | # Peptides | # PSMs |
|---|---|---|---|---|---|---|
| 62122917 | filaggrin-2 | 30.78 | 1 | 1 | 41 | 67 |
| 116805322 | filamin-C isoform a | 48.77 | 2 | 1 | 104 | 297 |
| 79749430 | FRAS1-related extracellular matrix protein 2 precursor | 26.25 | 1 | 4 | 62 | 141 |
| 270265871 | FRAS1-related extracellular matrix protein 3 precursor | 26.46 | 1 | 1 | 41 | 85 |
| 4504981 | galectin-1 | 31.85 | 1 | 1 | 4 | 7 |
| 115430223 | galectin-3 isoform 1 | 32.4 | 2 | 2 | 8 | 16 |
| 4504985 | galectin-7 | 33.82 | 1 | 1 | 3 | 4 |
| 102469694 | galectin-9 isoform short | 39.63 | 4 | 2 | 10 | 27 |
| 153792495 | growth/differentiation factor 15 | 41.88 | 1 | 1 | 16 | 115 |
| 4885259 | growth/differentiation factor 9 precursor | 71.47 | 1 | 1 | 19 | 31 |
| 118572606 | hemicentin-1 precursor | 28.13 | 1 | 2 | 112 | 207 |
| 11321561 | hemopexin precursor | 46.32 | 2 | 2 | 17 | 44 |
| 4504489 | histidine-rich glycoprotein precursor | 21.71 | 1 | 1 | 15 | 39 |
| 10835071 | HLA class II histocompatibility antigen gamma chain isoform b | 57.33 | 3 | 1 | 10 | 15 |
| 4503053 | hyaluronan and proteoglycan link protein 1 precursor | 39.27 | 1 | 5 | 18 | 50 |
| 257196151 | immunoglobulin-like and fibronectin type III domain-containing protein 1 | 64.56 | 1 | 1 | 172 | 372 |
| 38569396 | insulin-like peptide INSL6 precursor | 80.28 | 1 | 1 | 14 | 26 |
| 90193622 | integrator complex subunit 6 isoform b | 41.76 | 2 | 2 | 32 | 81 |
| 156119625 | inter-alpha-trypsin inhibitor heavy chain H1 isoform a | 25.91 | 2 | 2 | 21 | 51 |
| 70778918 | inter-alpha-trypsin inhibitor heavy chain H2 | 31.61 | 1 | 4 | 25 | 41 |
| 262050539 | inter-alpha-trypsin inhibitor heavy chain H4 isoform 2 precursor | 34.67 | 2 | 2 | 30 | 65 |
| 153945780 | inter-alpha-trypsin inhibitor heavy chain H5 isoform 1 | 40.79 | 3 | 3 | 33 | 74 |
| 289666750 | interleukin-34 isoform 2 precursor | 34.44 | 2 | 1 | 6 | 14 |
| 31317249 | interleukin-6 receptor subunit alpha isoform 2 precursor | 25.21 | 2 | 2 | 6 | 27 |
| 156231037 | kininogen-1 isoform 1 | 49.38 | 3 | 7 | 32 | 83 |
| 143770880 | laminin subunit beta-4 precursor | 31.57 | 1 | 1 | 41 | 58 |
| 13489087 | leukocyte elastase inhibitor | 52.24 | 2 | 2 | 19 | 37 |
| 33946291 | lysophosphatidylcholine acyltransferase 1 | 41.01 | 1 | 1 | 19 | 31 |
| 5729929 | matrix metalloproteinase-24 preproprotein | 36.43 | 1 | 1 | 23 | 37 |
| 74272287 | matrix metalloproteinase-9 preproprotein | 37.48 | 1 | 2 | 24 | 39 |
| 24415404 | midasin | 37.22 | 1 | 1 | 170 | 331 |
| 83367077 | mucin-16 | 21.37 | 1 | 2 | 182 | 366 |
| 145701025 | multiple epidermal growth factor-like domains protein 8 | 25.88 | 1 | 1 | 46 | 88 |
| 46049125 | myosin-binding protein C, slow-type isoform 2 | 49.13 | 4 | 1 | 57 | 101 |
| 4758754 | napsin-A preproprotein | 24.05 | 1 | 2 | 10 | 37 |
| 290656011 | neogenin isoform 2 precursor | 30.61 | 3 | 1 | 35 | 58 |

FIG. 14B-3

| Accession | Description | ΣCoverage | Σ# Proteins | Unique Peptid | Σ# Peptides | Σ# PSMs |
|---|---|---|---|---|---|---|
| 75709198 | nephronectin isoform B precursor | 52.21 | 1 | 1 | 23 | 55 |
| 94420689 | neural cell adhesion molecule 1 isoform 1 | 44.46 | 3 | 2 | 34 | 113 |
| 4557707 | neural cell adhesion molecule L1 isoform 1 precursor | 32.38 | 3 | 1 | 27 | 49 |
| 14211536 | neurexin-2-beta isoform alpha-1 precursor | 31.13 | 2 | 1 | 36 | 82 |
| 4503549 | neutrophil elastase preproprotein | 10.86 | 1 | 4 | 6 | 18 |
| 144226847 | obscurin-like protein 1 isoform 1 precursor | 39.19 | 3 | 1 | 55 | 116 |
| 52426787 | oligodendrocyte-myelin glycoprotein precursor | 46.82 | 1 | 1 | 13 | 23 |
| 171906559 | peripheral-type benzodiazepine receptor-associated protein 1 isoform a | 35.7 | 2 | 1 | 60 | 146 |
| 65301141 | PH domain leucine-rich repeat-containing protein phosphatase 2 | 29.86 | 1 | 1 | 26 | 48 |
| 334639929 | pikachurin isoform 1 | 42.32 | 2 | 1 | 26 | 78 |
| 4505881 | plasminogen isoform 1 precursor | 78.52 | 2 | 20 | 59 | 156 |
| 291190772 | platelet glycoprotein Ib alpha chain precursor | 33.28 | 1 | 1 | 13 | 68 |
| 59710104 | plexin-A3 precursor | 31.21 | 1 | 1 | 48 | 96 |
| 157738645 | plexin-A4 isoform 1 | 40.18 | 2 | 1 | 63 | 114 |
| 149363636 | plexin-B2 precursor | 42.55 | 1 | 1 | 59 | 109 |
| 169217550 | PREDICTED: similar to CNTNAP3 protein | 37.44 | 1 | 1 | 6 | 14 |
| 239755389 | PREDICTED: similar to UMBT1 isoform 2 | 26.96 | 5 | 1 | 26 | 68 |
| 260166672 | pro-neuregulin-2, membrane-bound isoform isoform 2 | 36.83 | 3 | 1 | 21 | 41 |
| 157653329 | procollagen C-endopeptidase enhancer 1 | 47.88 | 1 | 1 | 14 | 28 |
| 4506041 | prolargin precursor | 33.25 | 1 | 1 | 8 | 12 |
| 5031873 | protein ERGIC-53 precursor | 53.73 | 1 | 3 | 26 | 58 |
| 4503743 | protein flightless-1 homolog | 37.04 | 1 | 2 | 46 | 114 |
| 21704277 | protein jagged-2 isoform a precursor | 32.63 | 2 | 1 | 23 | 37 |
| 4506761 | protein S100-A10 | 68.04 | 1 | 1 | 6 | 27 |
| 5032057 | protein S100-A11 | 40.95 | 1 | 3 | 4 | 15 |
| 5174661 | protein S100-A2 | 25.77 | 1 | 1 | 2 | 4 |
| 4506765 | protein S100-A4 | 49.5 | 1 | 2 | 6 | 12 |
| 4506767 | protein S100-A5 | 71.82 | 1 | 1 | 10 | 22 |
| 21614544 | protein S100-A8 | 100 | 1 | 15 | 20 | 103 |
| 4505773 | protein S100-A9 | 96.49 | 1 | 11 | 15 | 62 |
| 5454034 | protein S100-B | 31.52 | 1 | 1 | 3 | 7 |
| 5174663 | protein S100-P | 86.32 | 1 | 1 | 6 | 18 |
| 39777597 | protein-glutamine gamma-glutamyltransferase 2 isoform a | 44.69 | 2 | 14 | 28 | 75 |
| 4507475 | protein-glutamine gamma-glutamyltransferase K | 37.94 | 1 | 1 | 19 | 52 |
| 223633965 | proteoglycan 3 precursor | 30.67 | 1 | 1 | 3 | 4 |
| 4503635 | prothrombin preproprotein | 46.62 | 1 | 2 | 19 | 39 |

FIG. 14B-4

| Accession | Description | Coverage | # Proteins | Unique Peptides | # Peptides | # PSMs |
|---|---|---|---|---|---|---|
| 1488826696 | pulmonary surfactant-associated protein A2 precursor | 84.27 | 5 | 2 | 13 | 24 |
| 288856299 | pulmonary surfactant-associated protein B precursor | 32.57 | 1 | 5 | 9 | 29 |
| 288815521 | pulmonary surfactant-associated protein C isoform 1 proprotein | 43.65 | 2 | 1 | 5 | 8 |
| 6912638 | ras suppressor protein 1 isoform 1 | 17.69 | 2 | 1 | 4 | 20 |
| 157952215 | receptor-type tyrosine-protein phosphatase beta isoform a | 40.72 | 2 | 1 | 62 | 131 |
| 13677214 | receptor-type tyrosine-protein phosphatase O isoform a precursor | 23.19 | 2 | 1 | 25 | 48 |
| 27436938 | reelin isoform a | 28.67 | 2 | 1 | 70 | 111 |
| 61888896 | roundabout homolog 2 isoform ROBO2b | 29.75 | 2 | 1 | 37 | 88 |
| 1884497703 | semaphorin-3F precursor | 46.11 | 1 | 1 | 31 | 104 |
| 324554741 | serpin H1 precursor | 53.83 | 1 | 4 | 19 | 43 |
| 617743980 | stabilin-2 precursor | 27.6 | 1 | 2 | 56 | 97 |
| 1503785552 | sushi domain-containing protein 5 precursor | 51.67 | 1 | 1 | 23 | 134 |
| 148886654 | sushi, von Willebrand factor type A, EGF and pentraxin domain-containing protein | 32.32 | 1 | 1 | 84 | 171 |
| 62988324 | tenascin-N precursor | 35.72 | 1 | 1 | 34 | 62 |
| 157384973 | tenascin-R precursor | 30.41 | 1 | 2 | 24 | 42 |
| 291045225 | titin isoform N2-A | 47.77 | 5 | 3 | 1374 | 3005 |
| 225547221 | toll-like protein 1 precursor | 56.07 | 1 | 1 | 41 | 66 |
| 222831592 | transmembrane protease serine 7 | 35.96 | 1 | 1 | 21 | 44 |
| 148746195 | trichohyalin | 77.87 | 1 | 1 | 231 | 470 |
| 56606114 | trichohyalin-like protein 1 | 63.83 | 1 | 1 | 41 | 130 |
| 471774859 | tripartite motif-containing protein 46 | 50.46 | 1 | 9 | 32 | 68 |
| 235510445 | tumor necrosis factor ligand superfamily member 15 | 32.67 | 1 | 7 | 4 | 9 |
| 21361116 | versican core protein isoform 1 precursor | 33.13 | 2 | 1 | 72 | 155 |
| 88853069 | vitronectin precursor | 45.61 | 1 | 12 | 20 | 68 |
| 541123390 | voltage-dependent calcium channel subunit alpha-2/delta-1 | 38.22 | 1 | 1 | 32 | 66 |
| 891191868 | von Willebrand factor preproprotein | 45.47 | 1 | 1 | 82 | 195 |
| 108863945 | X-ray repair cross-complementing protein 5 | 66.94 | 1 | 9 | 43 | 88 |
| 4503841 | X-ray repair cross-complementing protein 6 | 59.44 | 1 | 7 | 31 | 58 |
| 165979828 | zinc finger protein 91 homolog | 46.14 | 1 | 1 | 32 | 113 |

FIG. 14B-5

| Score A3 | Coverage A3 | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| 6.9664011 | 3.98 | 1 | 3 | 0 | 25.99 | 8 | 12 | 377 | 40.71120055 | 4.792480469 |
| 5.2731U5025 | 16.5 | 11 | 21 | 0 | 26.11 | 16 | 36 | 1103 | 120.7869201 | 7.942871094 |
| 0 | 31.74 | 30 | 58 | 0 | 17.5 | 19 | 36 | 1594 | 177.5601891 | 7.869628906 |
| 0 | 45.15 | 32 | 64 | 0 | 38.76 | 29 | 50 | 1205 | 135.4873797 | 7.151855469 |
| 1.670731306 | 23.23 | 19 | 27 | 0 | 20.12 | 14 | 29 | 1156 | 130.8470018 | 5.109853281 |
| 0 | 5.92 | 8 | 10 | 96.3490802 | 13.37 | 22 | 76 | 2431 | 250.2195771 | 4.081542969 |
| 0 | 27.42 | 7 | 7 | 6.869538784 | 54.37 | 11 | 19 | 423 | 47.62053863 | 5.516113281 |
| 28.47131586 | 26.79 | 11 | 25 | 130.7264581 | 46.65 | 19 | 70 | 418 | 46.7070216 | 5.592285156 |
| 0 | 12.02 | 4 | 8 | 4.244415998 | 21.79 | 9 | 23 | 491 | 54.53106782 | 6.290527344 |
| 0 | 16.89 | 4 | 8 | 31.0650661 | 19.07 | 5 | 17 | 367 | 39.31568933 | 5.719238281 |
| 1.618932247 | 13.77 | 13 | 21 | 255.5322193 | 31.07 | 38 | 126 | 1474 | 163.1888824 | 6.417480469 |
| 0 | 8.25 | 3 | 10 | 5.408443928 | 2.47 | 1 | 2 | 485 | 53.12051722 | 6.315917969 |
| 34.1869U3 | 47.98 | 14 | 24 | 129.0306336 | 73.41 | 26 | 84 | 346 | 38.699998096 | 7.020019531 |
| 77.29801667 | 73.95 | 28 | 60 | 37.85685873 | 57.7 | 21 | 44 | 357 | 40.38571944 | 8.367675781 |
| 8.903194666 | 35.94 | 7 | 11 | 8.479953647 | 47.81 | 13 | 22 | 320 | 35.91440263 | 5.046386719 |
| 4.183316708 | 31.33 | 18 | 26 | 17.50332046 | 35.23 | 18 | 27 | 667 | 75.22922269 | 5.668457031 |
| 0 | 73.48 | 7 | 8 | 46.62476397 | 51.52 | 13 | 43 | 132 | 14.3159097 | 8.748535156 |
| 0 | 36.64 | 14 | 25 | 25.9147644 | 20.26 | 12 | 37 | 464 | 52.56886678 | 6.712402344 |
| 0 | 27.01 | 6 | 11 | 0 | 28.94 | 7 | 16 | 311 | 35.1690475 | 6.354003906 |
| 77.54534507 | 25.06 | 30 | 67 | 0 | 23.24 | 26 | 51 | 1704 | 191.23894U6 | 7.620605469 |
| 0 | 42.63 | 6 | 8 | 6.205634952 | 45.42 | 5 | 69 | 251 | 26.86885633 | 9.495605469 |
| 5.403406262 | 18.04 | 49 | 76 | 1.811958075 | 14.6 | 37 | 64 | 4391 | 468.532495 | 6.507324219 |
| 5.567186832 | 11.88 | 3 | 5 | 52.18475342 | 46.09 | 9 | 18 | 345 | 38.27266101 | 7.972157969 |
| 0 | 13.59 | 3 | 3 | 15.32447207 | 34.24 | 10 | 21 | 368 | 41.627539 | 7.518066406 |
| 21.92990816 | 58.11 | 10 | 22 | 2.182327509 | 23.42 | 6 | 11 | 222 | 25.169925829 | 6.756347656 |
| 0 | 40 | 10 | 20 | 0 | 36 | 6 | 11 | 325 | 35.25846284 | 5.376464844 |
| 0 | 57.45 | 4 | 7 | 1.722420335 | 67.02 | 7 | 13 | 94 | 10.357566323 | 9.891113281 |
| 0 | 33.17 | 11 | 22 | 131.7302102 | 57.62 | 31 | 118 | 597 | 66.98933987 | 7.298339844 |
| | | | | 3.358926654 | 29.08 | 7 | 18 | 251 | 28.26740693 | 5.135253906 |
| 14.32770551 | 21.23 | 43 | 85 | 7.288565874 | 26.51 | 49 | 98 | 3014 | 329.278012 | 5.922363281 |
| 0 | 11.01 | 3 | 3 | 12.23845971 | 13.21 | 5 | 16 | 545 | 60.546174455 | 6.100097656 |
| 7.458164692 | 17.11 | 5 | 10 | 0 | 17.4 | 3 | 3 | 339 | 37.7968366 | 6.303222656 |
| 19.32747066 | 31.55 | 8 | 16 | 0 | 21.6 | 5 | 7 | 412 | 44.523627B2 | 6.536621094 |
| 8.3104918 | 48.24 | 7 | 13 | 49.93545651 | 55.69 | 15 | 32 | 255 | 28.819070% | 11.194824272 |
| 0 | 34.63 | 4 | 11 | 0 | 20 | 2 | 2 | 205 | 21.50713119 | 7.107910156 |
| 16.49222851 | 42.91 | 8 | 25 | 0 | 25.91 | 3 | 6 | 247 | 27.30718899 | 9.290527344 |

FIG. 14B-6

| Score A3 | Coverage A3 | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| 9.514135361 | 30.19 | 24 | 42 | 77.16472542 | 42.76 | 32 | 78 | 1464 | 138.3265682 | 5.795410156 |
| 0 | 35.33 | 27 | 54 | 58.55963576 | 36.04 | 37 | 98 | 1418 | 134.3073123 | 8.558105469 |
| 0 | 20.4 | 22 | 35 | 14.95946062 | 48.91 | 38 | 72 | 1466 | 138.4699793 | 6.565917969 |
| 0 | 21.39 | 21 | 46 | 5.956876516 | 22.11 | 21 | 26 | 1669 | 160.5140635 | 8.279785156 |
| 0 | 24.27 | 30 | 80 | 4.848987103 | 32.26 | 45 | 175 | 1838 | 183.4470677 | 5.059082031 |
| 3.785479546 | 32.98 | 22 | 27 | 21.32942605 | 40.95 | 24 | 47 | 1028 | 108.4620167 | 5.427246094 |
| 0 | 32.64 | 60 | 104 | 1.747853637 | 33.97 | 62 | 116 | 2944 | 295.0409593 | 6.265136719 |
| 3.804440557 | 24.77 | 18 | 31 | 0 | 21.26 | 15 | 26 | 1284 | 135.7459487 | 8.060058594 |
| 0 | 26.06 | 22 | 41 | 30.62125671 | 24.96 | 22 | 61 | 1366 | 129.2354507 | 8.953613281 |
| 0 | 25.08 | 23 | 66 | 16.03302801 | 36.36 | 35 | 73 | 1499 | 144.8209834 | 6.455566406 |
| 0 | 41.71 | 25 | 36 | 5.453642368 | 49.68 | 26 | 55 | 1019 | 108.5119406 | 6.214355469 |
| 2.194773674 | 30.05 | 28 | 85 | 0 | 37.87 | 37 | 107 | 1637 | 158.250777 | 9.261230469 |
| 6.759282827 | 30.47 | 57 | 96 | 59.80528617 | 28.42 | 60 | 135 | 3177 | 343.4567885 | 6.683105469 |
| 11.99485576 | 25.89 | 44 | 99 | 0 | 33.45 | 52 | 94 | 2263 | 247.0187659 | 6.888183594 |
| 17.32131732 | 26.48 | 5 | 11 | 27.67 | 6 | 12 | 253 | 26.70448984 | 8.631347656 |
| 5.558405995 | 34.69 | 5 | 11 | 8.98 | 2 | 4 | 245 | 25.75713927 | 8.411621094 |
| 20.08009923 | 13.65 | 22 | 33 | 118.4691755 | 42.93 | 54 | 124 | 1663 | 187.0298837 | 6.404785156 |
| 1.725845456 | 22.19 | 34 | 74 | 27.11644125 | 25.75 | 29 | 49 | 1744 | 192.6305508 | 7.269042969 |
| 0 | 16.88 | 11 | 17 | 104.1001482 | 45.81 | 29 | 79 | 764 | 85.47852807 | 7.063964844 |
| 6.924746871 | 38.67 | 33 | 54 | 95.28834901 | 40.45 | 36 | 74 | 1231 | 138.9786994 | 6.624511719 |
| 1.846983671 | 47.58 | 10 | 17 | 0 | 45.45 | 11 | 26 | 330 | 37.62596515 | 7.386230469 |
| 12.52368498 | 18.77 | 13 | 16 | 0 | 19.46 | 10 | 13 | 1007 | 111.7962892 | 5.770019531 |
| 3.569323182 | 24.28 | 23 | 73 | 0 | 23.63 | 19 | 25 | 1384 | 156.1671233 | 7.049316406 |
| 4.983943701 | 24.77 | 10 | 16 | 29.03650498 | 34.64 | 12 | 20 | 537 | 60.09212974 | 5.846191406 |
| 0 | 12.1 | 25 | 46 | 0 | 15.8 | 28 | 77 | 3487 | 379.7959316 | 6.087402344 |
| 21.51176548 | 45.92 | 3 | 13 | 15.0443244 | 18.37 | 2 | 6 | 98 | 11.13259139 | 7.562011719 |
| 7.189487934 | 30.64 | 12 | 24 | 33.36000383 | 24.79 | 11 | 32 | 359 | 39.72184112 | 8.543457031 |
| 0 | 34.14 | 19 | 57 | 0 | 36.92 | 12 | 63 | 539 | 59.15886277 | 8.528808594 |
| 5.562002921 | 22.45 | 10 | 17 | 7.211915327 | 30.55 | 15 | 22 | 766 | 82.59565759 | 7.723144531 |
| 0 | 21.98 | 12 | 23 | 0 | 21.39 | 11 | 22 | 828 | 90.42302375 | 8.367675781 |
| 6.682852745 | 10.84 | 27 | 46 | 6.98095715 | 17.97 | 45 | 72 | 4012 | 443.3499945 | 5.592285156 |
| 0 | 15.05 | 24 | 45 | 191.9979559 | 31.03 | 61 | 155 | 2871 | 312.0825498 | 4.932128906 |
| 60.12814283 | 34.76 | 28 | 65 | 337.2498391 | 52.08 | 60 | 287 | 866 | 94.91441918 | 6.011230469 |
| 82.82210624 | 40.12 | 19 | 50 | 356.4803872 | 70.47 | 39 | 214 | 491 | 55.89226326 | 8.265136719 |
| 102.6261419 | 56.06 | 23 | 90 | 396.6145331 | 82.38 | 38 | 154 | 437 | 49.46497326 | 6.087402344 |
| 269.7370447 | 29.46 | 42 | 118 | 89.6403091 | 29.86 | 39 | 80 | 2176 | 239.4857667 | 5.884277344 |

FIG. 14B-7

| Score A3 | Coverage A3 | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| 0 | 9.28 | 11 | 17 | 0 | 24.68 | 30 | 50 | 2391 | 247.9278232 | 8.309082031 |
| 32.07286894 | 25.58 | 50 | 127 | 3.34709537 | 35.52 | 65 | 170 | 2725 | 290.8406019 | 5.973144531 |
| 0 | 14.67 | 32 | 48 | 0 | 16.6 | 36 | 93 | 3169 | 350.9372492 | 5.033691406 |
| 3.950715019 | 14.4 | 23 | 51 | 0 | 17.77 | 24 | 34 | 2139 | 238.0308048 | 5.325683594 |
| 7.931457295 | 31.85 | 4 | 7 | | | | | 135 | 14.70620005 | 5.503417969 |
| 10.40904772 | 25.2 | 5 | 11 | 1.900822894 | 10 | 3 | 5 | 250 | 26.1360544 | 8.558105469 |
| 0 | 25.74 | 1 | 1 | 6.493913412 | 18.38 | 2 | 3 | 136 | 15.05580063 | 7.620605469 |
| 11.88544941 | 28.48 | 5 | 10 | 0 | 27.55 | 5 | 17 | 323 | 35.86491481 | 8.133300781 |
| 47.98008347 | 28.57 | 10 | 87 | 1.723752737 | 31.82 | 10 | 29 | 308 | 34.11875694 | 9.656738281 |
| 0 | 43.27 | 9 | 9 | 0 | 46.67 | 10 | 22 | 375 | 42.72249712 | 6.756347656 |
| 2.507554293 | 17.78 | 67 | 128 | 0 | 15.55 | 52 | 79 | 5635 | 613.0013386 | 6.493652344 |
| 0 | 32.47 | 9 | 15 | 24.24825263 | 33.33 | 9 | 29 | 462 | 51.64327527 | 7.020019531 |
| 0 | 10.29 | 6 | 12 | 16.20346488 | 17.9 | 10 | 27 | 525 | 59.54087001 | 7.503417969 |
| 13.51506805 | 31.03 | 5 | 7 | 0 | 35.78 | 5 | 8 | 232 | 26.38140791 | 9.144042969 |
| 0 | 29.1 | 9 | 20 | 12.82957566 | 25.42 | 11 | 30 | 354 | 40.13998758 | 7.415527344 |
| 3.982647777 | 40.24 | 89 | 162 | 1.63055563 | 43.77 | 96 | 210 | 3708 | 383.5662962 | 5.985839844 |
| 0 | 21.13 | 4 | 10 | 0 | 65.73 | 10 | 16 | 213 | 24.84386744 | 9.671386719 |
| 0 | 25.06 | 18 | 39 | 0 | 28.49 | 18 | 42 | 874 | 98.92471048 | 8.675292969 |
| 0 | 10.65 | 8 | 18 | 10.14824152 | 22.94 | 16 | 33 | 911 | 101.3256195 | 6.785644531 |
| 0 | 16.49 | 13 | 20 | 23.54301262 | 20.61 | 13 | 21 | 946 | 106.396614 | 6.858886719 |
| 0 | 16.11 | 13 | 22 | 18.08323836 | 27.22 | 19 | 43 | 900 | 99.79517865 | 6.468261719 |
| 0 | 22.07 | 16 | 29 | 0 | 31.49 | 21 | 45 | 956 | 106.0113047 | 8.279785156 |
| 6.196876407 | 7.05 | 2 | 4 | 0 | 28.22 | 4 | 10 | 241 | 27.35600832 | 7.210449219 |
| 0 | 10.41 | 2 | 4 | 0 | 17.53 | 5 | 23 | 365 | 40.2119235 | 7.957519531 |
| 0 | 15.06 | 10 | 24 | 45.40213299 | 47.67 | 25 | 59 | 644 | 71.91215384 | 6.814941406 |
| 0 | 18.8 | 21 | 25 | 0 | 16.92 | 20 | 33 | 1761 | 193.4134246 | 6.354003906 |
| 0 | 15.04 | 6 | 7 | 25.26441479 | 45.38 | 14 | 30 | 379 | 42.71470438 | 6.277832031 |
| 8.662944555 | 28.28 | 11 | 18 | 0 | 23.22 | 8 | 13 | 534 | 59.11338865 | 6.023925781 |
| 0 | 23.57 | 13 | 24 | 18.5114131 | 21.71 | 10 | 13 | 645 | 73.18524745 | 9.231933594 |
| 0 | 28.29 | 16 | 24 | 5.125160098 | 16.83 | 8 | 15 | 707 | 78.40836009 | 6.062011719 |
| 0 | 20.71 | 85 | 151 | 5.496673465 | 24.5 | 96 | 180 | 5596 | 632.4201854 | 5.681152344 |
| 7.178739429 | 10.82 | 93 | 144 | 1.631752968 | 14.56 | 115 | 222 | 14507 | 1518.242261 | 5.262207031 |
| 6.139918089 | 13.21 | 21 | 47 | 4.066895962 | 15.33 | 25 | 41 | 2778 | 295.7398363 | 6.858886719 |
| 0 | 27.18 | 25 | 34 | 0 | 37.98 | 39 | 67 | 1148 | 128.3971036 | 6.036621094 |
| 38.8145709 | 14.05 | 6 | 17 | 0 | 19.05 | 6 | 20 | 420 | 45.35778156 | 6.609863281 |
| 0 | 18.47 | 20 | 33 | 0 | 19.53 | 17 | 25 | 1408 | 154.2068688 | 6.417480469 |

FIG. 14B-8

| Score A3 | Coverage A3 | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| 10.42382479 | 34.34 | 13 | 26 | 7.1254704 | 27.43 | 11 | 29 | 565 | 61.86620211 | 8.338378906 |
| 11.97596157 | 30.9 | 17 | 70 | 1.649810672 | 28.42 | 20 | 43 | 848 | 93.30256547 | 4.868652344 |
| 0 | 17.26 | 15 | 23 | 6.651116729 | 19.65 | 14 | 26 | 1257 | 139.9153013 | 6.239746094 |
| 1.840133429 | 17.41 | 18 | 40 | 0 | 21.32 | 22 | 42 | 1712 | 184.865379 | 5.922363281 |
| 0 | 7.12 | 2 | 4 | 22.06102347 | 10.86 | 5 | 14 | 267 | 28.49978994 | 9.349121094 |
| 0 | 18.67 | 22 | 47 | 1.636407852 | 31.96 | 41 | 69 | 1896 | 206.817256 | 5.530371094 |
| 12.49504519 | 30.23 | 7 | 12 | 0 | 39.09 | 8 | 11 | 440 | 49.57624682 | 7.942871094 |
| 4.025540233 | 18.36 | 25 | 43 | 5.428351879 | 25.85 | 40 | 103 | 1857 | 199.9276902 | 5.109863281 |
| 0 | 11.56 | 11 | 20 | 0 | 25.09 | 19 | 28 | 1323 | 146.6579802 | 5.706542969 |
| 0 | 28.34 | 14 | 38 | 0 | 25.97 | 16 | 40 | 1009 | 110.2731796 | 7.503417969 |
| 0 | 42.72 | 18 | 22 | 126.0115997 | 70.49 | 44 | 134 | 810 | 90.510161 | 7.239746094 |
| 0 | 18.56 | 6 | 8 | 11.07431626 | 18.25 | 8 | 60 | 652 | 71.49518308 | 6.290527344 |
| 0 | 23.41 | 32 | 63 | 0 | 17.05 | 20 | 33 | 1871 | 207.5703818 | 7.312988281 |
| 3.481318593 | 27.3 | 38 | 62 | 0 | 24.39 | 29 | 52 | 1394 | 212.3180597 | 6.358886719 |
| 1.633317709 | 24.27 | 30 | 52 | 3.239178658 | 29.16 | 33 | 57 | 1839 | 204.9971883 | 6.239746094 |
| 0 | 27.59 | 4 | 6 | 0 | 31.03 | 4 | 8 | 203 | 23.17782112 | 6.800292969 |
| 13.44215775 | 18.01 | 16 | 38 | 0 | 14.37 | 13 | 30 | 1788 | 194.3459074 | 5.516113281 |
| 3.910223842 | 9.06 | 5 | 10 | 0 | 36.12 | 18 | 31 | 695 | 74.88208017 | 7.579199219 |
| 0 | 35.41 | 9 | 16 | 3.502057433 | 26.28 | 7 | 12 | 449 | 47.94198248 | 7.430175781 |
| 0 | 11.52 | 2 | 2 | 15.75886297 | 21.73 | 6 | 10 | 382 | 43.78215718 | 9.378417969 |
| 19.60959399 | 24.12 | 14 | 28 | 1.644983768 | 42.55 | 14 | 30 | 510 | 57.51298392 | 6.770996094 |
| 16.34655833 | 26.87 | 28 | 51 | 3.296899676 | 22.7 | 24 | 63 | 1269 | 144.6595016 | 6.049316406 |
| 0 | 24.23 | 13 | 25 | 4.527997017 | 13 | 10 | 12 | 1238 | 133.2772419 | 5.833496094 |
| 3.926550269 | 35.05 | 3 | 9 | 0 | 38.14 | 3 | 18 | 97 | 11.19551181 | 7.371582031 |
| 9.101034164 | 19.05 | 2 | 10 | 10.21724892 | 30.48 | 3 | 5 | 105 | 11.73282564 | 7.125585938 |
| | | | | 3.907156825 | 25.77 | 2 | 4 | 97 | 10.97831527 | 4.779785156 |
| 13.30409658 | 49.5 | 6 | 11 | 0 | 10.89 | 6 | 1 | 101 | 11.72073264 | 6.127929688 |
| 0 | 41.82 | 7 | 10 | 0 | 71.82 | 6 | 12 | 110 | 12.80432776 | 5.516113281 |
| 9.737903833 | 41.94 | 2 | 4 | 120.6826272 | 100 | 19 | 99 | 93 | 10.82764968 | 7.034667969 |
| 8.533324957 | 33.33 | 2 | 4 | 86.52929592 | 96.49 | 14 | 58 | 114 | 13.23350884 | 6.125488281 |
| 9.501650095 | 31.52 | 3 | 7 | 0 | | | | 92 | 10.70605026 | 4.589355469 |
| 0 | 18.95 | 2 | 5 | 9.878676534 | 75.79 | 5 | 13 | 95 | 10.39322299 | 4.881347656 |
| 94.66105688 | 39.74 | 23 | 57 | 18.49743414 | 21.98 | 10 | 18 | 687 | 77.27967272 | 5.224121094 |
| 0 | 16.16 | 8 | 14 | 0 | 24.97 | 13 | 38 | 817 | 89.73032002 | 6.036621094 |
| 0 | 25.78 | 2 | 2 | 5.195752382 | 4.89 | 1 | 2 | 225 | 25.38801206 | 4.805175781 |
| 3.390694141 | 25.24 | 10 | 22 | 4.176883936 | 26.69 | 9 | 17 | 622 | 69.99212719 | 5.896972656 |

FIG. 14B-9

| Score A3 | Coverage A3 | # Peptides A3 | # PSM A3 | Score B3 | Coverage B3 | # Peptides B3 | # PSM B3 | # AAs | MW [kDa] | calc. pI |
|---|---|---|---|---|---|---|---|---|---|---|
| 29.24680471 | 25.4 | 4 | 12 | 0 | 57.34 | 9 | 12 | 248 | 26.15262314 | 5.173339844 |
| 72.08524275 | 22.39 | 7 | 23 | 0 | 12.47 | 2 | 6 | 393 | 43.31744204 | 5.744628906 |
| 9.204756021 | 32.99 | 4 | 7 | 0 | 10.66 | 1 | 1 | 197 | 20.998847 | 6.653808594 |
| 0 | 10.83 | 3 | 12 | 0 | 10.47 | 2 | 8 | 277 | 31.52069322 | 8.645996094 |
| 0 | 19.73 | 31 | 65 | 1.914222121 | 26.82 | 36 | 66 | 2215 | 248.9878597 | 7.737792969 |
| 0 | 13.16 | 13 | 24 | 11.59187293 | 13.73 | 12 | 24 | 1216 | 138.255277 | 6.011230469 |
| 7.919072866 | 15.23 | 33 | 47 | 0 | 18.61 | 40 | 64 | 3460 | 388.1374684 | 5.884277344 |
| 17.60946679 | 17.13 | 19 | 40 | 5.681710124 | 20.39 | 21 | 48 | 1378 | 151.1059654 | 6.328613281 |
| 2.237589836 | 38.47 | 22 | 92 | 0 | 21.91 | 9 | 12 | 785 | 88.32514956 | 8.265136719 |
| 20.53966141 | 32.54 | 10 | 15 | 0 | 46.89 | 14 | 28 | 418 | 46.41117943 | 8.689941406 |
| 1.638636647 | 16.03 | 26 | 45 | 0 | 17.37 | 32 | 52 | 2551 | 276.8050706 | 6.404785156 |
| 0 | 23.69 | 11 | 33 | 3.758301854 | 39.11 | 14 | 101 | 629 | 67.97846011 | 4.906738281 |
| 2.485155344 | 16.27 | 39 | 76 | 0 | 23.69 | 52 | 95 | 3571 | 389.91249923 | 5.503417969 |
| 0 | 22.02 | 19 | 37 | 4.820616007 | 23.86 | 17 | 25 | 1299 | 143.943561 | 5.630371094 |
| 11.67954707 | 15.1 | 12 | 20 | 0 | 18.92 | 14 | 22 | 1358 | 149.4674696 | 4.817871094 |
| 53.10939311 | 29.13 | 736 | 1403 | 37.6324532 | 31.76 | 764 | 1602 | 33423 | 3711.285507 | 6.521972656 |
| 1.695175886 | 34.25 | 19 | 35 | 0 | 39.09 | 25 | 31 | 1013 | 114.635188 | 6.023925781 |
| 0 | 23.43 | 13 | 24 | 0 | 20.22 | 10 | 20 | 717 | 80.30156814 | 7.810035156 |
| 14.05721903 | 60.73 | 132 | 232 | 6.201214075 | 54.14 | 118 | 238 | 1943 | 253.7769247 | 5.782714844 |
| 0 | 43.69 | 23 | 67 | 4.209026814 | 52.43 | 27 | 63 | 904 | 99.21561803 | 4.690917969 |
| 3.471545815 | 29.51 | 16 | 30 | 4.977783203 | 31.75 | 18 | 38 | 759 | 83.37020704 | 7.723144531 |
| 0 | 22.17 | 39 | 74 | 0 | 32.67 | 4 | 9 | 251 | 28.069067559 | 6.770996094 |
| 22.54521561 | 28.45 | 9 | 16 | 108.9027236 | 17.2 | 38 | 81 | 3396 | 372.5895531 | 4.513183594 |
| 3.468973756 | 15.31 | 14 | 26 | 0 | 29.29 | 12 | 52 | 478 | 54.27117094 | 5.795410156 |
| 8.704805136 | 24.32 | 40 | 94 | 0 | 32.26 | 21 | 40 | 1091 | 123.105685 | 5.249511719 |
| 28.47653167 | 38.93 | 23 | 45 | 32.75443721 | 29.33 | 52 | 101 | 2813 | 309.0859734 | 5.490722656 |
| 32.38149357 | 28.24 | 15 | 25 | 40.69250202 | 49.32 | 21 | 43 | 732 | 82.65227975 | 5.808105469 |
| 5.051135417 | 31.05 | 14 | 32 | 0 | 42.04 | 18 | 33 | 609 | 69.79905748 | 6.639160156 |
|  |  |  |  | 0 | 41.05 | 24 | 81 | 570 | 63.40574737 | 7.356933594 |

FIG. 14B-10

| Accession | Description | ΣCoverage | Σ# Proteins | Σ# Unique Peptides | Σ# Peptides | Σ# PSMs | Score A3 | Coverage A3 | # Peptides A3 |
|---|---|---|---|---|---|---|---|---|---|
| 109715837 | fibronectin type-III domain-containing protein C4orf31 precur | 55.99 | 1 | 1 | 23 | 60 | 0 | 38.91 | 15 |
| 115529482 | neural cell adhesion molecule 1 isoform 2 | 60.49 | 3 | 5 | 39 | 128 | 50.6276052 | 46.62 | 26 |
| 13699830 | matrilin-4 isoform 1 precursor | 34.42 | 3 | 1 | 16 | 44 | 2.24397779 | 25.47 | 11 |
| 144226847 | obscurin-like protein 1 isoform 1 precursor | 53.96 | 3 | 1 | 69 | 141 | 2.00060964 | 25.21 | 36 |
| 157384973 | tenascin-R precursor | 28.57 | 1 | 8 | 25 | 67 | 24.9678578 | 13.62 | 14 |
| 21361116 | versican core protein isoform 1 precursor | 32.42 | 4 | 3 | 66 | 209 | 48.8066466 | 18.96 | 33 |
| 28373119 | contactin-1 isoform 2 precursor | 56.31 | 2 | 6 | 34 | 92 | 66.5399318 | 45.08 | 24 |
| 34577057 | leucine-rich repeat transmembrane protein FLRT1 | 29.67 | 1 | 1 | 13 | 126 | 0 | 17.95 | 7 |
| 4502107 | annexin A5 | 56.25 | 1 | 1 | 12 | 25 | 5.30683863 | 14.69 | 3 |
| 4504981 | galectin-1 | 39.26 | 1 | 3 | 3 | 8 | 2.15962958 | 11.11 | 1 |
| 52426787 | oligodendrocyte-myelin glycoprotein precursor | 30.91 | 1 | 3 | 11 | 38 | 28.2832336 | 26.59 | 9 |
| 54112390 | voltage-dependent calcium channel subunit alpha-2/delta-1 | 36.21 | 1 | 1 | 31 | 118 | 1.92075646 | 22.73 | 18 |
| 54554034 | protein S100-B | 60.87 | 1 | 2 | 5 | 37 | 0 | 51.09 | 3 |
| 617431980 | stabilin-2 precursor | 30.97 | 1 | 1 | 54 | 139 | 0 | 19.8 | 30 |
| 618352232 | growth/differentiation factor 7 preproprotein | 59.56 | 1 | 1 | 19 | 104 | 1.816475715 | 50.44 | 13 |
| 71773415 | annexin A6 isoform 2 | 67.47 | 2 | 1 | 34 | 95 | 0 | 41.38 | 18 |
| 7656993 | capsine-7 isoform b | 57.19 | 1 | 1 | 18 | 77 | 10.0424988 | 23.06 | 7 |
| 7669526 | pro-neuregulin-1, membrane-bound isoform isoform HRG-alp | 47.81 | 11 | 1 | 24 | 75 | 0 | 28.28 | 14 |
| 89903008 | neurofascin isoform 4 precursor | 49.44 | 4 | 1 | 44 | 176 | 5.36729097 | 35.84 | 24 |
| 93102379 | low-density lipoprotein receptor-related protein 16 precursor | 37.44 | 1 | 1 | 107 | 439 | 8.38965179 | 26.09 | 67 |

FIG. 14C-1

| # PSM A3 | Score B3 | Coverage B3 | Peptides B3 | # PSM B3 | # AAs | MW [kDa] | calc. pI | |
|---|---|---|---|---|---|---|---|---|
| 32 | 0 | 45.95 | 13 | 28 | 568 | 64.6322897 | 8.93896484 | fibronectin type-III domain-containing protein C4orf31 precursor |
| 58 | 69.0054445 | 46.15 | 28 | 70 | 858 | 94.5151543 | 4.86865234 | neural cell adhesion molecule 1 isoform 2 |
| 19 | 2.43792796 | 24.96 | 8 | 25 | 581 | 64.065833 | 5.89697266 | matrilin-4 isoform 1 precursor |
| 49 | 5.99757969 | 46.99 | 53 | 92 | 1896 | 206.817256 | 5.630371.09 | obscurin-like protein 1 isoform 1 precursor |
| 23 | 103.803779 | 26.36 | 19 | 44 | 1358 | 149.46747 | 4.81787109 | tenascin-R precursor |
| 79 | 52.2154819 | 28.59 | 56 | 130 | 3396 | 372.589553 | 4.51318359 | versican core protein isoform 1 precursor |
| 47 | 44.4953159 | 44.59 | 26 | 45 | 1007 | 111.796289 | 5.77001953 | contactin-1 isoform 2 precursor |
| 23 | 15.0367639 | 27.6 | 9 | 103 | 674 | 74.0408629 | 6.44287109 | leucine-rich repeat transmembrane protein FLRT1 |
| 9 | 3.11222529 | 50.63 | 10 | 16 | 320 | 35.9144026 | 5.04638672 | annexin A5 |
| 3 | 2.71182299 | 39.26 | 5 | 5 | 135 | 14.7062001 | 5.50341797 | galectin-1 |
| 23 | 9.42200136 | 28.64 | 9 | 15 | 440 | 49.5762468 | 7.94287109 | oligodendrocyte-myelin glycoprotein precursor |
| 56 | 10.4833395 | 29.06 | 25 | 62 | 1091 | 123.105685 | 5.24951172 | voltage-dependent calcium channel subunit alpha-2/delta-1 |
| 4 | 45.2343469 | 50 | 4 | 33 | 92 | 10.7060503 | 4.89935547 | protein S100-B |
| 62 | 0 | 22.97 | 33 | 77 | 2551 | 276.805071 | 6.40478516 | stabilin-2 precursor |
| 63 | 1.66706216 | 30.67 | 10 | 41 | 450 | 46.9210196 | 9.80322266 | growth/differentiation factor 7 preproprotein |
| 36 | 3.11106801 | 57.57 | 28 | 59 | 667 | 75.2292269 | 5.66845703 | annexin A6 isoform 2 |
| 32 | 0 | 53.55 | 15 | 45 | 633 | 70.2491807 | 6.37939453 | copine-7 isoform b |
| 30 | 0 | 39.22 | 17 | 45 | 540 | 70.347894 | 8.79248047 | pro-neuregulin-1, membrane-bound isoform isoform HRG-alpha |
| 79 | 6.21705365 | 36.01 | 30 | 97 | 1169 | 131.586266 | 6.87353516 | neurofascin isoform 4 precursor |
| 242 | 3.99518871 | 25.94 | 66 | 197 | 4599 | 515.159397 | 5.30029297 | low-density lipoprotein receptor-related protein 1B precursor |

FIG. 14C-2

● 4-arm 2K   ● 4-arm 10K   ● 4-arm 20K

● 8-arm 20K   ● 4-arm 20K

● DMSO ● PBS, pH 7.4

| Matrix | RGD |
| Laminin G | Thrombospondin |

| Tenascin C | Laminin Beta
| Osteopontin

Brain

| Protein | Peptide | % Brain |
|---|---|---|
| COL I | DGEA | 9% |
| COL1A2 | FYDLR | 11% |
| COL IV | | |
| COL4A2 | IKVAV | 7% |
| LAMA | | |
| LAMA5 | YIGSR | 9% |
| LAMB | LRE | 5% |
| LAMB4 | PHSRN-RGD | 5% |
| LAMC | ALMKYHLNTLQCSE | 7% |
| FN | VTCG | 5% |
| POSTN | TWSKVGGHLRPGIVQSG | 2% |
| THSB | GPR | 3% |
| HSPG2 | GWTVFQKRLDGS | 3% |
| FGA | IVRRADRAAVP | 2% |
| FGG | GRKRK | 2% |
| COL XVIII | | |
| ELN | | |
| THSB | | |
| NFASC | | |
| FBN | | |
| VTN | | |
| VWF | | |
| TNX | | |
| COL VI | RGD | 30% |
| COL6A2 | | |
| COL6A3 | | |

FIG. 19A

Lung

| | |
|---|---|
| Lung | |
| Collagen, type I, alpha 1 | GFOGER, DGEA |
| Collagen, type I, alpha 2 | GFOGER, DGEA |
| Collagen, type IV, alpha 1 | FYFDLR |
| Collagen, type IX, alpha 3 | GFOGER |
| Fibronectin | PHSRN, RGD, LDV, IDA, LDA |
| Laminin, alpha 1 | IKVAV |
| Laminin, beta 1 | YIGSR, PDSGR, RYVVLPR |
| Laminin, beta 2 | LRE |
| Nidogen-1 / Enactin | SIGFRGDTC |
| Nephronectin | RGD/FEI |
| Thrombospondin 1 | RGD, FQGVLQNVRFVF, VTXG |
| Von Willebrand Factor | RGD |
| Tenascin C | AEIDGIEL (IDG), DLXXL |
| Elastin | VGVAPG, GRKRK |

FIG. 19B

SEQUENCE LISTING

<160> NUMBER OF SEQ ID NOS: 74

<210> SEQ ID NO 1
<211> LENGTH: 7
<212> TYPE: PRT
<213> ORGANISM: Artificial Sequence
<220> FEATURE:
<223> OTHER INFORMATION: A synthetic peptide sequence

<400> SEQUENCE: 1

Gly Cys Gly Asp Gly Glu Ala
1               5

<210> SEQ ID NO 2
<211> LENGTH: 6
<212> TYPE: PRT
<213> ORGANISM: Artificial Sequence
<220> FEATURE:
<223> OTHER INFORMATION: A synthetic peptide sequence

<400> SEQUENCE: 2

Gly Pro Arg Gly Gly Cys
1               5

<210> SEQ ID NO 3
<211> LENGTH: 18
<212> TYPE: PRT
<213> ORGANISM: Artificial Sequence
<220> FEATURE:
<223> OTHER INFORMATION: A synthetic peptide sequence

<400> SEQUENCE: 3

Cys Ser Arg Ala Arg Lys Gln Ala Ala Ser Ile Lys Val Ala Val Ala
1               5                   10                  15

Asp Arg

<210> SEQ ID NO 4
<211> LENGTH: 6
<212> TYPE: PRT
<213> ORGANISM: Artificial Sequence
<220> FEATURE:
<223> OTHER INFORMATION: A synthetic peptide sequence

<400> SEQUENCE: 4

Cys Ser Val Thr Cys Gly
1               5

<210> SEQ ID NO 5
<211> LENGTH: 22
<212> TYPE: PRT
<213> ORGANISM: Artificial Sequence
<220> FEATURE:
<223> OTHER INFORMATION: A synthetic peptide sequence

<400> SEQUENCE: 5

Cys Gly Gly Tyr Ser Met Lys Lys Thr Thr Met Lys Ile Ile Pro Phe
1               5                   10                  15

Asn Arg Leu Thr Ile Gly
            20

<210> SEQ ID NO 6
<211> LENGTH: 8
<212> TYPE: PRT
<213> ORGANISM: Artificial Sequence
<220> FEATURE:
<223> OTHER INFORMATION: A synthetic peptide sequence -continued

```
<400> SEQUENCE: 6

Gly Cys Lys Gln Leu Arg Glu Gln
1               5

<210> SEQ ID NO 7
<211> LENGTH: 10
<212> TYPE: PRT
<213> ORGANISM: Artificial Sequence
<220> FEATURE:
<223> OTHER INFORMATION: A synthetic peptide sequence

<400> SEQUENCE: 7

Gly Cys Asp Pro Gly Tyr Ile Gly Ser Arg
1               5                   10

<210> SEQ ID NO 8
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 8

Gly Arg Gly Asp Ser Pro Cys Gly
1               5

<210> SEQ ID NO 9
<211> LENGTH: 16
<212> TYPE: PRT
<213> ORGANISM: Artificial Sequence
<220> FEATURE:
<223> OTHER INFORMATION: A synthetic peptide sequence

<400> SEQUENCE: 9

Gly Cys Arg Asp Arg Pro Phe Ser Met Ile Met Gly Asp Arg Cys Gly
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: A synthetic peptide sequence

<400> SEQUENCE: 10

Gly Cys Arg Asp Gly Pro Leu Gly Leu Trp Ala Arg Asp Arg Cys Gly
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: A synthetic peptide sequence

<400> SEQUENCE: 11

Gly Cys Arg Asp Val Pro Leu Ser Leu Thr Met Gly Asp Arg Cys Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: A synthetic peptide sequence
```

```
<400> SEQUENCE: 12

Gly Cys Arg Asp Gly Pro Gln Gly Ile Trp Gly Gln Asp Arg Cys Gly
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: A synthetic peptide sequence

<400> SEQUENCE: 13

Cys Gly Gly Ser Val Val Tyr Gly Leu Arg
1               5                   10

<210> SEQ ID NO 14
<211> LENGTH: 17
<212> TYPE: PRT
<213> ORGANISM: Artificial Sequence
<220> FEATURE:
<223> OTHER INFORMATION: A synthetic peptide sequence

<400> SEQUENCE: 14

Cys Gly Pro His Ser Arg Asn Gly Gly Gly Gly Gly Arg Gly Asp
1               5                   10                  15

Ser

<210> SEQ ID NO 15
<211> LENGTH: 38
<212> TYPE: PRT
<213> ORGANISM: Artificial Sequence
<220> FEATURE:
<223> OTHER INFORMATION: A synthetic peptide sequence

<400> SEQUENCE: 15

Cys Gly Pro Gly Pro Pro Gly Pro Gly Pro Pro Gly Pro Pro Gly
1               5                   10                  15

Pro Pro Gly Phe Gly Glu Arg Gly Pro Pro Gly Pro Pro Gly Pro Pro
            20                  25                  30

Gly Pro Pro Gly Pro Pro
        35

<210> SEQ ID NO 16
<211> LENGTH: 11
<212> TYPE: PRT
<213> ORGANISM: Artificial Sequence
<220> FEATURE:
<223> OTHER INFORMATION: A synthetic peptide sequence

<400> SEQUENCE: 16

Cys Gly Gly Ala Glu Ile Asp Gly Ile Glu Leu
1               5                   10

<210> SEQ ID NO 17
<211> LENGTH: 16
<212> TYPE: PRT
<213> ORGANISM: Artificial Sequence
<220> FEATURE:
<223> OTHER INFORMATION: A synthetic peptide sequence

<400> SEQUENCE: 17

Gly Cys Arg Asp Ile Pro Glu Ser Leu Arg Ala Gly Asp Arg Cys Gly
1               5                   10                  15
```

```
<210> SEQ ID NO 18
<211> LENGTH: 29
<212> TYPE: PRT
<213> ORGANISM: Artificial Sequence
<220> FEATURE:
<223> OTHER INFORMATION: A synthetic peptide sequence

<400> SEQUENCE: 18

Gly Cys Gly Gly Gln Trp Arg Asp Thr Trp Ala Arg Arg Leu Arg Lys
1               5                   10                  15

Phe Gln Gln Arg Glu Lys Lys Gly Lys Cys Arg Lys Ala
            20                  25

<210> SEQ ID NO 19
<211> LENGTH: 16
<212> TYPE: PRT
<213> ORGANISM: Artificial Sequence
<220> FEATURE:
<223> OTHER INFORMATION: A synthetic peptide sequence

<400> SEQUENCE: 19

Gly Cys Arg Asp Val Pro Leu Ser Leu Tyr Ser Gly Asp Arg Cys Gly
1               5                   10                  15

<210> SEQ ID NO 20
<211> LENGTH: 18
<212> TYPE: PRT
<213> ORGANISM: Artificial Sequence
<220> FEATURE:
<223> OTHER INFORMATION: A synthetic peptide sequence

<400> SEQUENCE: 20

Gly Cys Arg Asp Ser Gly Glu Ser Pro Ala Tyr Tyr Thr Ala Asp Arg
1               5                   10                  15

Cys Gly

<210> SEQ ID NO 21
<211> LENGTH: 16
<212> TYPE: PRT
<213> ORGANISM: Artificial Sequence
<220> FEATURE:
<223> OTHER INFORMATION: A synthetic peptide sequence

<400> SEQUENCE: 21

Gly Cys Arg Asp Val Pro Met Ser Met Arg Gly Gly Asp Arg Cys Gly
1               5                   10                  15

<210> SEQ ID NO 22
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 22

Tyr Ile Gly Ser Arg
1               5

<210> SEQ ID NO 23
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 23
```

```
Ile Lys Val Ala Val
1               5

<210> SEQ ID NO 24
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 24

Ala Glu Ile Asp Gly Ile Glu Leu
1               5

<210> SEQ ID NO 25
<211> LENGTH: 4
<212> TYPE: PRT
<213> ORGANISM: Artificial Sequence
<220> FEATURE:
<223> OTHER INFORMATION: A synthetic peptide sequence

<400> SEQUENCE: 25

Asp Gly Glu Ala
1

<210> SEQ ID NO 26
<211> LENGTH: 4
<212> TYPE: PRT
<213> ORGANISM: Artificial Sequence
<220> FEATURE:
<223> OTHER INFORMATION: A synthetic peptide sequence

<400> SEQUENCE: 26

Val Thr Cys Gly
1

<210> SEQ ID NO 27
<211> LENGTH: 19
<212> TYPE: PRT
<213> ORGANISM: Artificial Sequence
<220> FEATURE:
<223> OTHER INFORMATION: A synthetic peptide sequence

<400> SEQUENCE: 27

Tyr Ser Met Lys Lys Thr Thr Met Lys Ile Ile Pro Phe Asn Arg Leu
1               5                   10                  15

Thr Ile Gly

<210> SEQ ID NO 28
<211> LENGTH: 6
<212> TYPE: PRT
<213> ORGANISM: Artificial Sequence
<220> FEATURE:
<223> OTHER INFORMATION: A synthetic peptide sequence

<400> SEQUENCE: 28

Ser Val Val Tyr Leu Arg
1               5

<210> SEQ ID NO 29
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 29
```

Gly Phe Gly Glu Arg
1               5

<210> SEQ ID NO 30
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 30

Pro His Ser Arg Asn Arg Gly Asp
1               5

<210> SEQ ID NO 31
<211> LENGTH: 26
<212> TYPE: PRT
<213> ORGANISM: Artificial Sequence
<220> FEATURE:
<223> OTHER INFORMATION: A synthetic peptide sequence

<400> SEQUENCE: 31

Gln Trp Arg Asp Thr Trp Ala Arg Arg Leu Arg Ile Cys Phe Gln Gln
1               5                   10                  15

Arg Glu Lys Lys Gly Lys Cys Arg Lys Ala
            20                  25

<210> SEQ ID NO 32
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 32

Val Pro Met Ser Met Arg Gly Gly
1               5

<210> SEQ ID NO 33
<211> LENGTH: 10
<212> TYPE: PRT
<213> ORGANISM: Artificial Sequence
<220> FEATURE:
<223> OTHER INFORMATION: A synthetic peptide sequence

<400> SEQUENCE: 33

Ser Gly Glu Ser Pro Ala Tyr Tyr Thr Ala
1               5                   10

<210> SEQ ID NO 34
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 34

Arg Pro Phe Ser Met Ile Met Gly
1               5

<210> SEQ ID NO 35
<211> LENGTH: 8
<212> TYPE: PRT
<213> ORGANISM: Artificial Sequence
<220> FEATURE:
<223> OTHER INFORMATION: A synthetic peptide sequence

```
<400> SEQUENCE: 35

Val Pro Leu Ser Leu Thr Met Gly
1               5

<210> SEQ ID NO 36
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 36

Val Pro Leu Ser Leu Tyr Ser Gly
1               5

<210> SEQ ID NO 37
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 37

Gly Pro Leu Gly Leu Trp Ala Arg
1               5

<210> SEQ ID NO 38
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 38

Ile Pro Glu Ser Leu Arg Ala Gly
1               5

<210> SEQ ID NO 39
<211> LENGTH: 6
<212> TYPE: PRT
<213> ORGANISM: Artificial Sequence
<220> FEATURE:
<223> OTHER INFORMATION: A synthetic peptide sequence

<400> SEQUENCE: 39

Phe Tyr Phe Asp Leu Arg
1               5

<210> SEQ ID NO 40
<211> LENGTH: 6
<212> TYPE: PRT
<213> ORGANISM: Artificial Sequence
<220> FEATURE:
<223> OTHER INFORMATION: A synthetic peptide sequence

<400> SEQUENCE: 40

Lys Arg Leu Asp Gly Ser
1               5

<210> SEQ ID NO 41
<211> LENGTH: 12
<212> TYPE: PRT
<213> ORGANISM: Artificial Sequence
<220> FEATURE:
<223> OTHER INFORMATION: A synthetic peptide sequence
```

```
<400> SEQUENCE: 41

Gly Trp Thr Val Phe Gln Lys Arg Leu Asp Gly Ser
1               5                   10

<210> SEQ ID NO 42
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 42

Pro His Ser Arg Asn Arg Gly Asp
1               5

<210> SEQ ID NO 43
<211> LENGTH: 4
<212> TYPE: PRT
<213> ORGANISM: Artificial Sequence
<220> FEATURE:
<223> OTHER INFORMATION: A synthetic peptide sequence

<400> SEQUENCE: 43

Arg Glu Asp Val
1

<210> SEQ ID NO 44
<211> LENGTH: 9
<212> TYPE: PRT
<213> ORGANISM: Artificial Sequence
<220> FEATURE:
<223> OTHER INFORMATION: A synthetic peptide sequence

<400> SEQUENCE: 44

Tyr Gly Tyr Tyr Gly Asp Ala Leu Arg
1               5

<210> SEQ ID NO 45
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 45

Pro Asp Ser Gly Arg
1               5

<210> SEQ ID NO 46
<211> LENGTH: 7
<212> TYPE: PRT
<213> ORGANISM: Artificial Sequence
<220> FEATURE:
<223> OTHER INFORMATION: A synthetic peptide sequence

<400> SEQUENCE: 46

Arg Tyr Val Val Leu Pro Arg
1               5

<210> SEQ ID NO 47
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 47
```

```
Gly Arg Lys Arg Lys
1               5

<210> SEQ ID NO 48
<211> LENGTH: 6
<212> TYPE: PRT
<213> ORGANISM: Artificial Sequence
<220> FEATURE:
<223> OTHER INFORMATION: A synthetic peptide sequence

<400> SEQUENCE: 48

Val Gly Val Ala Pro Gly
1               5

<210> SEQ ID NO 49
<211> LENGTH: 4
<212> TYPE: PRT
<213> ORGANISM: Artificial Sequence
<220> FEATURE:
<223> OTHER INFORMATION: A synthetic peptide sequence
<221> NAME/KEY: VARIANT
<222> LOCATION: (1)...(4)
<223> OTHER INFORMATION: Xaa = Any Amino Acid

<400> SEQUENCE: 49

Val Thr Xaa Gly
1

<210> SEQ ID NO 50
<211> LENGTH: 5
<212> TYPE: PRT
<213> ORGANISM: Artificial Sequence
<220> FEATURE:
<223> OTHER INFORMATION: A synthetic peptide sequence
<221> NAME/KEY: VARIANT
<222> LOCATION: (1)...(5)
<223> OTHER INFORMATION: Xaa = Any Amino Acid

<400> SEQUENCE: 50

Asp Leu Xaa Xaa Leu
1               5

<210> SEQ ID NO 51

<400> SEQUENCE: 51

000

<210> SEQ ID NO 52
<211> LENGTH: 8
<212> TYPE: PRT
<213> ORGANISM: Artificial Sequence
<220> FEATURE:
<223> OTHER INFORMATION: A synthetic peptide sequence

<400> SEQUENCE: 52

Ile Pro Val Ser Leu Arg Ser Gly
1               5

<210> SEQ ID NO 53
<211> LENGTH: 10
<212> TYPE: PRT
<213> ORGANISM: Artificial Sequence
<220> FEATURE:
<223> OTHER INFORMATION: A synthetic peptide sequence

<400> SEQUENCE: 53
```

```
Gly Gly Tyr Ala Glu Leu Arg Met Gly Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: A synthetic peptide sequence

<400> SEQUENCE: 54

Gly Gly Pro Leu Gly Leu Tyr Ala Gly Gly
1               5                   10

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
<211> LENGTH: 14
<212> TYPE: PRT
<213> ORGANISM: Artificial Sequence
<220> FEATURE:
<223> OTHER INFORMATION: A synthetic peptide sequence

<400> SEQUENCE: 60

Ala Leu Met Lys Tyr His Ile Leu Asn Thr Gln Cys Ser Glu
1               5                   10

<210> SEQ ID NO 61
<211> LENGTH: 17
<212> TYPE: PRT
<213> ORGANISM: Artificial Sequence
<220> FEATURE:
<223> OTHER INFORMATION: A synthetic peptide sequence

<400> SEQUENCE: 61

Thr Trp Ser Lys Val Gly Gly His Leu Arg Pro Gly Ile Val Gln Ser
1               5                   10                  15

Gly
```

```
<210> SEQ ID NO 62
<211> LENGTH: 11
<212> TYPE: PRT
<213> ORGANISM: Artificial Sequence
<220> FEATURE:
<223> OTHER INFORMATION: A synthetic peptide sequence

<400> SEQUENCE: 62

Ile Val Arg Arg Ala Asp Arg Ala Ala Val Pro
1               5                   10

<210> SEQ ID NO 63
<211> LENGTH: 9
<212> TYPE: PRT
<213> ORGANISM: Artificial Sequence
<220> FEATURE:
<223> OTHER INFORMATION: A synthetic peptide sequence

<400> SEQUENCE: 63

Ser Ile Gly Phe Arg Gly Asp Thr Cys
1               5

<210> SEQ ID NO 64
<211> LENGTH: 12
<212> TYPE: PRT
<213> ORGANISM: Artificial Sequence
<220> FEATURE:
<223> OTHER INFORMATION: A synthetic peptide sequence

<400> SEQUENCE: 64

Phe Gln Gly Val Leu Gln Asn Val Arg Phe Val Phe
1               5                   10

<210> SEQ ID NO 65
<211> LENGTH: 12
<212> TYPE: PRT
<213> ORGANISM: Artificial Sequence
<220> FEATURE:
<223> OTHER INFORMATION: A synthetic peptide sequence

<400> SEQUENCE: 65

Gly Trp Thr Val Phe Gln Lys Arg Leu Asp Gly Ser
1               5                   10

<210> SEQ ID NO 66
<211> LENGTH: 7
<212> TYPE: PRT
<213> ORGANISM: Artificial Sequence
<220> FEATURE:
<223> OTHER INFORMATION: A synthetic peptide sequence

<400> SEQUENCE: 66

Ser Val Val Tyr Gly Leu Arg
1               5

<210> SEQ ID NO 67
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 67

Ile Pro Val Ser Leu
1               5
```

<210> SEQ ID NO 68
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 68

Ser Gly Glu Ser Phe
1               5

<210> SEQ ID NO 69
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 69

Ala Tyr Tyr Thr Ala
1               5

<210> SEQ ID NO 70
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 70

Phe Tyr Asp Leu Arg
1               5

<210> SEQ ID NO 71
<211> LENGTH: 5
<212> TYPE: PRT
<213> ORGANISM: Artificial Sequence
<220> FEATURE:
<223> OTHER INFORMATION: A synthetic peptide sequence

<400> SEQUENCE: 71

Pro His Ser Arg Asn
1               5

<210> SEQ ID NO 72
<211> LENGTH: 6
<212> TYPE: PRT
<213> ORGANISM: Artificial Sequence
<220> FEATURE:
<223> OTHER INFORMATION: A synthetic peptide sequence

<400> SEQUENCE: 72

Arg Gly Asp Phe Glu Ile
1               5

<210> SEQ ID NO 73
<211> LENGTH: 14
<212> TYPE: PRT
<213> ORGANISM: Artificial Sequence
<220> FEATURE:
<223> OTHER INFORMATION: A synthetic peptide sequence

<400> SEQUENCE: 73

Pro His Ser Arg Asn Gly Gly Gly Gly Gly Arg Gly Asp
1               5                   10

<210> SEQ ID NO 74

```
<211> LENGTH: 6
<212> TYPE: PRT
<213> ORGANISM: Artificial Sequence
<220> FEATURE:
<223> OTHER INFORMATION: A synthetic peptide sequence
<221> NAME/KEY: VARIANT
<222> LOCATION: 3
<223> OTHER INFORMATION: Xaa = O (hydroxyproline)

<400> SEQUENCE: 74

Gly Phe Xaa Gly Glu Arg
1               5
```

3D SYNTHETIC TISSUE HYDROGELS

CROSS-REFERENCE TO RELATED APPLICATIONS

This application claims the benefit of the filing date of U.S. application Ser. No. 62/459,815, filed on Feb. 16, 2017, the disclosure of which is incorporated by reference herein.

STATEMENT OF GOVERNMENT RIGHTS

The invention was made with government support under grant DP2 CA186573-01 from the National Institutes of Health. The Government has certain rights in the invention.

BACKGROUND

The vast majority of systems available to study cells in response to their microenvironment have been in 2D, ranging from protein coated surfaces to hydrogels (Barney et al., 2015; Herrick et al., 2015; Nguyen et al., 2014). These platforms restrict cell adhesions to an x-y plane and forces an apical-basal polarity, which directly contrasts to in vivo cell adhesion (Baker and Chen, 2012; Zaman et al., 2006). Many engineers have worked to design microenvironments that recapitulate 3D geometry (Baker et al., 2015; Kloxin et al., 2010; Peyton et al., 2011). These 3D biocompatible hydrogels mimic the high water content and elasticity of native tissues and can be synthesized from an array of natural, synthetic, or a blend of these polymer materials (Van Vlierberge et al., 2011). Natural materials are inherently biocompatible, but often lack physiological relevancy with respect to protein makeup and tissue modulus. In contrast, synthetic materials can be independently tuned to display desired mechanical properties and ligand densities, but do need to be modified to have bio-functionality (Tibbitt et al., 2009). This ability to independently tune material properties makes synthetic hydrogels ideal for designing tissue specific materials. However, most synthetic platforms are either over simplified, containing 1-2 bio-functional peptides, and fail to capture unique properties of individual tissue sites. In contrast, platforms that aim to recapitulate tissue properties can be labor intensive and lab specific (Torisawa et al., 2014; Lee et al., 2012).

SUMMARY

The present disclosure provides for synthetic hydrogels that have increased biocompatability as a result of incorporation of tissue specific peptides and tuning of polymer crosslinking into a polymeric hydrogel to match the chemical and mechanical properties of a particular tissue, e.g., bone marrow tissue. For example, bone marrow is the soft interior tissue between hard compact bone where many immune and stromal stem cells reside, and like every tissue, bone marrow has a unique protein and sugar composition paired with a distinct range of stiffness (Jansen et al., 2015; Uhlén et al., 2015). It is well established that these chemical and physical cues provided by the hematopoietic microenvironment are key to the function of this organ system (Choi and Harley, 2017 and 2016). Both the protein(s) and stiffness of this tissue regulate important cellular processes like migration, proliferation, and/or differentiation. Thus, it is not surprising that disease progression correlates with deregulation of protein remodeling and stiffening of the surrounding stroma.

As described below, a 3D synthetic, e.g., polyethylene glycol (PEG), hydrogel was modified using bioinformatics to identify proteins in a specific tissue and bulk mechanical tissue testing methods on tissues, to adapt the hydrogel to recapitulate the integrin binding, matrix degradability, and/or bulk stiffness of a tissue. In one embodiment, a bone marrow tissue mimic was prepared, which is useful to study some of the extracellular matrix (ECM) features that drive cell phenotypes that play a role in disease progression and/or homeostasis or development. A synthetic hydrogel was functionalized with di-functional peptide sequences that can degrade in the presence of cell-secreted enzymes and/or mono-or di-functional peptides that bind to cell surface integrins, e.g., using Michael-type addition chemistry. In one embodiment, twenty different biochemical features in human bone marrow were identified and quantified using an algorithm developed with data from the Protein Atlas. To validate that this algorithm identified unique protein signature of tissues, ECM proteins were filtered from human bone marrow, lung, and brain tissues and analyzed via mass spectrometry (MS). For each tissue, the proteins identified through MS were most similar to the protein signatures identified for bone marrow, brain, or lung tissue using the algorithm. Using native tissue as a guide, the effective Young's modulus of hydrogel may be altered to match the average stiffness of tissue, e.g., marrow tissue (4.4±1.0 kPa). As described below both marrow and the PEG hydrogel have similar compressive properties, validating the use of this platform for modeling the bulk mechanics of marrow tissue.

In one embodiment, a method to prepare synthetic hydrogels having tissue-specific properties is provided. The method includes selecting one or more integrin binding proteins and combining those with one or more matrix metalloproteinase (MMP) substrate peptides, found in the selected mammalian tissue, and selecting one or more monomers for a polymer matrix with a selected polymer density. The monomer(s) for the polymer matrix and the selected integrin binding and MMP substrate proteins or peptides are combined under conditions that form a tissue-specific hydrogel having the selected polymer density. In one embodiment, the polymer comprises PEG, agarose, collagen, fibrin, silk, matrigel, alginate, polyacrylamide, poly-lactic acid, hydrogels with zwitterions coupled to decrease protein adsorption, like HEMA and/or phosphorycholine, or methylcellulose. In one embodiment, the polymer is formed of 2K, 10K, 20K or 40K star PEG polymer with either 4, 6 or 8 arms. In one embodiment, the proteins or peptides comprise a plurality of integrin binding proteins and proteins substrates of MMP degradable enzymes, or peptides thereof. In one embodiment, the tissue is bone marrow, heart, brain or lung tissue. In one embodiment, the integrin heterodimers bind to peptides that represent binding motifs in two or more of the following full-length proteins: entactin/nidogen; vitronectin; vWF; netrin 1; fibronectin; collagen 1; fibrinogen alpha; osteopontin; fibrinogen gamma; thrombospondin; collagen IX; tenascin C; laminin-alpha; laminin-beta; or laminin gamma. In one embodiment, the integrin binding peptides are present at about 1 molar % to about 30 molar %, or any range in between, e.g., about 1 molar % to 15 molar %, 5 molar % to 15 molar %, or 5 molar % to 30 molar %. In one embodiment, peptides that are selectively degraded are in response to one or more of cell secreted MMPs MMP-1, MMP-14, MMP-1, MMP-2, MMP-3, MMP-7, MMP-9, or MMP-13 present at about 10 molar % to 25 molar %, e.g., 10 molar % to 20 molar %.

Further provided is a hydrogel comprising a plurality of peptides, wherein the peptides include peptides of two or more of entactin/nidogen; vitronectin; vWF; netrin 1; fibronectin; collagen 1; fibrinogen alpha; osteopontin; fibrinogen gamma; thrombospondin; collagen IX; tenascin C; laminin-alpha; laminin-beta; laminin gama; MMP-1, MMP-14, MMP-1, MMP-2, MMP-3, MMP-7, MMP-9, or MMP-13. In one embodiment, the peptides include one or more of RGD, LRE, YIGSR (SEQ ID NO:22), IKVAV (SEQ ID NO:23), AEIDGIEL (SEQ ID NO:24), DGEA (SEQ ID NO:25), VTCG (SEQ ID NO:26), YSMKKTTM-KIIPFNRLTIG (SEQ ID NO:27), SVVYLR (SEQ ID NO:28), GPR, GFOGER (SEQ ID NO:29), PHSRN-RGB (SEQ ID NO:30), or QWRDTWARRL-RICFQQREKKGKCRKA (SEQ ID NO:31). In one embodiment, the peptides include one or more VPMS/MRGG (SEQ ID NO:32), SGESPAY/YTA (SEQ ID NO:33), RPFS/MIMG (SEQ ID NO:34), VPLS/LTMG (SEQ ID NO:35), VPLS/LYSG (SEQ ID NO:36), GPLG/LWAR (SEQ ID NO:37), or IPES/LRAG (SEQ ID NO:38). In one embodiment, the hydrogel comprises PEG, e.g., cross-linked PEG. In one embodiment, the hydrogel has peptides from the following full-length proteins: laminin A/C, laminin β1, laminin γ, fibrinogen α, fibrinogen β, fibrinogen γ, thrombospondin-1, vitronectin, fibronectin, collagen α1, collagen 1, collagen α1, collagen II, collagen III, collagen IV, collagen α21, collagen I, collagen V, collagen IV, vWf, fibrinogen α, fibrinogen β, fibrinogen γ, vitronectin, fibronectin, tenascin R, or Galectin 1, or any combination thereof. In one embodiment, the hydrogel has peptides of collagen αI, collagen II, collagen III, collagen IV, collagen α21, collagen I, collagen V, collagen IV, vWf, fibrinogen α, fibrinogen β, fibrinogen γ, vitronectin, fibronectin, tenascin R, and/or Galectin 1.

In one embodiment, the hydrogel comprises cells from the tissue of origin, or cells including but not limited to pluripotent cells, embryonic stem cells or a subset thereof, umbilical cord cells or a subset thereof, bone marrow cells or a subset thereof, peripheral blood cells or a subset thereof, adult-derived stem or progenitor cells or a subset thereof, tissue-derived stem or progenitor cells or a subset thereof, mesenchymal stem cells (MSC) or a subset thereof, skeletal muscle-derived stem or progenitor cells or a subset thereof, multipotent adult progenitor cells (MAPC) or a subset thereof, cardiac stem cells (CSC) or a subset thereof, multipotent adult cardiac-derived stem cells or a subset thereof, or hematopoietic stem cells or a subset thereof.

BRIEF DESCRIPTION OF THE FIGURES

FIGS. 4A-4G. The PEG hydrogel accurately models the bulk compressive properties of bone marrow tissue. 4A) Rheology data from Jansen et al. (2014) for the effective Young's modulus ($E^{Eff}$) of porcine bone marrow at 35° C. 4B) The $E^{Eff}$ for 20 wt % 8-arm 20K PEG hydrogels crosslinked at a 1:1 thiol to maleimide molar ratio with purely 1.5K PEG dithiol (PDT, black) or with the bone marrow cocktail of PDT and MMP crosslinkers (MMP, blue). 4C) The $E^{Eff}$ for 20 wt % 8-arm 20K PEG hydrogels crosslinked at a 1:1 thiol to maleimide molar ratio with PDT and coupled with different concentrations of the bone marrow peptide cocktail for 10 minutes before gelation. 4D) Encapsulated MSC circularity with respect to peptide concentration (left) and 4E) representative cell traces (right). Significance is determined using a two-tailed t-test where p=0.05, and error bars represent the SEM. (N≥2, n≥3 for mechanical testing; N≥2, n≥5 for cell circularity). 4F) Representative compressive loading data from porcine bone marrow (purple, Jansen et al., 2015) and 4G) the PEG bone marrow hydrogel (red) matched to a Hertzian model for the calculated modulus (black line).

FIGS. 7A-7D. Adhesion of breast cancer cells and PCR on plastic. 7A) Average cell area for hMSCs (black) and breast cancer cells (red) 2 hours after seeding onto coverslips. 7B) Heat map depicting the log 2 fold change in breast cancer cell area at 2 hr from no treatment (NT) for parental MDA-MB-231 (P) and MDA-MB-231 BOM 1833 (BOM) cells (BM=bone marrow peptide cocktail). 7C) hMSC cell area over 2 hours for cells seeded unto a surface coupled with the bone marrow peptide cocktail or PEG. 7D) Relative intensity of fluorescently tagged fibronectin seeded onto these coverslips for 2 hours before imaging Significance is determined using a two-tailed t-test where p=0.05 (N≥2, n≥40).

FIGS. 8A-8B. MDA-MB-231 cells can degrade MMP-sensitive crosslinkers. 8A) Box and whisker plot for the ratio of MDA-MB-231 spheroid size from 8B) day 6 (d6) to day 1 (d1) into a hydrogel with one MMP degradable crosslinker (N=1, n=2). B) Representative image of a spheroid encapsulated in a hydrogel at day 1 (top) and 6 (bottom), scale 100 μm.

FIGS. 9A-9B. Integrin binding proteins, tissues have increased RNA levels of those proteins, and binding motifs (FIG. 9A—SEQ ID NOs: 25, 29, 39 and 40; FIG. 9B—SEQ ID NOs: 22, 23, 24, 27, 30, 31, 43, 44, 45, 46, 47, 48, 49, 50, 65, and 66).

FIGS. 10A-10F, MMP degradable enzymes and substrates, tissues have increase RNA levels of those proteins and peptide degrading sequences (FIG. 10A—SEQ ID NOs: 32 and 67-69; FIG. 10B—SEQ ID NO: 34; FIG. 10C—SEQ ID NOs: 35 and 36; FIG. 10D—SEQ ID NO: 53; FIG. 10E—SEQ ID NOs: 38 and 54).

FIGS. 11A-11F. IHC, RNA expression and tissues have increased RNA levels of those proteins of all quantified proteins.

FIG. 12. Integrin binding proteins and peptides and proportion in one exemplary hydrogel (SEQ ID NOs: 1, 2, 3, 4, 5, 6, 7, 8, 13, 14, 15, 16, 18, 22, 23, 24, 25, 27, 29, 30, 31, 49 and 66).

FIGS. 13A-13C. Degradable proteins and peptides and proportion in one exemplary hydrogel (FIG. 13A—SEQ ID NOs: 20, 21, 32 and 33; FIG. 13B—SEQ ID NOs: 9, 11, 19, 34, 35, and 36; FIG. 13C—SEQ ID NOs: 10, 17, 37 and 38).

FIGS. 14A-1-14C-2. Proteins in bone marrow (14A1-14A4), lung (14B1-14B-10), and brain (14C-1-14-C2).

FIGS. 19A-19B. Proteins found in and peptides useful in hydrogels specific for brain (FIG. 19A—SEQ ID NOs: 22, 23, 25, 26, 30, 41, 47, 60, 61, 62 and 70 (ALMKYHILNTQCSE (SEQ ID NO: 60)), (TWSKVGGHLRPGIVQSG (SEQ ID NO: 61)), and (IVR-RADRAAVP (SEQ ID NO: 62)) or lung (FIG. 19B—SEQ ID NOs: 22, 23, 24, 25, 29, 39, 45, 46, 47, 48, 49, 50, 63, 64, 71 and 72 (SIGFRGDTC (SEQ ID NO: 63)) and (FQGVLQNVRFVF (SEQ ID NO: 64))).

DETAILED DESCRIPTION

Figure 1A:
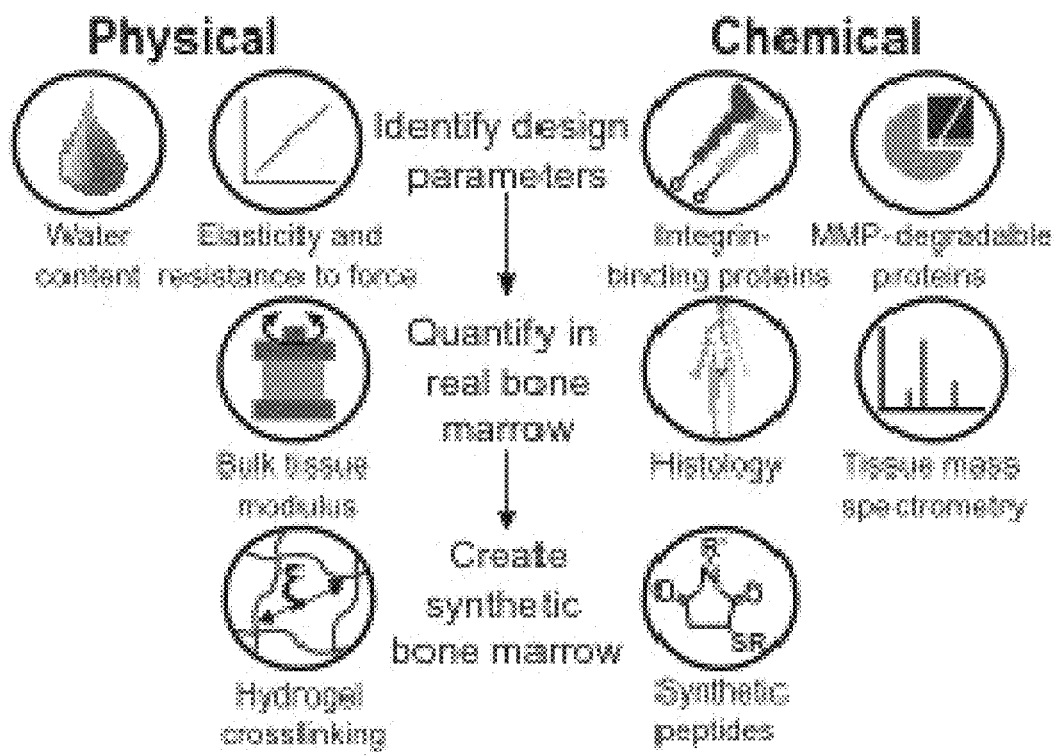
FIGS. 1A-1D. Adapting a PEG hydrogel to mimic the physical and chemical properties of bone marrow tissue. 1A) Tissue has physical and chemical properties like water content, elasticity, integrin-binding, and MMP-degradable proteins. These properties can be quantified in real bone marrow tissue using rheology, mass spectrometry, and tissue histology (image from Protein atlas). These features are represented synthetically by tuning hydrogel crosslinking and incorporating bio-functional peptides. 1B) The hydrogel (bottom left) to mimic bone marrow tissue (top left, image from Jansen et al. 2014) is composed of an 8-arm PEG macromer functionalized with 1C) 13 mono-functional integrin-binding peptides (SEQ ID NOs: 22-31) and crosslinked with 7 di-functional MMP degradable peptides and a linear PEG dithiol. The known functional sequence for each peptide is depicted in bold, with the percentage it is present in the hydrogel (% relative to other peptides). All histology images are representative of each protein in human bone marrow tissue (images from the Protein Atlas). The lines in 1D) connect each MMP to their known protein substrates and the slash (/) indicates the cleavage location for each enzyme on their matched peptide (SEQ ID NOs: 32-38).

The present disclosure provides methods for making hydrogels tissue-specific, allowing for substrates with improved drug screening for diseases that exhibit phenotypic changes because of tissue-specific microenvironment cues, improved ability to study cell signal transduction from tissue microenvironments, and/or the ability to better study how the tissue plays a role in both disease and drug response to small molecule inhibitors.

As described herein a 3D synthetic hydrogel, e.g., comprising polyethylene glycol (PEG), having a plurality of peptides, from proteins present in a specific tissues was prepared. Three-dimensional polyethylene glycol (PEG) hydrogels have been widely used as highly tunable and reproducible cell culturing platforms that recapitulate in vivo tissue structure, water content, and bulk elasticity over two-dimensional gels and/or plastic. Most PEG gels are functionalized with 1-2 bio-functional peptide moieties, like RGD, which greatly underrepresents the chemical diversity of proteins found in natural tissue.

As described herein, a bioinformatics approach was used by taking tissue characterization data, like histology and mass spectrometry, and combining it with known tissue mechanics to create a synthetic tissue-specific material. This method was applied to bone marrow tissue and the resulting material represents the MMP-degradability, integrin-binding, and mechanics of real marrow tissue. By combining these tissue features, the bone marrow tissue model is better able to recapitulate the differentiation capacity of human mesenchymal stem cells over RGD-gels, highlighting a need for tissue-specific synthetic materials to understand how native tissues direct cell function. In one embodiment, a 3D polyethylene glycol hydrogel (PEG) was prepared having peptides based on a combination of bioinformatics and mechanical tissue properties, thereby adapting the hydrogel to recapitulate the integrin binding, matrix degradability, and bulk stiffness of tissue, e.g., bone marrow tissue. In one embodiment, the hydrogel is functionalized with 7 peptide sequences that can degrade in the presence of cell-secreted enzymes and 13 peptides that bind to cell surface integrins. These were identified and quantified using an algorithm developed with data from the ProteinAtlas, and validated using secondary protein identification methods, such as mass spectrometry, on tissue from healthy donors (Uhlén et al., 2015). The incorporation of these ligands, while maintaining physiological tissue stiffness, allows for bioactivity for each individual peptide. MSCs in these materials remain stem-like and have the highest capacity to differentiation into both bone and fat when provided the appropriate cues. Overall, a method is described that uses a top-down approach to filtering tissue characterization data to determine optimal design parameters for tissue-specific materials. This technique is applied to the design of a novel in vitro tissue throughout the body that could greatly improve high-throughput screening or in vitro studies for signal transduction in tissue specific environments.

Proteins and Peptides for Use in the Hydrogel and Methods

Exemplary integrin binding proteins to which the proteins or peptides useful in the hydrogels bind, include but are not limited to one or more of Collagen 1, Collagen II, Collagen III, Collagen IV, Collagen V, Collagen VI, Collagen VII, Collagen VIII, Collagen IX, Collagen X, Collagen XI, Collagen XIV, COMP, Factor XII, Factor X, Fibulin, Fibrillin, Fibrinogen, Fibronectin, Laminin α, Laminin β, Laminin γ, Elastin, Entactin/Nidogen, Netrin-1, Reelin, Osteopontin, Thrombospondin, Tenascin C, Vitronectin, or von Willebrand factor. For example, peptides useful in the hydrogel and methods include but are not limited to one or more of GFOGER (SEQ ID NO:29), DGEA (SEQ ID NO:25), GFOGER (SEQ ID NO:29), FYFDLR (SEQ ID NO:39), RGD, GPR, KRLDGS (SEQ ID NO:40), RGD, YSMKKTTMKIIPFNRLTIG (SEQ ID NO:27), GWTVFQKRLDGS (SEQ ID NO:41), RGD, PHSRN-RGD (SEQ ID NO:42), LDV, IDA, REDV (SEQ ID NO:43), IKVAV (SEQ ID NO:23), YGYYGDALR (SEQ ID NO:44), RGD, YIGSR (SEQ ID NO:2), PDSGR (SEQ ID NO:45), RYVVLPR (SEQ ID NO:46), LRE, GRKRK (SEQ ID NO:47), VGVAPG (SEQ ID NO:48), RGD, QWRDT-WARRLRKFQQREKKGKCRKA (SEQ ID NO:31), SVVYGLR (SEQ ID NO:28), LDV, RGD, RGD, VTXG (SEQ ID NO:49), AEIDGIEL (SEQ ID NO:24), DLXXL (SEQ ID NO:50), RGD, or RGD. In one embodiment, peptides useful in the hydrogel and methods include but are not limited to one or more of GFOGER (SEQ ID NO:29), DGEA (SEQ ID NO:25), FYFDLR (SEQ ID NO:39), RGD, GPR, KRLDGS (SEQ ID NO:40), YSMKKTTM-KIIPFNRLTIG (SEQ ID NO:27), GWTVFQKRLDGS (SEQ ID NO:41), PHSRN-RGD (SEQ ID NO:42), LDV, IDA, REDV (SEQ ID NO:43), IKVAV (SEQ ID NO:23), YGYYGDALR (SEQ ID NO:44), YIGSR (SEQ ID NO:2), PDSGR (SEQ ID NO:45), RYVVLPR (SEQ ID NO:46), LRE, GRKRK (SEQ ID NO:47), VGVAPG (SEQ ID NO:48), QWRDTWARRLRKFQQREKKGKCRKA (SEQ ID NO:31), SVVYGLR (SEQ ID NO:28), VTXG (SEQ ID NO:49), AEIDGIEL (SEQ ID NO:24), or DLXXL (SEQ ID NO:50).

Exemplary integrin binding proteins include but are not limited to one or more of Entactin/Nidogen, Vitronectin, von Willebrand Factor, Netrin-1, Fibronectin, Osteopontin, Collagen I, Fibrinogen, Thrombospondin, Fibrinogen, Tenascin C, Collagen IX, Laminin Alpha, Laminin Beta, or Laminin gamma, Exemplary synthetic peptides useful in the hydrogel and methods include but are not limited to one or more of GRGDSPCG (SEQ ID NO:8), GCGGQWRDT-WARRLRKFQQREKKGKCRKA (SEQ ID NO:18), CGPHSRNGGGGGGRGDS (SEQ ID NO:14), CGGSV-VYGLR (SEQ ID NO:13), CGP(GPP)5GFOGER(GPP)5 (SEQ ID NO:15), GPRGGC (SEQ ID NO:2), CSVTCG (SEQ ID NO:4), CGGYSMKKTTMKIIPFNRLTIG (SEQ ID NO:5), CGGAEIDGIEL (SEQ ID NO:16), GCGDGEA (SEQ ID NO:1), CSRARKQAASIKVAVADR (SEQ ID NO:3), GCDPGYIGSR (SEQ ID NO:7), or GCKQLREQ (SEQ ID NO:6), peptides which include RGD, QWRDT-WARRLRKFQQREKKGKCRKA (SEQ ID NO:31), PHSRN-RGD (SEQ ID NO:42), SVVYGLR (SEQ ID NO:28), GFOGER (SEQ ID NO:29), GPR, VTXG (SEQ ID NO:49), YSMKKTTMKIIPFNRLTIG (SEQ ID NO:27), AEIDGIEL (SEQ ID NO:24), DGEA (SEQ ID NO:25), IKVAV (SEQ ID NO:23), YIGSR (SEQ ID NO:22), or LRE.

Exemplary MMPs include but are not limited to one or more of Collagenase-1 (MMP-1), Gelatinase A (MMP-2), Stromelysin-1 (MMP-3), Matrilysin (MMP-7), Collagenase 2 (MMP-8), Gelatinase B (MMP-9), Stromelysin-2 (MMP-10), Stromelysin-3 (MMP-11), Machrophage metalloelastase (MMP-12), Collagenase-3 (MMP-13), MT1-MMP (MMP-14), MT2-MMP (MMP-15), MT3-MMP (MMP-16), MT4-MMP (MMP-17), Collagenase-4 (MMP-18), RASI-1 (MMP-19), Enamelysin (MMP-20), XMMP (MMP-21), MT5-MMP (MMP-24), MT6-MMP (MMP-25), Endometase (MMP-26), Matrilysin-2 (MMP-27), CMMP, or Epilysin (MMP-28), which degrade: for MMP-1 Aggrecan, Collagen I, Collagen II, Collagen III, Collagen VII, Collagen VIII, Collagen X, Collagen XI, Entactin/Nidogen, Fibronectin, Gelatin I, Laminin, Myelin Basic, Link Protein, Tenascin, Vitronectin, Alpha1-PI, Alpha1-AC, Alpha2-M, Casein, C1q, Fibrinogen, and IL-1beta; for MMP-2, Aggrecan, Collagen 1, Collagen III, Collagen IV, Collagen V, Collagen VII, Collagen X, Collagen XI, Decorin, Elastin, Entactin/Nidogen, Fibrillin, Fibronectin, Fibulins, Gelatin I, Laminin, Link Protein, Myelin Basic, Osteonectin, Tenascin, Vitronectin, Alpha1-PI, Alpha1-AC, C1q, Fibrinogen, IL-1beta, Plasminogen, and Substance P; for MMP-3, Aggrecan, Collagen III, Collagen IV, Collagen V, Collagen VII, Collagen IX, Collagen X, Collagen XI, Decorin, Elastin, Entactin/Nidogen, Fibrillin, Fibronectin, Gelatin I, Laminin, Link Protein, Myelin Basic, Osteonectin, Tenascin, Vitronectin, Alpha1-PI, Alpha1-AC, Alpha2-M, Casein, C1q, E-cadherin, Fibrinogen, IL-1beta, Plasminogen, Substance P, T kininogen; for MMP-7, Aggrecan, Collagen I, Collagen IV, Decorin, Elastin, Entactin/Nidogen, Fibronectin, Fibulins, Gelatin I, Laminin, Link Protein, Myelin Basic, Osteonectin, Tenascin, Vitronectin, Alpha1-PI, Casein, E-cadherin, Fibrinogen, and Plasminogen; for MMP-8, Aggrecan, Collagen I, Collagen II, Collagen III, Alpha1-PI, Alpha2-M, C1q, Fibrinogen, and Substance P; for MMP-9, Aggrecan, Collagen IV, Collagen V, Collagen XI, Collagen XIV, Decorin, Elastin, Fibrillin, Fibronectin, Gelatin I, Laminin, Link Protein, Myelin Basic, Osteonectin, Vitronectin, Alpha1-PI, Alpha2-M, Casein, C1q, Fibrinogen, IL-1beta, Plasminogen, or Substance P; for MMP-10, Aggrecan, Collagen III, Collagen IV, Collagen V, Elastin, Fibronectin, Gelatin 1, Link Protein, Casein, or Fibrinogen; for MMP-11, Alpha1-PI, Alpha2-M, Aggrecan, Collagen I, Collagen IV, Elastin, Entactin/Nidogen, Fibrillin, Fibronectin, Gelatin I, Laminin, Myelin Basic, Vitronectin, Alpha2-M, Alpha1-PI, Factor XII, Fibrinogen, Plasminogen, or Substance P; for MMP-12, Aggrecan, Collagen I, Collagen II, Collagen III, Collagen VI, Collagen IX, Collagen X, Collagen XIV, Fibrillin, Fibronectin, Gelatin I, Osteonectin, Alpha2-M, Casein, C1q, Factor XII, or Fibrinogen; for MMP-13, Aggrecan, Collagen I, Collagen II, Collagen III, Entactin/Nidogen, Fibrillin, Fibronectin, Gelatin I, Laminin, Vitronectin, Alpha1-PI, Alpha2-M, Factor XII, Fibrinoge, Collagen III, or Fibronectin; or for MMP-14 Aggrecan, Collagen I, Collagen I, Collagen IV, Fibronectin, Gelatin I, Tenascin, Casein, Collagen IV, Fibronectin, Gelatin I, Alpha1-PI, or Fibrinogen. Exemplary peptide degrading sequences include but are not limited to one or more of VPMS/MRGG (SEQ ID NO:32), IPVS/LRSG (SEQ ID NO:52), SGESPAY/YTA (SEQ ID NO:33), RPFS/MIMG (SEQ ID NO:34), VPLS/LTMG (SEQ ID NO:35), VPLS/LYSG (SEQ ID NO:36), GGYAE/LRMGG (SEQ ID NO:53), GPLG/LWAR (SEQ ID NO:37), IPES/LRAG (SEQ ID NO:38), or GGPLG/LYAGG (SEQ ID NO:54).

Exemplary enzymes such as Collagenase-1, Gelatinase A, Stromelysin-1, Matrilysin, Gelatinase B, Collagenase-3, or MT1-MMP, have as a substrate peptides that degrade in the presence of the cell secreted MMP enzymes including but not limited to one or more of GCRDVPMSMRGGDRCG (SEQ ID NO:21), GCRDSGESPAYYTADRCG (SEQ ID NO:20), GCRDRPFSMIMGDRCG (SEQ ID NO:9), GCRDVPLSLTMGDRCG (SEQ ID NO:11), GCRDVPLSYSGDRCG (SEQ ID NO:19), GCRDGPLGLWARDRCG (SEQ ID NO:10), or GCRDIPESLRAGDRCG (SEQ ID NO:17), which include the following binding/degradable moieties include but are not limited to VPMS/MRGG (SEQ ID NO:32) SGESPAY/YTA (SEQ ID NO:33), RPFS/MIMG (SEQ ID NO:34), VPLS/LTMG (SEQ ID NO:35), VPLS/LYSG (SEQ ID NO:36), GPLG/LWAR (SEQ ID NO:37), or IPES/LRAG (SEQ ID NO:38).

Exemplary other proteins, e.g., having a peptide useful in the hydrogel, include but are not limited to alpha2-M, Aggrecan, Amyloid P Component, C1q, C1q, C1q, E-cadherin, Collagen X, Collagen XI, Collagen XI, Collagen XIV, Collagen 1 A1, Collagen 1 A2, Collagen II, Collagen III, Collagen IV, Collagen IV, Collagen IV, Collagen IV, Collagen IV, Collagen IV, Collagen V, Collagen V, Collagen V, Collagen VI, Collagen VI, Collagen VI, Collagen VI, Collagen VII, Collagen VIII, Collagen VIII, Collagen IX, Collagen IX, Collagen IX, COMP, iC3b, Casein, Casein, Casein, Decorin, Elastin, Elastin microfibril interfacer 1, Factor XII, Factor X, Fibulin, Fibulin, Fibulin, Fibulin, Fibrillin, Fibrillin, Fibrillin, Fibrinogen alpha, Fibrinogen beta, Fibrinogen gamma, VEGF-D, Fibronectin, Link Protein, ICAM, ICAM, ICAM, ICAM, ICAM, IGFBP-1, IL1beta, T kininogen, Laminin Alpha, Laminin Alpha, Laminin Alpha, Laminin Alpha, Laminin Alpha, Laminin Beta, Laminin Beta, Laminin Beta, Laminin Beta, Laminin gamma, Laminin gamma, Laminin gamma, Galectin-8, LAP-TGF-beta, LAP-TGF-beta, LAP-TGF-beta, LAP-TGF-beta, MAdCAM-1, Myelin Basic, MFG-E8, Collagenase-1, Stromelysin-2, Stromelysin-3, Machrophage metalloelastase, Collagenase-3, MT1-MMP, MT2-MMP, MT3-MMP, MT4-MMP, Collagenase-4, RASI-1, Gelatinase A, Enamelysin, XMMP, CMMP, MT5-MMP, MT6-MMP, Endometase, Matrilysin-2, Epilysin, Stromelysin-1, Matrilysin, Collagenase02, Gelatinase B, Entactin/Nidogen, Netrin-1, PECAM-1, uPAR, Plasminogen, Reelin, alpha1-PI, alpha1-AC, Substance P, Osteonectin, Osteopontin, Thrombospondin, Thrombospondin, Thrombospondin, Thrombospondin, Tenascin C, Tenascin N, Tenascin R, Tenascin XB, VCAM-1, VEGFA, VEGFB, VEGF-C, Vitronectin, or vWF.

Hydrogels

Hydrogels are hydrophilic polymeric networks, with chemical or physical crosslinks, that are capable of swelling and can retain a large amount of water. Many hydrogels exhibit biocompatibility, and cause minimal inflammatory responses, thrombosis, and tissue damage. In addition, hydrogels have high permeability for oxygen, nutrients, and other water-soluble metabolites.

The hydrogel material may provide immunoisolation yet allows facile diffusion of oxygen, nutrients, and metabolic products.

Because the mechanical properties of many hydrogels can be tailored to match those of many soft tissues, those polymeric materials alone may be employed in the biological electrodes of the invention.

Suitable biocompatible materials for the polymers include but are not limited to polyacetic or polyglycolic acid and derivatives thereof, polyorthoesters, polyesters, polyurethanes, polyamino acids such as polylysine, lactic/glycolic acid copolymers, polyanhydrides and ion exchange resins such as sulfonated polytetrafluorethylene, polydimethyl siloxanes (silicone rubber) or combinations thereof.

In one embodiment, the scaffold polymer is formed from natural proteins or materials which may be crosslinked using a crosslinking agent such as 1-ethyl-3-(3-dimethylaminopropyl)carbodiimide hydrochloride. Such natural materials include albumin, collagen, fibrin, alginate, extracellular matrix (ECM), e.g., xenogeneic ECM, hyaluronan, chitosan, gelatin, keratin, potato starch hydrolyzed for use in electrophoresis, and agar-agar (agarose), or other "isolated materials". An "isolated" material has been separated from at least one contaminant structure with which it is normally associated in its natural state such as in an organism or in an in vitro cultured cell population.

Other biocompatible materials include synthetic polymers in the form of hydrogels or other porous materials, e.g., permeable configurations or morphologies, such as polyvinyl alcohol, polyvinylpyrrolidone and polyacrylamide, polyethylene oxide, poly(2-hydroxyethyl methacrylate); natural polymers such as gums and starches: synthetic elastomers such as silicone rubber, polyurethane rubber; and natural rubbers, and include poly[α(4-aminobutyl)]-1-glycolic acid, polyethylene oxide, polyorthoesters, silk-elastin-like polymers, alginate, EVAc (poly(ethylene-co-vinyl acetate), microspheres such as poly (D, L-lactide-co-glycolide) copolymer and poly (L-lactide), poly(N-isopropylacrylamide)-b- poly(D,L-lactide), a soy matrix such as one cross-linked with glyoxal and reinforced with a bioactive filler, e.g., hydroxylapatite, poly(epsilon-caprolactone)-poly(ethylene glycol) copolymers, poly(acryloyl hydroxyethyl) starch, polylysine-polyethylene glycol, an agarose hydrogel, or a lipid microtubule-hydrogel.

In one embodiment, complexes are embedded in or applied to a material including but not limited to hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols, or combinations thereof.

In some embodiments, a biocompatible polymeric material is derived from a biodegradable polymeric such as collagen, e.g., hydroxylated collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), or poly(dioxanone) (PPS).

In another embodiment, the biocompatible material includes polyethyleneterephalate, polytetrafluoroethylene, copolymer of polyethylene oxide and polypropylene oxide, a combination of polyglycolic acid and polyhydroxyalkanoate, gelatin, alginate, poly-3-hydroxybutyrate, poly-4-hydroxybutyrate, and polyhydroxyoctanoate, and polyacrylonitrilepolyvinylchlorides.

In one embodiment, the following polymers may be employed, e.g., natural polymers such as starch, chitin, glycosaminoglycans, e.g., hyaluronic acid, dermatan sulfate and chrondrotin sulfate, and microbial polyesters, e.g., hydroxyalkanoates such as hydroxyvalerate and hydroxybutyrate copolymers, and synthetic polymers, e.g., poly (orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), pol(D,L-lactide-coglycolide), poly(lactic acid colysine) and polycaprolactone.

Exemplary functional groups for Micheal-type addition reactions are alkenes include but are not limited to groups such as noroborene, vinyl silane, allyl ether, viny ether, fumarate, propene, maleimide, methacrylate, crotonate, styrene, acrylonitrile, butadiene, or vinyl sulfone. For example, a Micheal-type addition reaction between a vinyl group and thiol is employed because it can be reacted with a weak base, like PBS, at physiological temp (37° C.) and pH (7.4).

The invention will be described by the following non-limiting example.

EXAMPLE

A PEG-based hydrogel, a widely used platform, along with a combination of bioinformatics and mechanical tissue testing methods, to adapt this material to recapitulate the integrin binding, matrix degradability, and bulk stiffness of bone marrow tissue. The hydrogel is functionalized using thiol chemistry with 20 bio-functional peptide sequences that can degrade in the presence of cell-secreted enzymes or that bind to cell surface integrins. These peptides were identified and quantified using an algorithm developed with data from the ProteinAtlas, and validated with mass spectrometry using bone marrow tissue from healthy donors (Uhlen et al. 2015). These ligands were incorporated, while maintaining physiological marrow tissue stiffness, and each was shown to have bioactivity. Human mesenchmal stem cells (hMSCs) in these materials have the highest capacity to differentiate into bone and have a heighten response to growth factors. Overall, the method that uses a top-down approach to filtering real tissue data to determine design parameters for tissue-specific materials. This technique is applied to the design of a novel in vitro bone marrow tissue, but we may be used to make a number of different in vitro tissues throughout the body.

Materials and Methods

Cell Culture

All cell culture supplies were purchased from Life Technologies unless otherwise noted. Human mesenchymal stem cells (MSC) were received through a material transfer agreement with Texas A&M University College of Medicine Institute for Regenerative Medicine at Scott &White funded by the NIH. MSCs from 3 three donors were cultured in Alpha minimum Essential medium (MEM), supplemented with 16.5% fetal bovine serum and 1% L-glutamine, and used between the 2nd and 6th passage. hTERT MSCs were provided from Dr. Junya Toguchida, the human breast cancer cell line MDA-MB-231 was provided from Dr. Shannon Hughes, and the highly metastatic variant. MDA-MB-231 1833 BOM cells, was provided by Dr. Joan Massagué. These were all cultured in Dulbecco's modified eagle's medium (DMEM), supplemented with 1% L-glutamine, 1% penicillin-streptomycin, 10% fetal bovine serum, 1% non-essential amino acids, and 1% sodium pyruvate.

Identifying Integrin Binding and MMP Degradable Proteins in Bone Marrow Tissue

Manual data mining was used to identify 42 integrin binding proteins and 45 MMP degradable proteins (FIGS. 9 and 10). The Protein Atlas was used to quantify the ECM proteins found in the bone marrow tissue. The histological score and FPKM were annotated for each protein with an average value recorded across all the patients scored. Then a list of integrin binding moieties or degradable peptide sequences was compiled for the majority of the proteins identified in marrow tissue.

Solid-Phase Peptide Synthesis

All peptides were synthesized on a CEM's Liberty Blue automated solid phase peptide synthesizer using Fmoc protected amino acids (Peptide Solutions). Resin was cleaved from the peptide by sparging nitrogen gas through a solution of peptide-resin and trifluoroacetic acid, triisopropylsilane, water, 2,2'-(Ethylenedioxy)diethanethiol at a ration of 92.5: 2.5:2.5:2.5% by volume, respectively (Sigma Aldrich) for 3 hours at room temperature in a peptide synthesis vessel (ChemGlass). Peptide solution was filtered to remove the cleaved resin and the peptide was precipitated out using dimethyl ether at −80 C (Fisher). Molecule mass was validated using a MicroFlex MALDI-TOF using α-cyano-4-hydroxycinnamic acid or synaptic acid as the matrix (Sigma). Peptides were purified to ≥95% on a VYDAC reversed-phase c18 column attached to a Waters 2487 dual λ adsorbable detector and 1525 binary HPLC pump.

The following sequences were synthesized:

GCGDGEA, (SEQ ID NO: 1)

GPRGGC, (SEQ ID NO: 2)

CSRARKQAASIKVAVADR, (SEQ ID NO: 3)

CSVTCG, (SEQ ID NO: 4)

CGGYSMKKTTMKIIPFNRLTIG, (SEQ ID NO: 5)

GCKQLREQ, (SEQ ID NO: 6)

GCDPGYIGSR, (SEQ ID NO: 7)

GRGDSPCG, (SEQ ID NO: 8)

GCRDRPFSMIMGDRCG, (SEQ ID NO: 9)

GCRDGPLGLWARDRCG, (SEQ ID NO: 10)

GCRDVPLSLTMGDRCG, and (SEQ ID NO: 11)

GCRDGPQGIWGQDRCG. (SEQ ID NO: 12)

The following sequences were purchased from GenScript at >96% purity:

CGGSVVYGLR, (SEQ ID NO: 13)

CGPHSRNGGGGGGRGDS, (SEQ ID NO: 14)

CGP(GPP)5GFOGER(GPP)5, (SEQ ID NO: 15)

CGGAEIDGIEL, (SEQ ID NO: 16)

GCRDIPESLRAGDRCG, (SEQ ID NO: 17)

GCGGQWRDTWARRLRKFQQREKKGKCRKA, (SEQ ID NO: 18)

GCRDVPLSLYSGDRCG, (SEQ ID NO: 19)

GCRDSGESPAYYTADRCG, and (SEQ ID NO: 20)

GCRDVPMSMRGGDRCG. (SEQ ID NO: 21)

Polymerization of 3D Bone Marrow Hydrogels 3D hydrogels were prepared with a 2K, 10K or 20K 4-arm PEG-maleimide (Jenkem Technology) that was reacted with the bone marrow peptide cocktail (FIG. 12) at a concentration of 1 mM in serum free media (pH 7.4) for 10 minutes being cross-linked at a 1:1 molar ratio with 50% 1.5 K linear PEG-dithiol (Jenkem Technology) and 50% of our MMP degradable cocktail (FIGS. 13A-13C) in 2 mM trietha-nolamine (pH about 7.4). Gels were polymerized in 10 µL volumes for 5 minutes before swelling in cell culture medium. Cells were seeded at 1000 cells/µL in 3D gel.

Hydrogel Mechanical and Structural Characterization

The effective Young's modulus was measured using indentation testing on 10 µL volumes of the 3D hydrogels. A custom-built instrument was used as described (Jansen et al., 2015; Chan et al., 2008). Bone marrow mechanical data was taken from Jansen et al. (2015). The force-indentation curves were analyzed using a Hertizan model modified by Hutchens et al. (2014) to account for dimensional confinement described by the ratio between the contact radius, a, and sample height, h (0.5<a/h<2) (Hutchens and Crosby, 2014). Relative error was used to account for deviation between sample force-indentation curves and the model. For theoretical mesh size calculations, hydrogels were polymerized and swelled in PBS for 24 hours, then weighed, lyophilized, and weighed again. The mesh size, $\xi$, was determined using the Flory theory modified by Canal and Peppas (1989).

Validation of Peptide Incorporation

The Measure-iT thiol kit was used to quantified unreacted thiols (Fisher). Buffers were prepared according to the manufacturers guidelines. Mono-functional peptides were incorporation at 1 mM in a 100 µL volume of PEG-maleimide for 10 min before reacting with 100 µL of the Measure-iT thiol working solution. Di-functional peptides were reacted with PEG-maleimide in 10 µL volumes for 10 minutes before reacting with 100 µL of the Measure-iT thiol working solution. Reduced Hydrogel reduction was done by immersing hydrogels in sodium borohydride (NaBH, Sigma) in water at a molar ratio of 4:1 NaBH to thiol for 4 hours before adding Measure-iT thiol working solution. All solutions or hydrogel supernatants were read at an excitation of 494 and emission of 517 within 5 minutes of the reaction. To quantify which peptides did not reaction, the supernatant from a hydrogel swollen in water for 2 hours was lyophilized, re-suspended in 1:1 acetonitrile and ultrapure water with 0.1% trifluoroacetic acid at a theoretical concentration 100 pmol/µL, assuming 0% of the peptides coupled to the hydrogel. Peptides were identified using a Bruker MicroFlex MALDI-TOF with either α-cyano-4-hydroxy cinnamic acid or synaptic acid as our matrix (Sigma).

The supernatant from a swollen hydrogel was lyophilized, re-suspended in 1:1 acetonitrile and ultrapure water with 0.1% trifluoroacetic acid at a theoretical concentration 100 pmol/µL assuming 0% of the peptides coupled to the hydrogel. Peptides were identified using a Bruker MicroFlex MALDI-TOF with α-cyano-4-hydroxy cinnamic acid or synaptic acid as our matrix.

ECM Protein Enrichment from Tissues

Tissue samples from healthy women between ages 45-60 were obtained from Cooperative Human Tissue Network funded by the NCI under IRB exempt status. Insoluble extracellular matrix proteins were extracted from 500 mg of tissue using the CNMCS compartmental protein extraction kit according to the manufacturers instructions (Millipore).

Mass Spectrometry

Two biological replicates were analyzed for bone marrow, brain, and lung tissue. The ECM-rich pellet was solubilized and reduced in 8 M Urea, 100 mM of ammonium bicarbonate, and 10 mM dithiothreitol (DTT) (Fisher Scientific) for 30 minutes at pH 8 and 37° C. Samples were alkylated with 25 mM iodoacetamide (Sigma) in the dark at room temperature for 30 minutes before the solution was quenched with 5 mM DTT. Prior to cleavage the solution was diluted to 2 M Urea with 100 mM ammonium bicarbonate at pH 8.

Proteins were cleaved via trypsin (Thermo Scientific) and lys-C endoproteinase (Promega), at a ratio of 1:50 enzyme to protein overnight (12-16 hours) at 37° C. Samples were cleaned and concentrated using a C18 column (Thermo Scientific). A reverse phase LC gradient was used to separate peptides prior to mass analysis. Mass spectrometry analysis was performed in an Orbitrap Fusion Tribrid (Thermo Scientific). Peptides were aligned against the Matrisome using the Thermo Proteome Discoverer 1.41.14 (Hynes and Naba, 2012). Parameters used trypsin as a protease, with 4 missed cleavage per peptide, a precursor mass tolerance of 10 ppm, and fragment tolerance of 0.6 Da.

MMP Degradation of Bone Marrow Tissue

MMP degradation assay was adapted from a protocol by Skjøt-Arkil et al. (2012). The ECM-rich pellet was solubilized in 8 M Urea at pH 8 and lyophilized in 200 µg aliquots. The lyophilized tissue samples were re-suspended in 100 mM Tris-HCL, 100 mM NaCl, 10 mM $CaCl_2$), and 2 mM ZnOAc at pH 8.0, MMP-1 (Sigma), MMP-2, MMP-3, MMP-9, MMP-13, MMP-14 (Abcam) and MMP-7 (Millipore) were activated according to the manufacturer's instructions and mixed individually 200 µg of tissue per 1 µg of either active enzyme, inactive enzyme, or, in the case where inactive enzyme was not available, MMP buffer was used as a control. Samples were mixed for 18 hours at 37° C., at which point the reaction was terminated with 25 µM of GM6001 (Millipore). Digested protein was run on a 4-29% Tris glycine polyacrylamide gel, stained using silver stain (Thermo Scientific), and imaged using the IN Genius Syngene Bioimaging platform (Frederick, Md.).

Competitive Binding Assay

Cells were seeded at 4000 cells per $cm^2$ in their normal growth medium after 30 minutes of pretreatment with individual peptides or the complete bone marrow cocktail. Bone marrow was dosed at a molar amount of 25 nmol/mL of medium and the molar amount dosed for each peptide was as follows: GRGDSPCG (SEQ ID NO:8)at 600 pmol/mL, CGPHSRNGGGGGGRGDS (SEQ ID NO:14), and GCGGQWRDTWARRLRKFQQREKKGKCRKA (SEQ ID NO:18) at 220 pmol/mL, $CGP(GPP)_5GFOGER(GPP)_5$ (SEQ ID NO:15), CGGSVVYGLR (SEQ ID NO:13), and GPRGGC (SEQ ID NO:2)at 160 pmol/mL, CSVTCG (SEQ ID NO:4) and CGGYSMKKTTMKIIPFNRLTIG (SEQ ID NO:5) at 100 pmol/mL, GCGDGEA (SEQ ID NO:1), CSRARKQAASIKVAVADR (SEQ ID NO:3), GCKQLREQ (SEQ ID NO:6), and CGGAEIDGIEL (SEQ ID NO:16) at 60 pmol/mL, and GCDPGYIGSR (SEQ ID NO:7) at 40 pmol/mL. Cells were imaged cells beginning 10 minutes after seeding in an environment controlled Zeiss Axio Observer Z1 microscope (Carl Zeiss) using an AxioCam MRm camera and an EC Plan-Neofluar 20× 0.4 NA air objective. Images were taken using Zen (Carl Zeiss) at five-minute intervals for 2 hours and cell areas were traced in ImageJ (National Institutes of Health).

Outgrowth of Cells on Beads

Cytodex1 microcarrier beads (Sigma) were swollen in sterile IX PBS (1 g beads/50 mL PBS) and autoclaved for 30 minute at 121° C. Flasks were coated with poly (2-hydroxyethy methacrylate) suspended in ethanol at 20 mg/mL and allowed to evaporate in a biosafety cabinet for 1 hour to make they non-adherent. hMSCs were seeded at 10-50 cells/bead in non-adherent flasks at a 0.1 mL of beads/mL of media. The flask was shaken every 1 hour for 4 hours to ensure coating unto beads. Cells were allowed to grow on beads for 72 hours before seeding into hydrogels. Breast cancer cells were suspended in 4° C., poly(N-isopropylacrylamide)-poly(ethylene glycol) (pNIPAAM-PEG, Cosmo Bio) reconstituted in cell culture medium at a density of 167,000 cells/mL of MDA-MB-231s. Gelation occurred after 5 min at 37° C., and gels were swollen in cell culture medium and grown into spheroids for 14 days. pNIPAAm gels were dissolved in cold serum-free DMEM (1% pen/strep) and spheroids transferred to conical tubes placed in ice so that spheroids would settle to the bottom. The supernatant was removed and the spheroids were re-suspended in PEG-maleimide solution. A ratio of 9 3D hydrogels were made for every 150 µL of pNIPAAM-PEG. Hydrogels were prepared with 4-arm PEG-maleimide at a 20 wt % cross-linked at a 1:1 molar ratio with 50% 1.5 K linear PEG-dithiol and 50% of each individual MMP degradable peptide sequence (FIGS. 13A-13C). Gels were imaged at days 1 and 3 and all image analysis was performed in ImageJ (National Institutes of Health).

Differentiation of hMSCs Across Biomaterials

Cells differentiation was assayed across 5 different biomaterials platforms: tissue culture polystyrene, glass coverslips. 2D PEG hydrogels, and 3D hydrogels with either bone marrow or RGD peptide functionality. Glass coverslips were prepared with 1 ug/$cm^2$ of the bone marrow peptide coupled to the surface as previously described by Barney et al. (2015). 2D PEG-phosphorylcholine (PEG-PC) hydrogels were prepared with bone marrow peptides coupled to the surface at 1 ug/$cm^2$ as described by Ngyuen et al. (2014). PC was kept at 17 wt % (0.6M) and PEG is added at 1.1 wt % (0.015 M) for a about 4 kPa hydrogel. Cells were seeded at a density of 40.000 cells per $cm'^2$ on 2D platforms and at a density of 2000 cells/µL in 3D platforms. For bone differentiation cells were provided cell culture medium supplemented with 10 mM beta-glycerolphosphate (Santa Cruz), 1 nM dexamethasone, and 50 µM L-Ascorbic acid 2-phosphate (Sigma). For fat differentiation cells were provided cell culture medium supplemented with 0.5 µM isobutylmethylxanthine, 0.5 µM dexamethasone, and 50 µM indomethacin (Sigma). Cells were maintained for 21 days with media changes every 3-4 days. After 21 days, cells and materials were fixed in 10% formalin (Fisher) prior to staining. 3D hydrogels were embedded in OCT (Fisher) and cut into 100 µm frozen sections prior to staining. Oil Red O staining was used to (Fisher) identify lipid formation and hydroxyapatite formation was identified using an Osteoimage mineralization assay (Lonza). Both staining procedures were done according to the manufacturers instructions.

L/D Stain hTERT MSCs or donor hMSCS were encapsulated into the 3D bone marrow hydrogel in different pH conditions of serum free DMEM. Hydrogels were swollen in cell culture medium and put in the incubator at 37° C. Cell viability was determined using a Live/Dead Viability/Cytotoxicity Kit (Fisher) according to manufacturers instructions 24 hours after encapsulation. Fluorescent images were taken on a Zeiss Cell Observer SD. Analysis of Live/Dead cell count was performed in ImageJ (version: 2.0.0) using the analyze particle tool in at least five replicates per encapsulation condition.

Statistical Analysis

Statistical analysis was accomplished using Graphpad's Prism v7.0a. Data are reported as mean±standard error. When noted, a two-tailed t-test was used. P-values <0.05 are considered significant, where p<0.05 is denoted with *, ≤0.01 with , ≤0.001 with *, and ≤0.0001 with ****.

Results

Figure 1B:
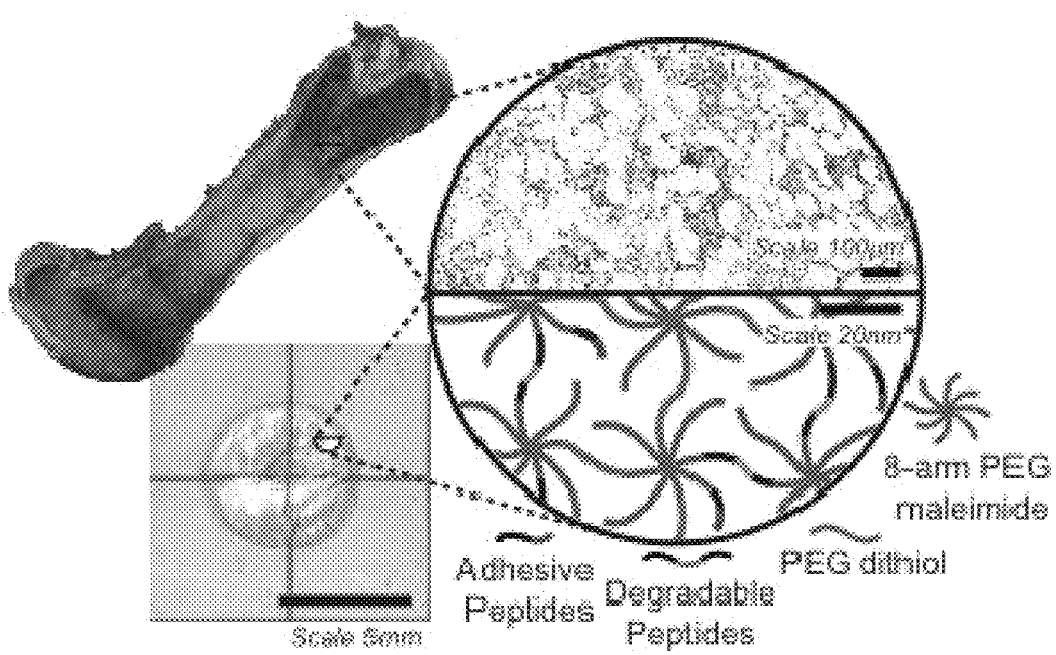
Figure 1C:
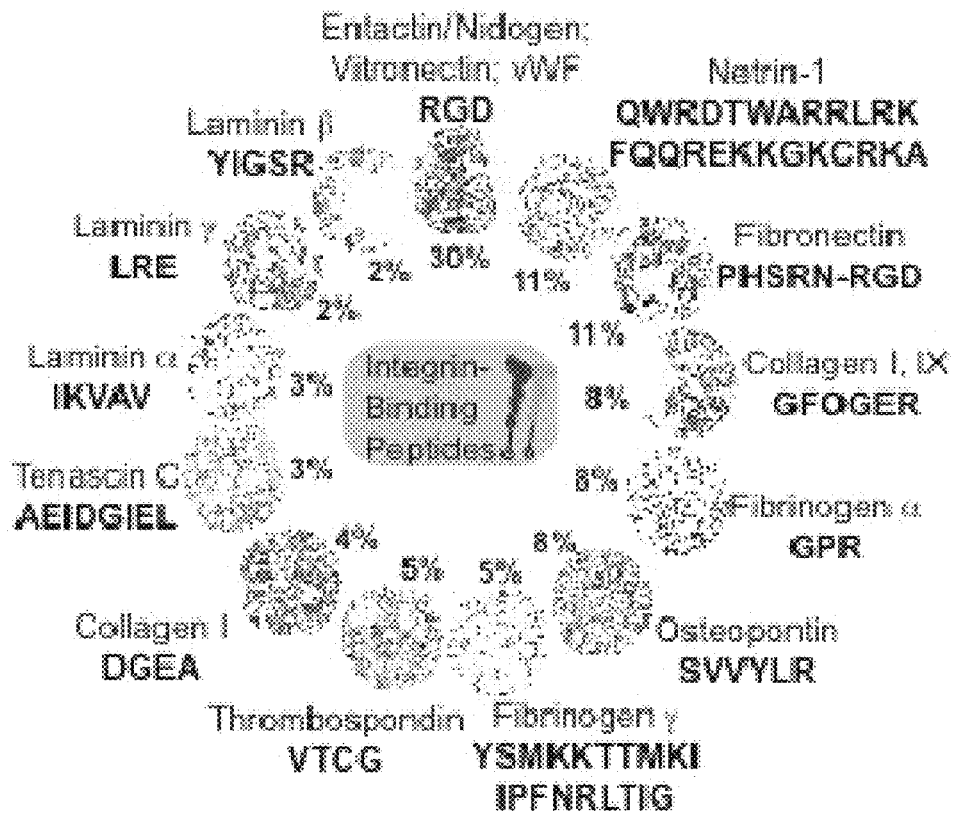
Figure 1D:
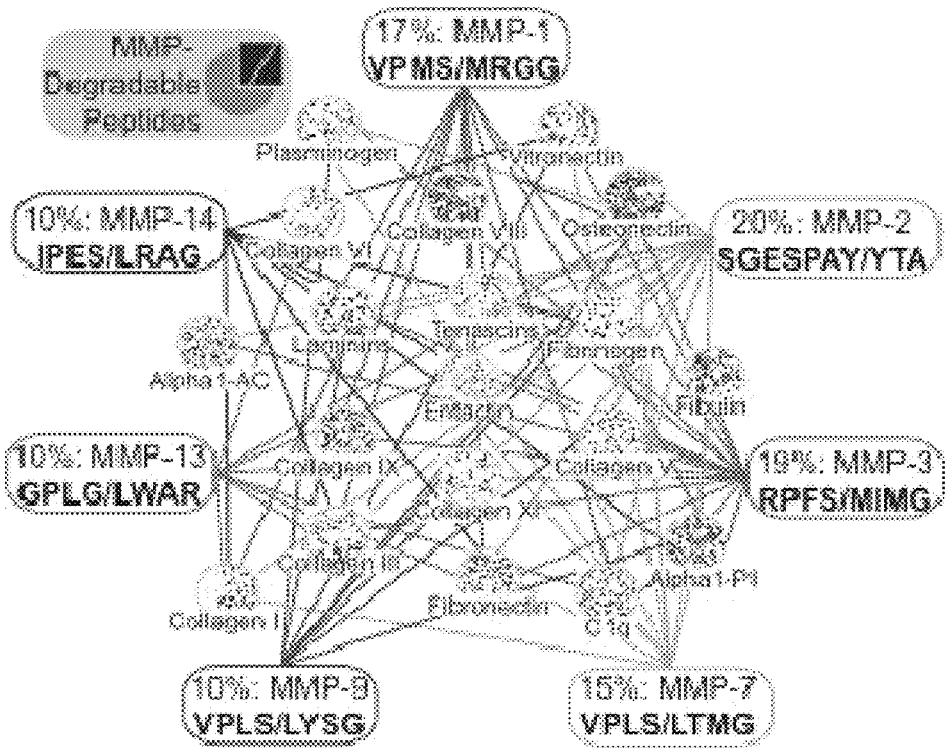
Figure 6A:
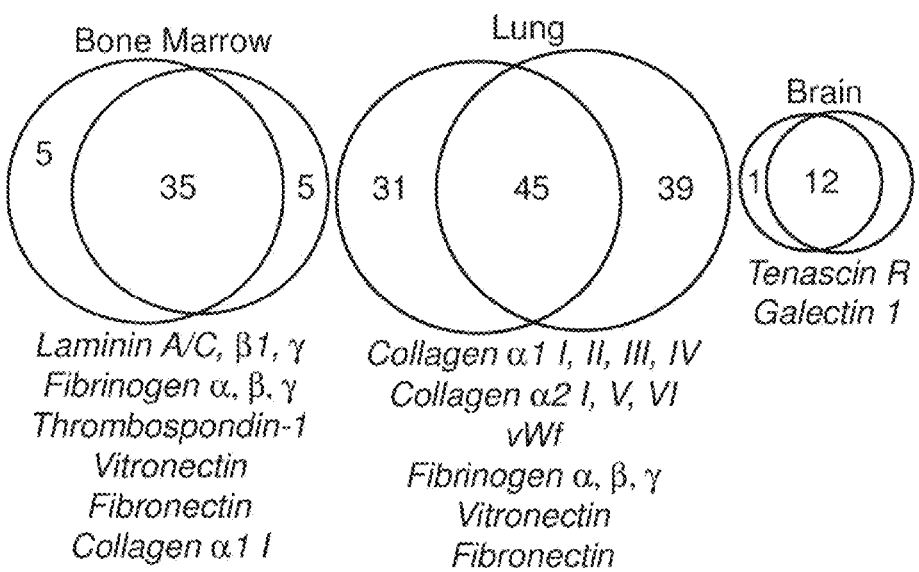
FIGS. 6A-6C. Validating Protein Atlas algorithm using real tissue. 6A) Venn diagrams depicting protein hits from two different healthy human donors analysed via LC-MS on for bone marrow, lung, and brain tissue. Proteins featured are some of the top integrin binding ECM proteins found in the respective tissue samples. 6B) The percentage of similarity the proteins found in LC-MS are to the peptide cocktail identified using histology data from the Protein Atlas (NS=no similarity). 6C) Silver stain of human bone marrow ECM in the absence (N) or presence of active MMP enzymes.
Figures 6B, 6C:
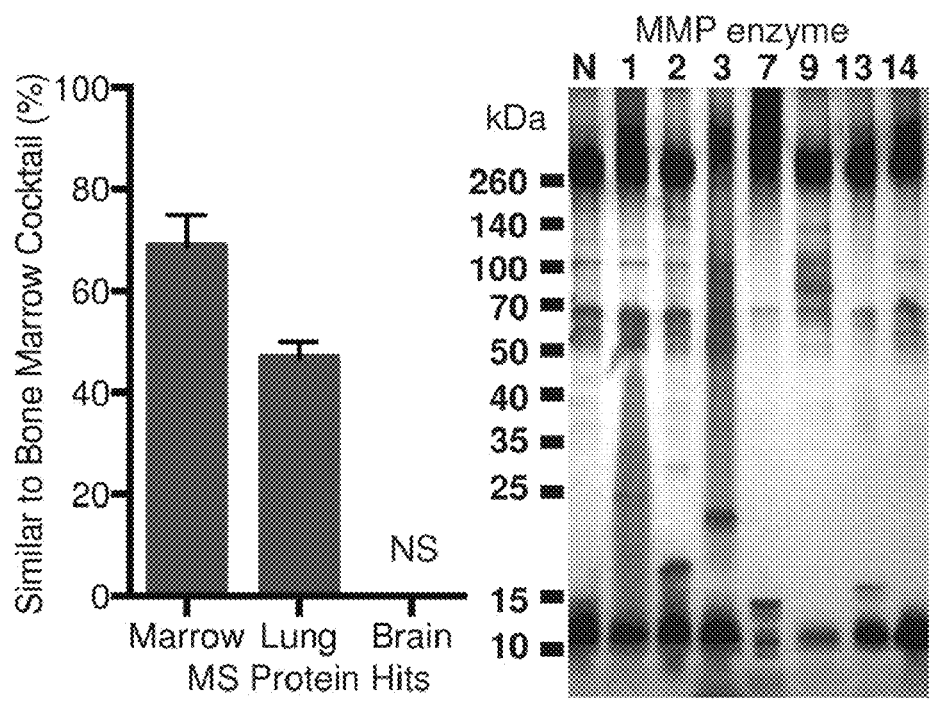

Bioinformatic Approach to Identifying the Chemical Properties of Human Bone Marrow Tissue Here, a top-down engineering approach was used to identify features of tissues that can be synthetically incorporated into a PEG hydrogel (FIG. 1A). Tissue was categorized into physical and chemical compartments (FIG. 1B). Physical features, like water content, elasticity, and resistance to force, can be measured using rheology and incorporated into the polymer network by adjusting the polymer-polymer distance or mesh size. Chemical properties were isolated to only extracellular matrix (ECM) proteins, of which there are about 300 (Naba et al., 2012). Of these proteins, about 90 proteins were identified that could be bound via integrin homo- and heterodimers or degraded by matrix metalloproteinases (MMPs) (FIGS. 9A-9B and 10A-10E). Then these proteins were identified in bone marrow tissue using the Protein Atlas (FIGS. 11A-11F) (Uhlen et al., 2015). To validate this approach, human ECM proteins in human bone marrow were enriched and run on liquid chromatography mass spectrometry (LC-MS) (FIG. 6A and FIG. 12). Protein hits from LC-MS in bone marrow tissue matched the marrow protein signature identified using the above criteria better than protein hits from LC-MS on human lung and brain tissue, indicating the algorithm could identify the unique protein signature of marrow (FIG. 6B). Additionally, this enriched ECM was used to validate that active MMP enzymes degrade human marrow (FIG. 6C). For the proteins found in human marrow, peptide motifs were identified that illicit integrin activity and degradable sequences that represent the degradable protein matrix (FIGS. 6D-6E, 13A-C and 14A-1-14C-2). The Protein Atlas histology scores were used to determine the quantitative amounts of each peptide to include in the final bone marrow cocktail for integrin-binding and MMP-degradable peptides.

Functional Validation of Peptide Moieties

Figure 2A:
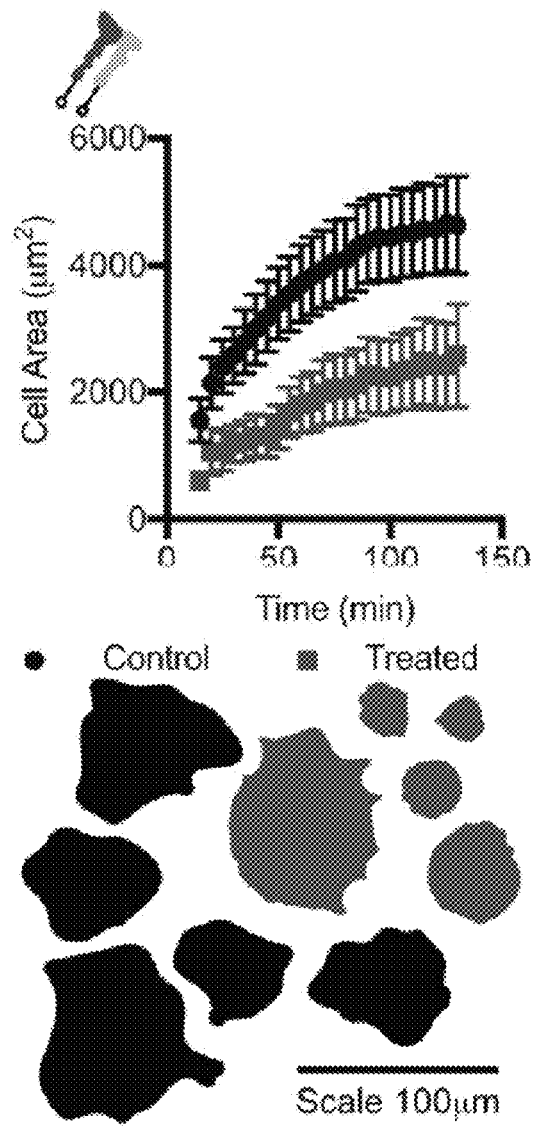
FIGS. 2A-2E. Peptide moieties can be bound and degraded by hMSCS. 2A) hMSC cell area over time for cells not treated (control, black) or pre-treated for 30 minutes (blue) with soluble integrin binding peptides and allowed to adhere to a surface coupled with the bone marrow peptide cocktail. Representative cell outlines of hMSCs 2 horrs after seeding. Error bars represent SEM. 2B) Heat map depicting the log 10 fold change in cell area at 2 hours compared to no treatment (NT) for each peptide moiety in the mimic across three donor hMSCs (1-3) and one cell line, hTERT MSCs (hT) (BM=bone marrow peptide cocktail) (N≥2, n≥40 per cell). 2C) Representative image of human mesenchymal stem cells (hMSCs) were seeded on cytodex beads (black outline) and encapsulated into a hydrogel with one MMP degradable crosslinker (Cell area=red, branch length=green). 2D) A box and whisker plot for the maximum branch length per bead in each hydrogel condition. 2E) Representative cell and bead traces in each hydrogel condition, where black is the bead (N=2, n≥15 per cell). Significance is determined using a two-tailed t-test where p=0.05
Figure 2B:
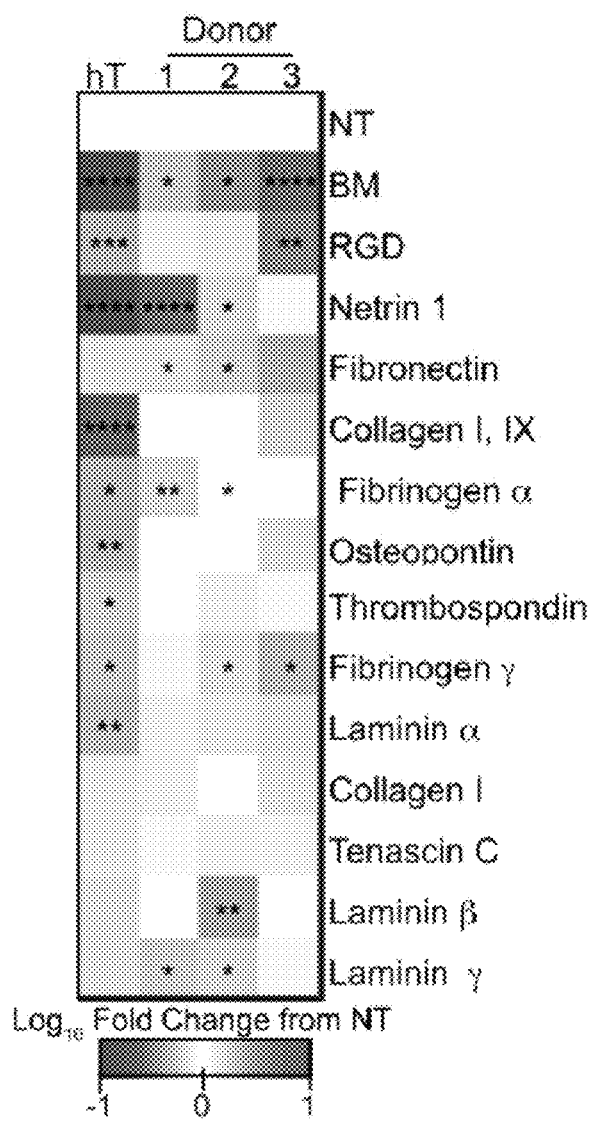
Figure 15A:
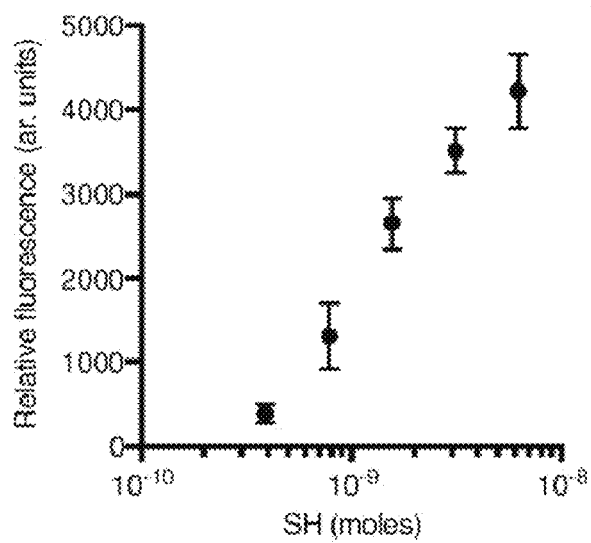
FIGS. 15A-15H. Modulating hydrogel properties and to best incorporate the bone marrow peptide cocktail. 15A) Relative fluorescence (excitation 494 nm, emission 517 nm) correlates with moles of thiol (SH) using the MeasureIT thiol assay. 15B) Unreacted moles of thiol versus polymer weight percentage (wt %) for a 4-arm 20K PEG (red). 15C) The effective Young's Modulus (EE) for hydrogels made with 4-arm PEG at 2K (gray), 10K (black), and 20K (red). 15D) Unreacted moles of thiols compared to the molar ratio of thiol to maleimide reactive groups for an 8-arm 20K PEG (green) and 4-arm 20K PEG (black) and the 15E) $E^{Eff}$ for the resulting 8-arm 20K PEG hydrogels. 15F) Representative images showing peptide solubility in DMSO versus PBS at pH 7.4. Error bars represent the SEM (N≥2, n≥3 for mechanical testing; N≥1, n≥3 for unreacted thiol assay). 15G) The percentage of unreacted thiols when mono-functional peptides suspended in DMSO (black) or PBS at pH 7.4 (blue) are added at a concentration of 1 mM to a solution of PEG dissolved in 2 mM TEOA (filled circles) or not (open circles) in PBS at pH 7.4. 15H) The percentage of unreacted thiols after soaking reacted hydrogels in a reduction solution of sodium borohydride for 2 hours.
Figure 15B:
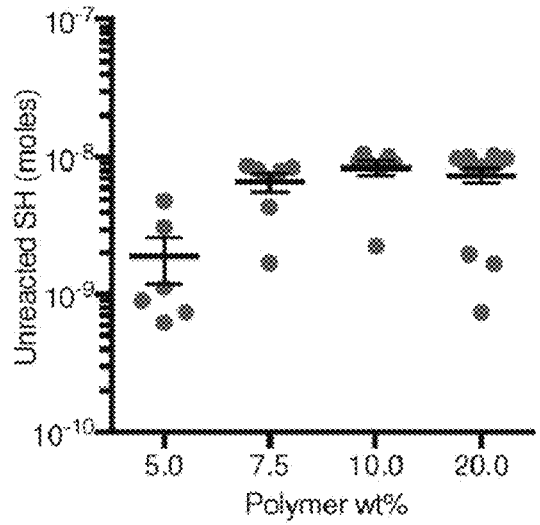

To validate each integrin-binding peptide was functional, hMSCs were pre-treated with soluble peptides and allowed to adhere to a glass surface with the bone marrow integrin-binding peptide cocktail covalently bound. In treated peptide conditions we observed a decrease in cell adhesion, indicated by cell blebbing and the spherical shape (Berre et al., 2005), which was quantified via cell area (FIG. 2A). Across three donor hMSCs and one immortalized cell line (hTERT MSCs), the majority of peptides decreased cell adhesivity to the surface (FIG. 2B). The hMSC cell line was more responsive to peptide treatment than the donor cells, and this did not seem to be because of non-treated cell size (FIG. 7A). The collagen I and tenascin C peptides were not significantly bound in any case, so two breast cancer cell lines were screened and it was found this non-binding was likely a feature of the hMSC cell type (FIG. 15B). Importantly, all cell lines decreased adhesion when dosed with the bone marrow peptide cocktail (FIG. 2B and FIG. 7A). The decrease in cell adhesion was likely a result of the soluble peptide being bound to and competing for integrins on the cell surface. Cells could only bind to the coverslips with covalently bound peptides and protein did not readily bind to the coverslip in the experimental time frame, so it was presumed that cells are only binding to what was presented (FIGS. 7A-7B). All together, these results indicate that cells can bind each peptide in the mimic.

Figure 2C:
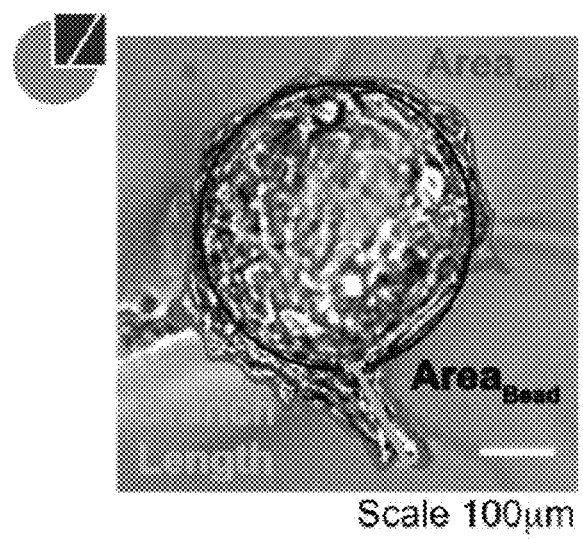
Figure 2D:
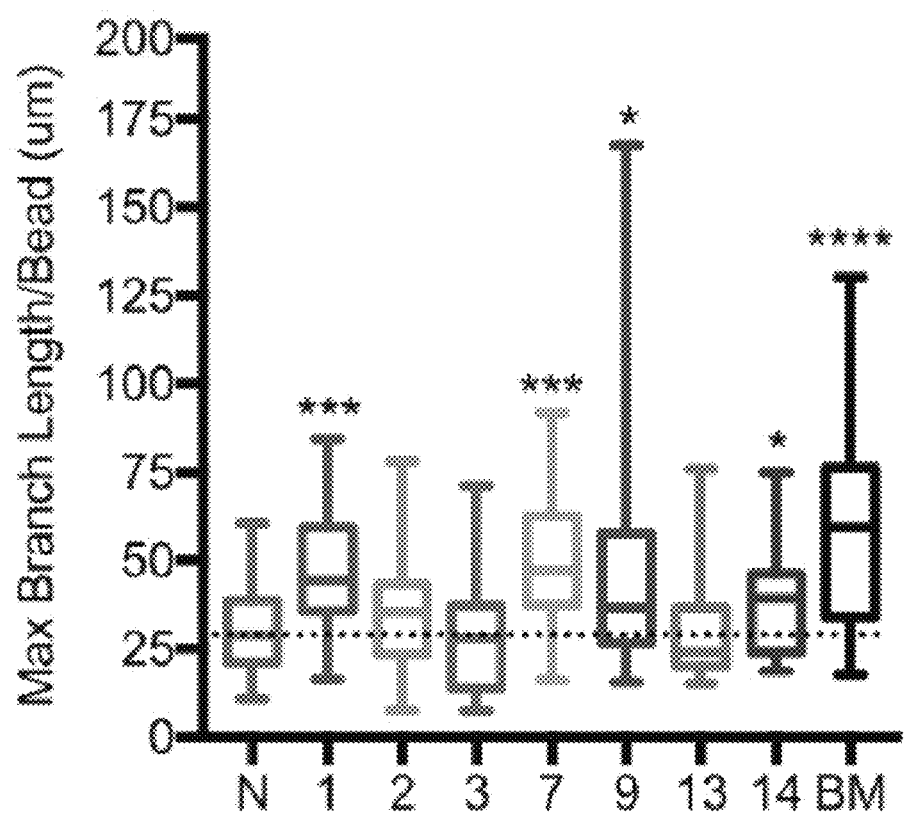
Figure 2E:
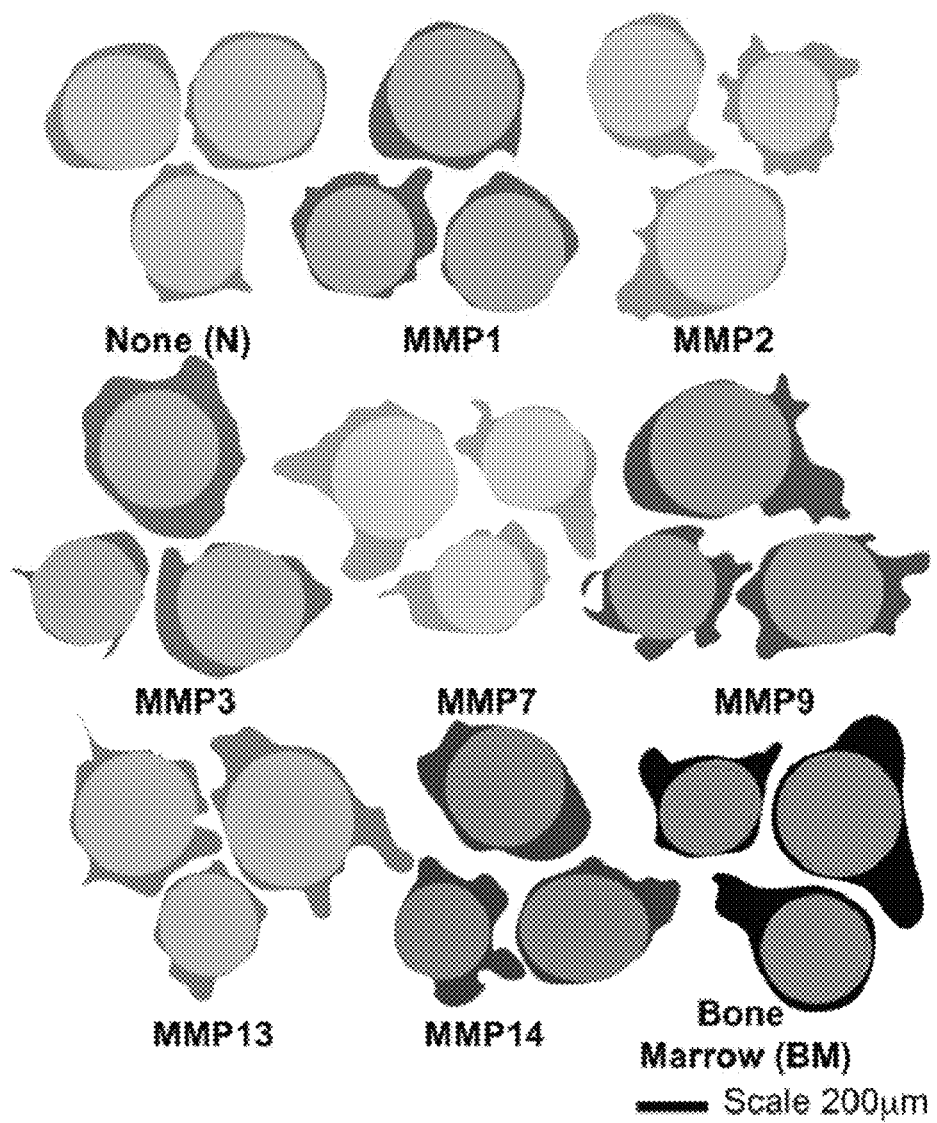

To validate that each crosslinker could degrade in a hydrogel. hMSCs were coated onto beads and encapsulated in hydrogels made with a single crosslinker to validate the crosslinker's ability to degrade in a hydrogel (FIG. 2C). When degradable peptides were present, cells were able to branch further into the surrounding material (FIGS. 2D-2E). No significant hMSC cell branching was observed in gels crosslinked with peptides designed for MMP 2, 3, and 13 over the control, non-degradable, crosslinker. Using a different cell line, degradation in the MMP-13 crosslinked gel was observed, but again not with the MMP 2 and 3 peptides (FIGS. 8A-8B). The ability for these MMP peptides to degrade has been shown with a chick arotic cells for the MMP-2 crosslinker and myofibroblasts for the MMP-3 crosslinker, so potentially the cells used here do not readily express these MMPs (Patterson et al., 2010). Additionally, MMP expression and activation is tightly regulated and they are often only seen at certain stages of disease progression or when specific cytokines or growth factors are present (Loffel et al., 2011). In a gel crosslinked with the bone marrow MMP-peptide cocktail, the highest potential for hMSCs to branch was observed, indicating this combination allows bone marrow cells to degrade this hydrogel over time.

Optimal Conditions for Coupling Tissue-Specific Peptides

No group has apparently ever attempted to put 20 different peptides into a PEG hydrogel before. Thus, it was important to investigate the conditions for coupling this diverse cocktail and to show all these peptides are in the hydrogel. The peptides are coupled to the matrix using a Michael-type addition reaction. The maleimide functionality was selected as the Michael-type acceptor, because the maleimide-thiol reaction has been shown to provide the most efficient incorporation of ligands and largest range of bulk properties in similar PEG hydrogels (Phelps et al., 2012). The Michael-type donor for this reaction is a thiol, so a thiol quantification assay was used to identify loose thiols in solution post-polymer coupling (FIG. 6A). A number of parameters that regulated the efficiency of this crosslinker incorporation were identified, including polymer wt % and percentage of crosslinking, however these properties also change the Effective Young's modulus of the hydrogel (FIG. 6C). This tradeoff was overcome slightly by using an 8-arm PEG over a 4-arm PEG which increased crosslinker coupling without increasing moles of unreacted thiol (FIG. 7D).

Figure 3A:
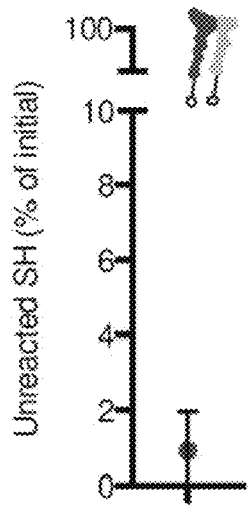
FIGS. 3A-3H. Bone marrow peptides couple to the hydrogel at the expected concentration. 3A) The percentage of unreacted thiols when mono-functional peptides suspended in PBS at pH 7.4 are added to a solution of PEG dissolved in PBS at pH 7.4. 3B) The percentage of unreacted thiols 10 minutes post-crosslinking an 8-arm PEG hydrogel at a 1:1 molar ratio of thiol to maleimide. Error bars represent the SEM (N≥1, n≥3). MALDI-TOF spectrum (top) and identified peptide peaks (bottom) for the 3C) and 3D) bone marrow monofunctional peptide cocktail, 3E) and 3F) the bone marrow difunctional peptide crosslinkers, and 3G) and 3H) the supernatant of a bone marrow hydrogel swelled for 4 hours in PBS.
Figure 3C:
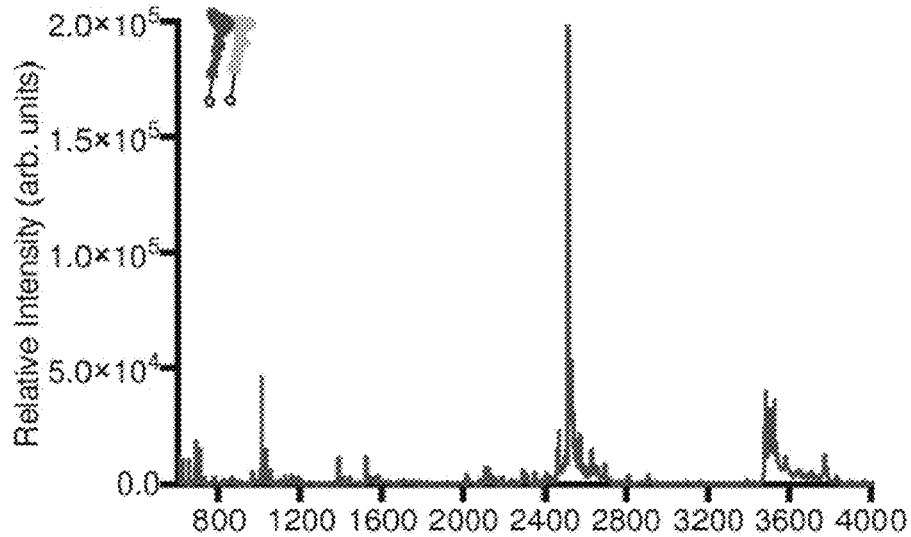
Figure 3B:
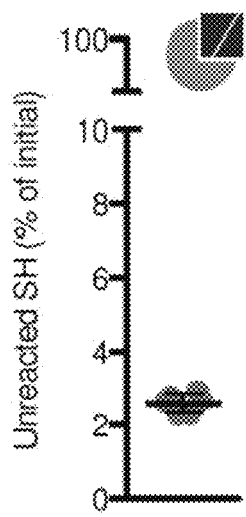

Using an 8-arm PEG at 20 wt % gel, >98% coupling of mono-functional and >95% coupling of di-functional peptides were obtained (FIGS. 3A-3B). Optimal coupling for integrin-binding peptides was in PBS at pH 7.4, even though the peptide cocktail was significantly less soluble in this buffer than each individual peptide alone (FIG. 6F). Peptide solubility could be increased using DMSO, but this solvent reduced the coupling efficiency for peptides to the matrix even when a strong base like TEOA was included in the reaction buffer (FIG. 7G). Because thiols are known to readily form di-sulfide bonds, the formed hydrogel was placed in a reduction buffer of sodium borohydride. This did not drastically increase the number of free thiols in solution, indicating that >90% the material bonds are likely from the Michael-type addition reaction (FIG. 2H).

MALDI-TOF, which is sensitive to the pmol, was used to identify which peptides don't couple to the hydrogel. All the integrin-binding and MMP-degradable peptides could be identified when in the cocktail solution, with the exception of DGEA (SEQ ID NO: 25) and AEIDGIEL (SEQ ID NO: 24), both which are negatively charged (FIGS. 2E-2F and 16A-16C). AEIDGIEL (SEQ ID NO: 24) does not easily ionize and cannot be identified when combined with other, non-charged peptides (FIGS. 16C-16F). After peptide coupling and hydrogel formation only 2 peptides were identified in the supernatant at a significantly reduced intensity, indicating they were there at very low concentrations. Taken together, this data suggests the vast majority of our peptides are displayed in the hydrogel at the concentration expected.

Matching PEG Bulk Mechanics to Bone Marrow Tissue

Figure 15C:
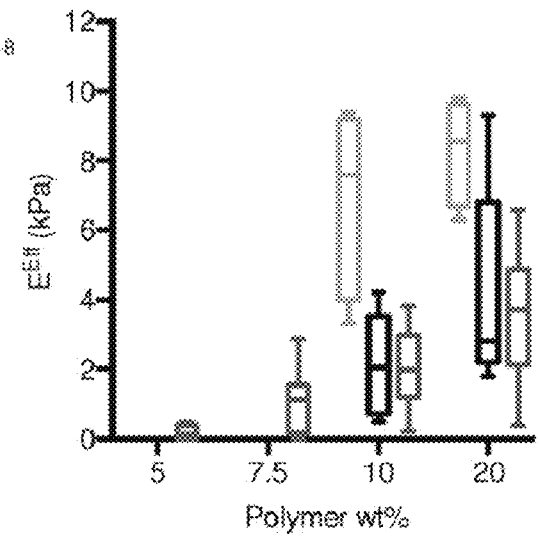
Figure 15D:
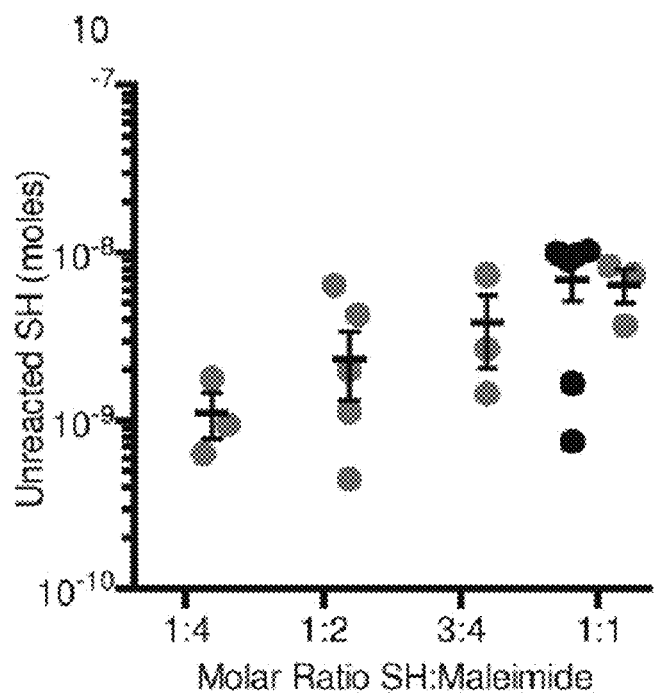
Figure 15E:
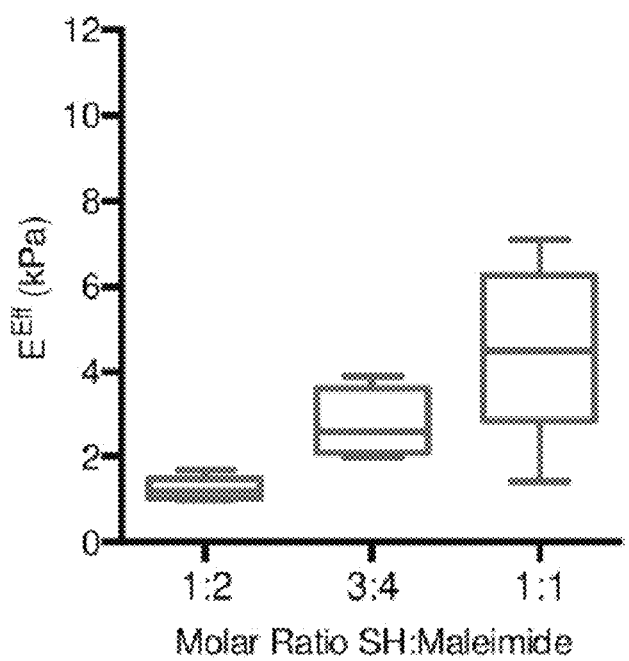
Figure 15F:
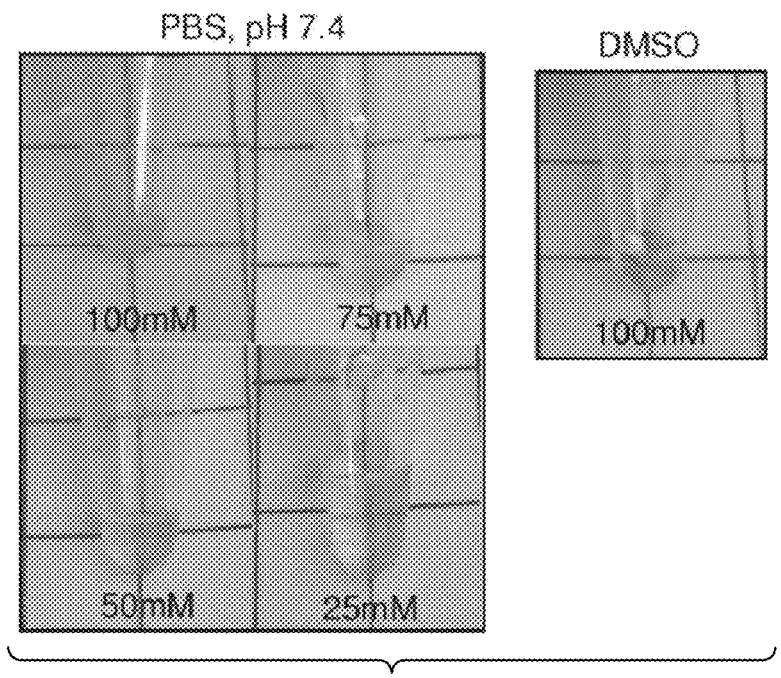
Figure 15G:
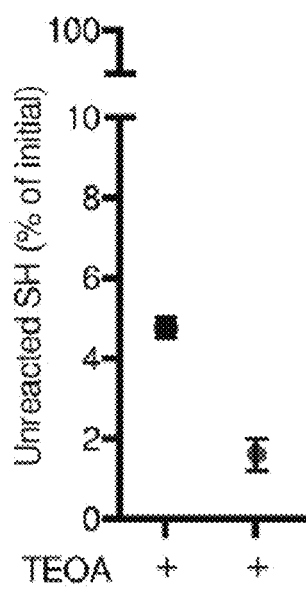
Figure 15H:
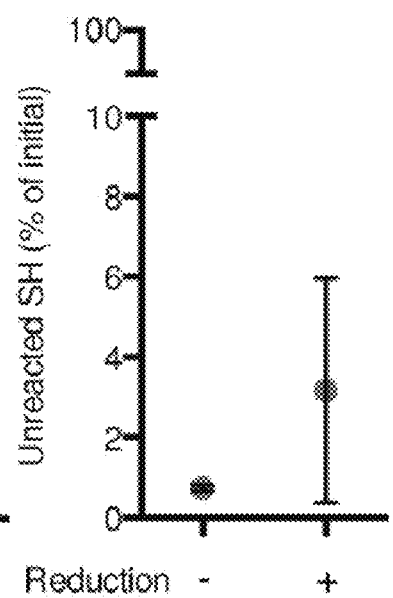
Figure 16A:
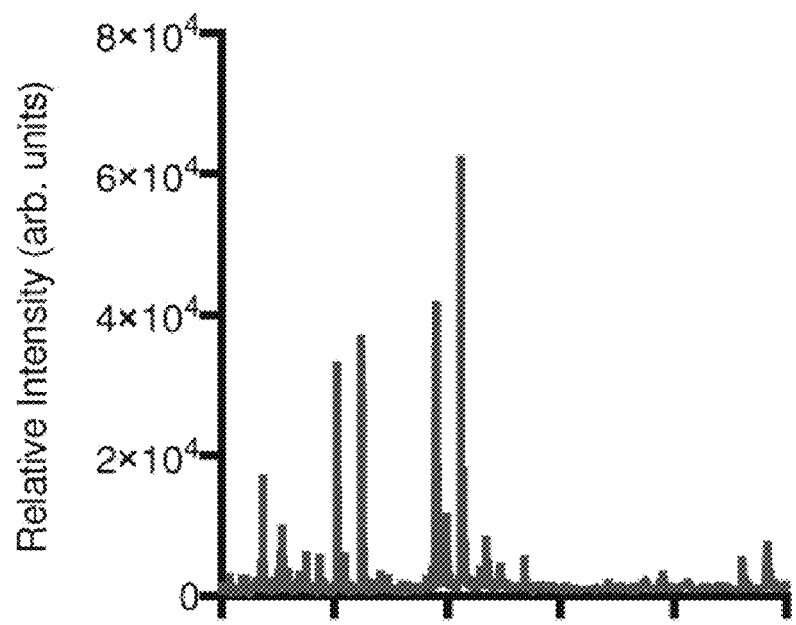
FIGS. 16A-16F. Peptide charge limits detection using MALDI in the peptide cocktail. 16A) MALDI spectrum and 16B) identified peptide peaks for 250 pmol of the bone marrow peptide cocktail using 10 mg/mL of 2,5-dihydroxybenzoic acid as a matrix. MALDI spectrum with 16C) 250 pmol of the bone marrow peptide cocktail, 16D) 250 pmol of the bone marrow peptide cocktail and 60 pmol of CGGAEIDIEL (SEQ ID NO:16), or 16E) 60 pmol of CGGAEIDIEL (SEQ ID NO:16) using 10 mg/mL of α-cyano-4-hydroxycinnamic acid as the matrix. 16F) The peaks identified as peptides in the MALDI spectrums from 16C-16E.
Figure 16B:
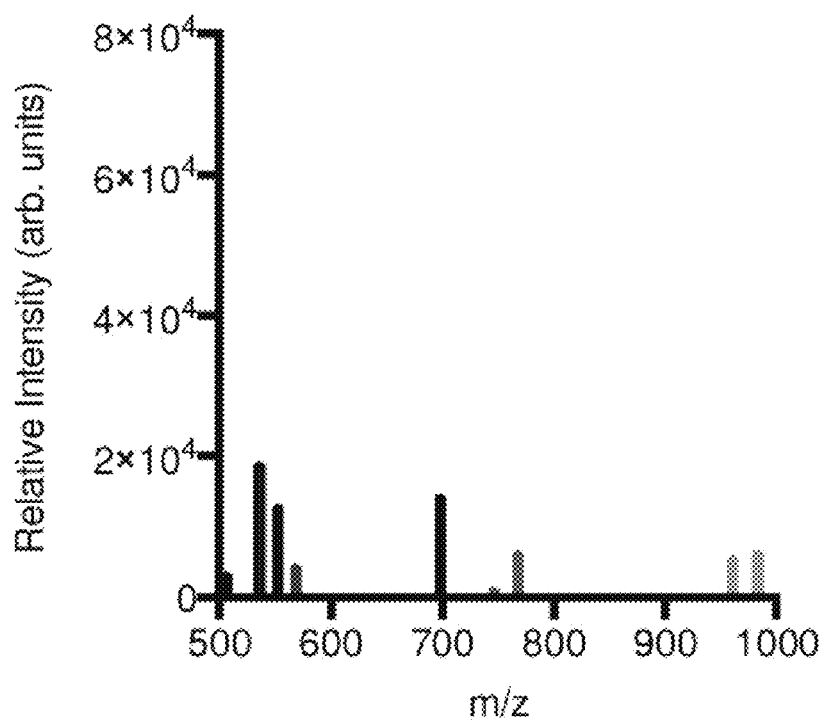
Figure 16C:
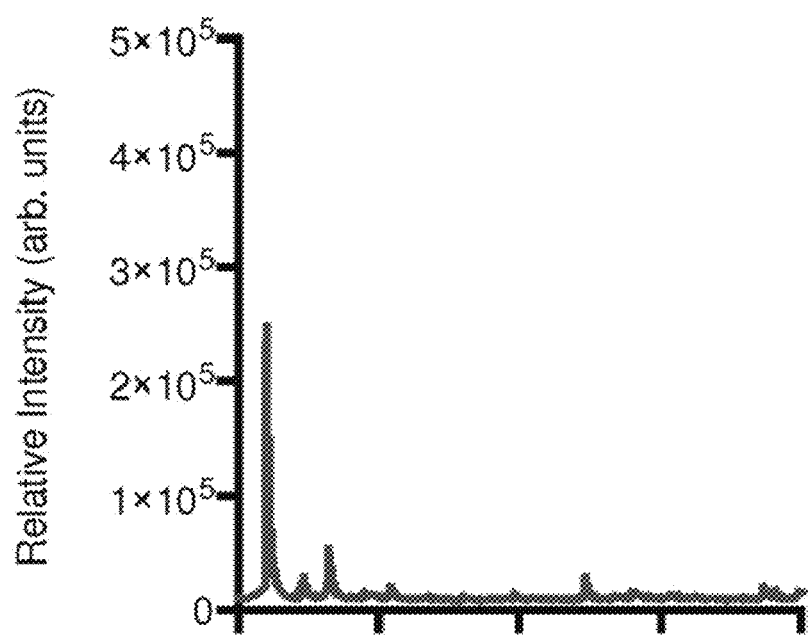
Figure 16D:
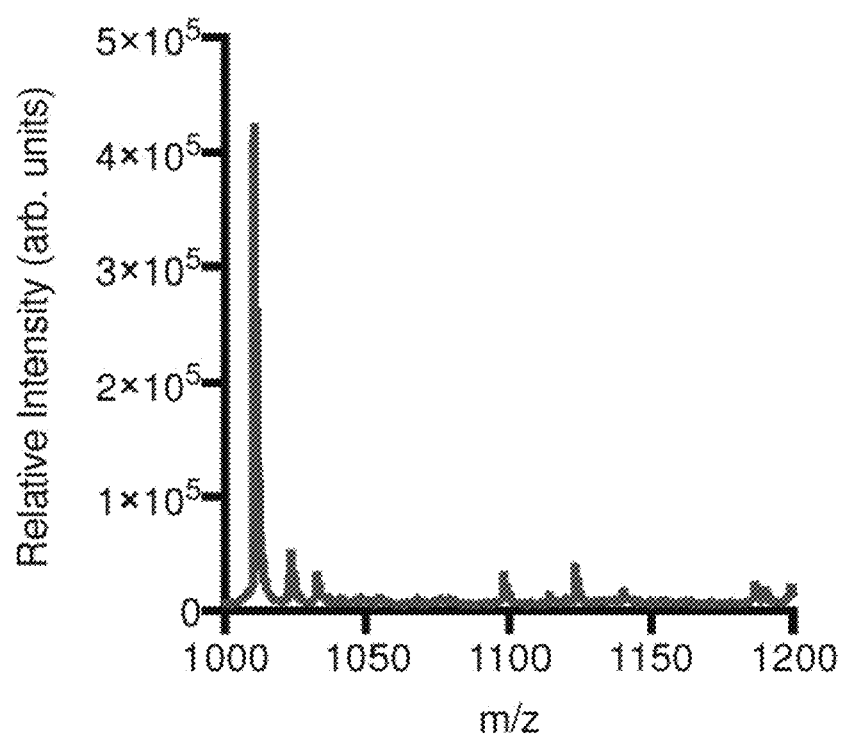
Figure 16E:
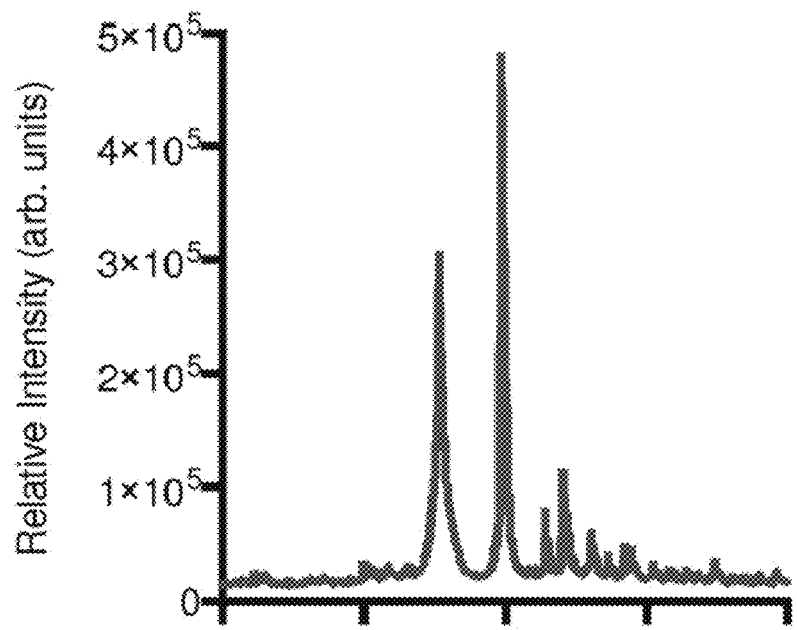
Figure 16F:
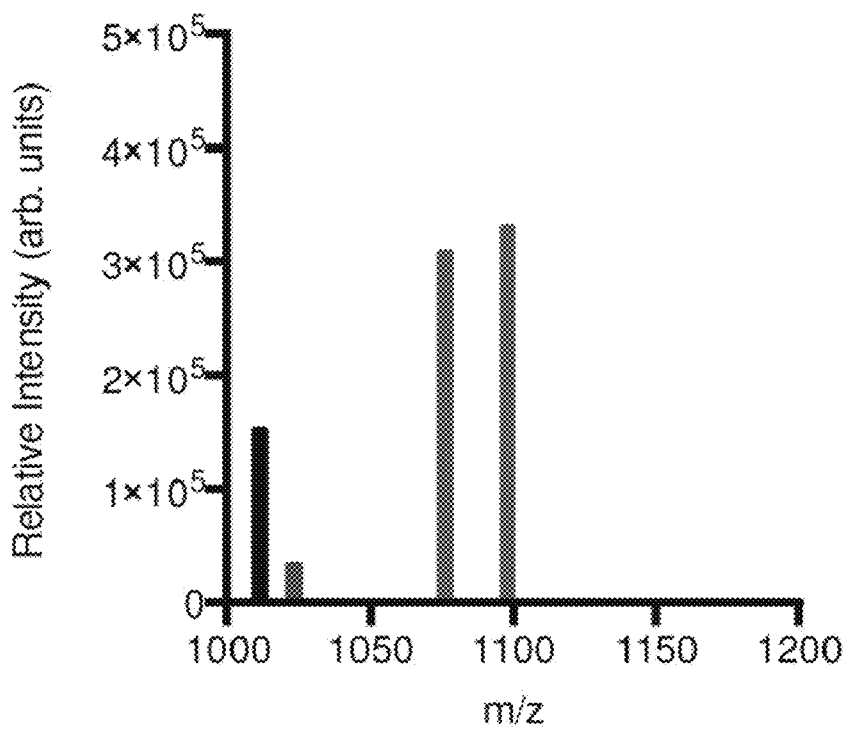

The mechanical properties of engineered materials has been shown to influence the migration and differentiation of marrow-derived stromal and hematopoietic stem cells. These studies, and others, all highlight an important role for the mechanical properties of bone marrow tissue to direct stem cell fate and function. Porcine bone marrow has an average stiffness of 4.4±1.0 kPa at physiological temperature (FIG. 4A). The hydrogel bulk material properties of PEG can be matched to that of bone marrow tissue by tuning the polymer arm length, arm number, and crosslinking density (FIGS. 15C and 15E). PEG hydrogels can be adapted to span the range of stiffness observed in bone marrow tissue, e.g., a 20 wt % 8-arm 20K PEG hydrogel matches the average stiffness of marrow (FIG. 15C). In fact, recent work showed that hematopoietic progenitor populations are maintained in the presence of fibronectin on this same elastic modulus (Choi et al., 2017).

Figure 3D:
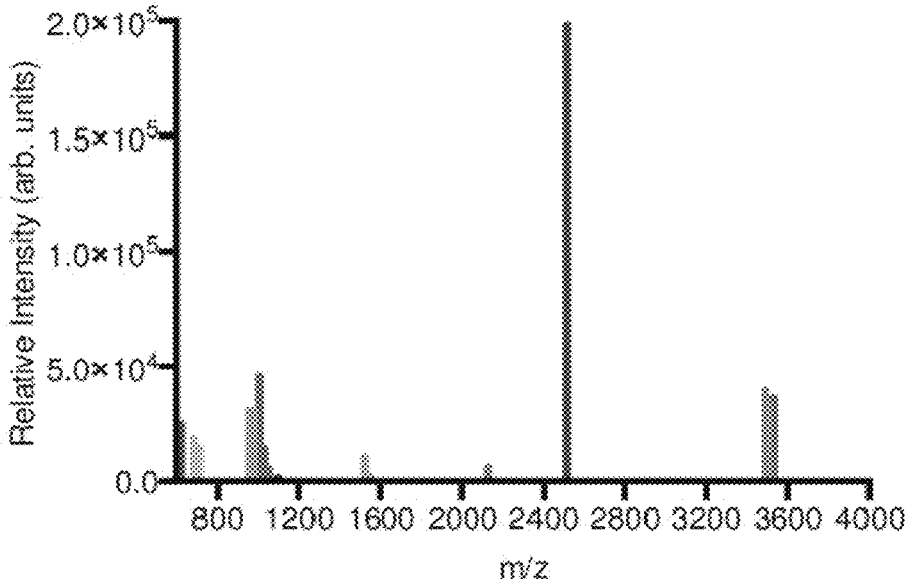
Figure 3E:
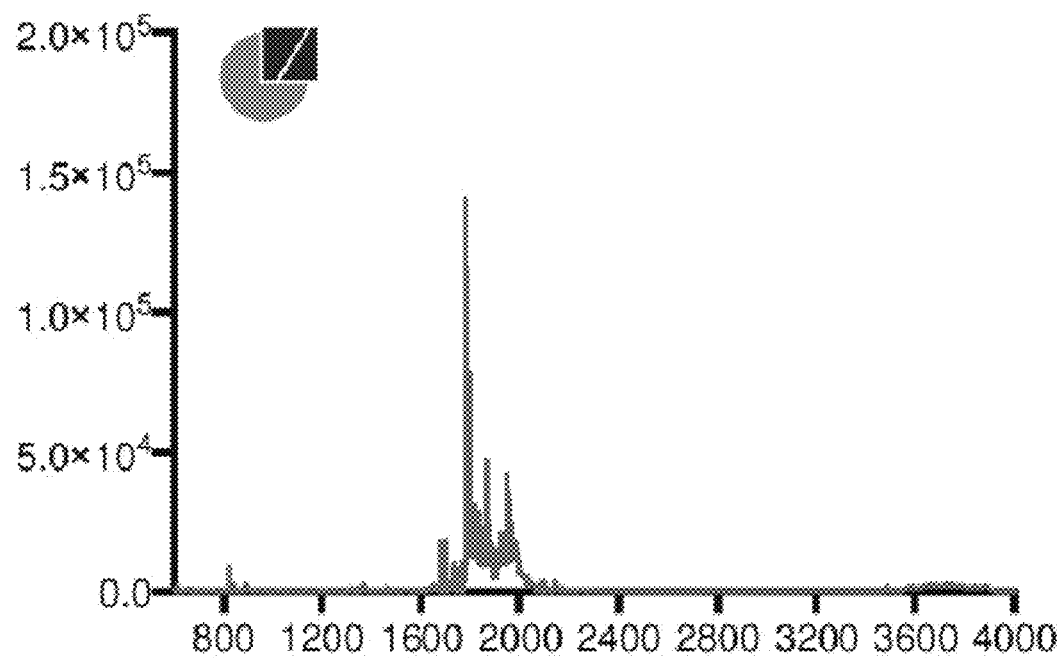
Figure 3F:
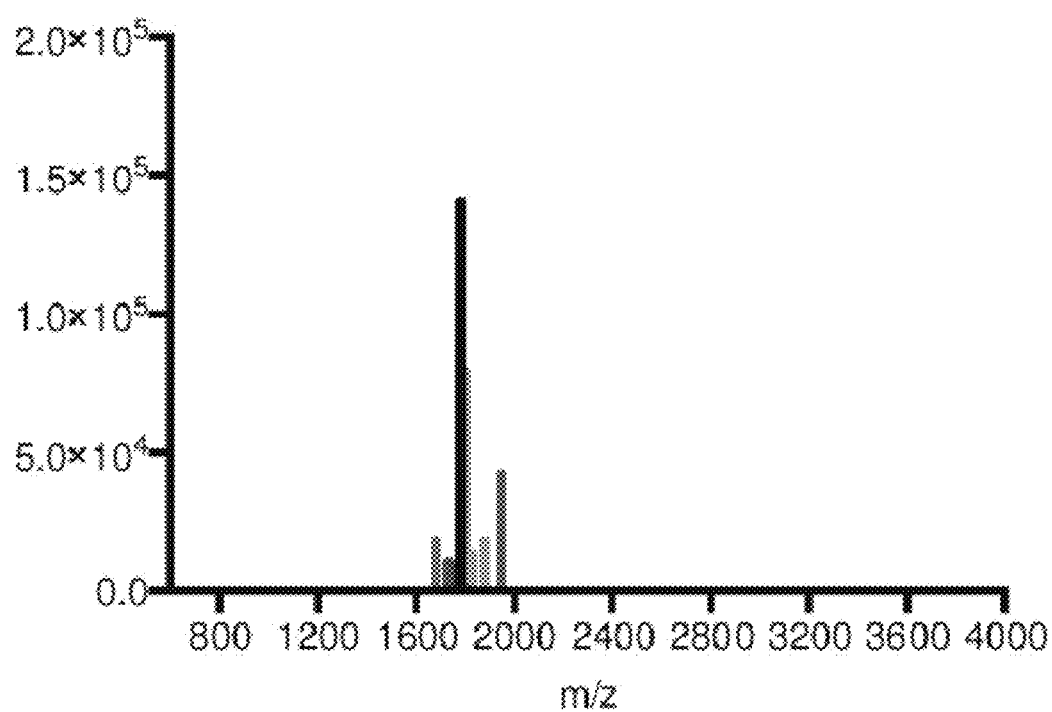
Figure 3G:
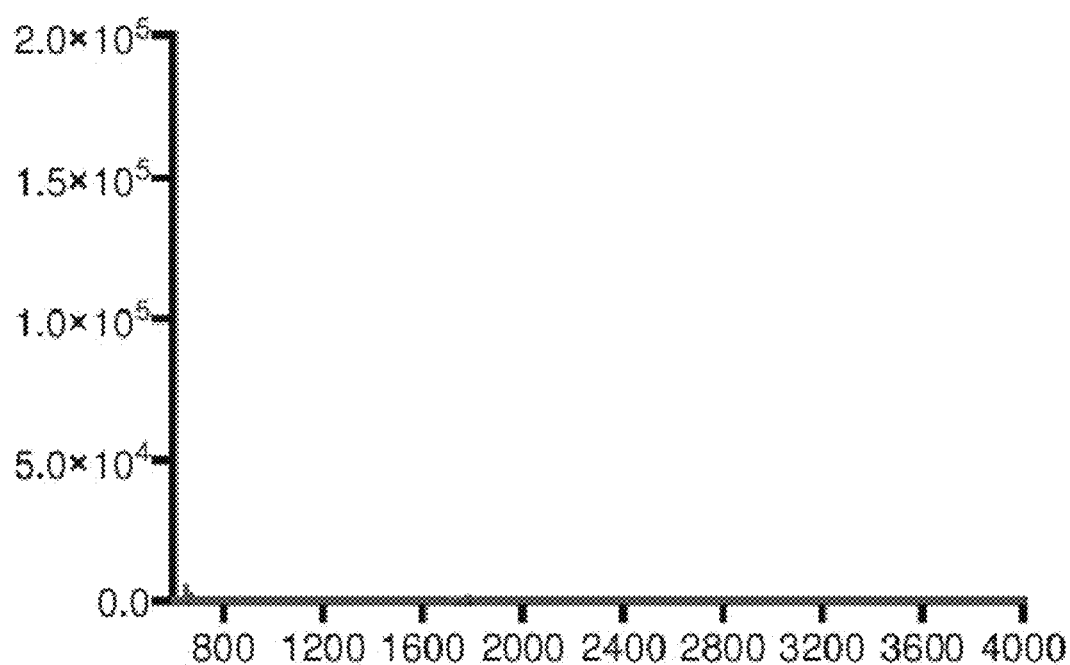
Figure 3H:
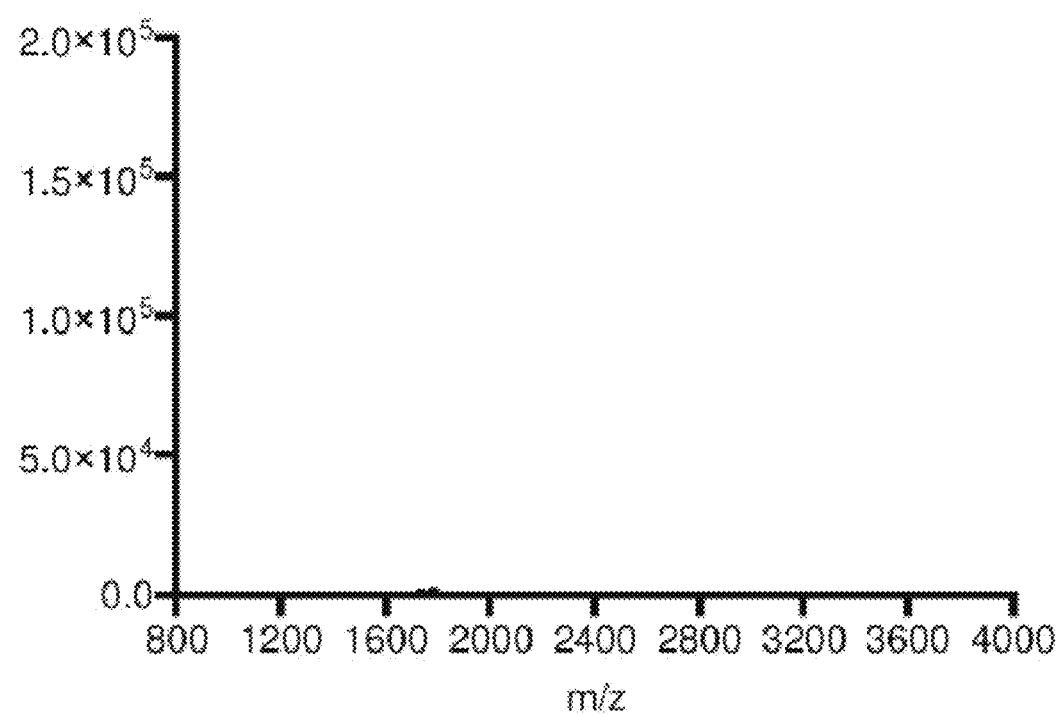
Figure 4F:
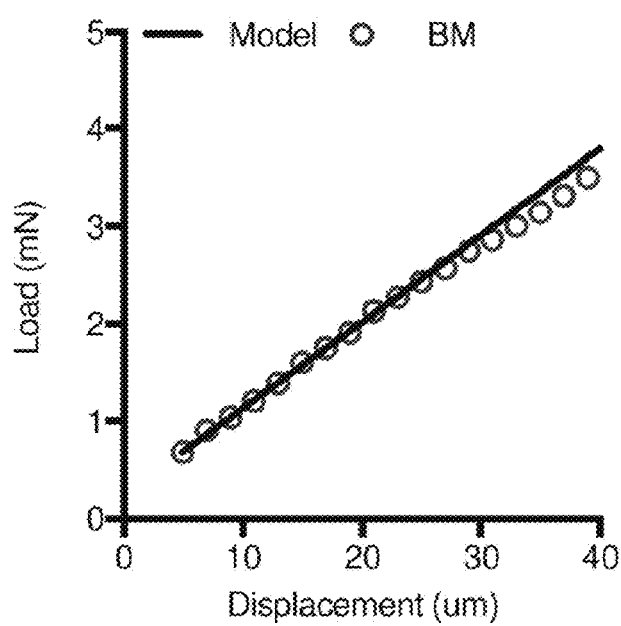
Figure 4G:
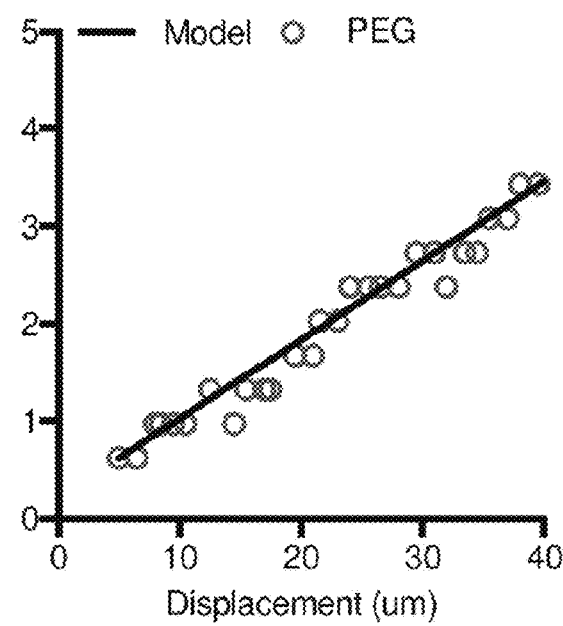

Incorporation of the MMP peptide crosslinkers did not significantly reduce the material stiffness (FIG. 4B) and mono-functional integrin-binding peptides could be added up to 4 mM without significantly changing bulk modulus of the material (FIG. 4C). A 2 mM concentration of integrin-binding peptides achieved significant hMSC spreading (FIGS. 3D-3E). Together this indicates that PEG is a good model for the bulk compressive properties of marrow. For the bone marrow hydrogel, a 20 wt %, 8-arm 20K PEG coupled with 2 mM of peptides was used to provide a selected optimal stiffness, peptide incorporation, and cell spreading. Recent work added stress relaxation to alginate gels because many tissues, like marrow, are viscoelastic and these properties can regulate stem cell fate (Chaudhui et al., 2015). Bone marrow is a benign elastic tissue (Jansen et al., 2015). Using the previously published indentation data, the compressive properties were compared for both porcine bone marrow and the PEG hydrogel. Both closely follow a Hertzian model (FIGS. 4F-4G), suggesting that PEG is an appropriate model for the compressive properties of bone marrow.

Figure 5A:
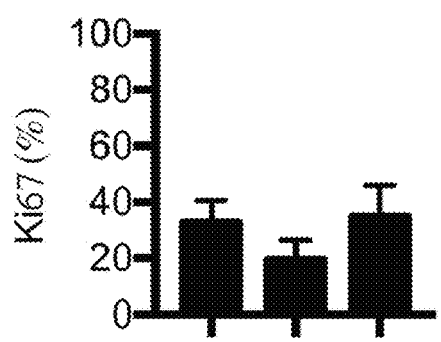
FIGS. 5A-5H. The bone marrow hydrogel is the 3D platform for maintaining the hMSC differentiation capacity. Staining for 5A) Ki67 5B) p21 5C) b-gal and 5D) alpha-smooth muscle actin, in a 5E-5F) hydrogel with no degradability and 2 mM RGD (RGD) or the bone marrow hydrogel (BM). 5G) Log 10 of cell metabolic activity 3 days after cell encapsulation in the bone marrow hydrogel compared to an RGD hydrogel for all donor cells. Each growth factor was dosed at 20 ng/mL in cell culture medium. 5E) Oil red or 5F) osteoimage differentiation capacity normalized to the RGD hydrogel. 5H) Schematic adapted from Barney et al., 2015 to compare how the two hydrogels impact hMSC phenotypes.
Figure 5C:
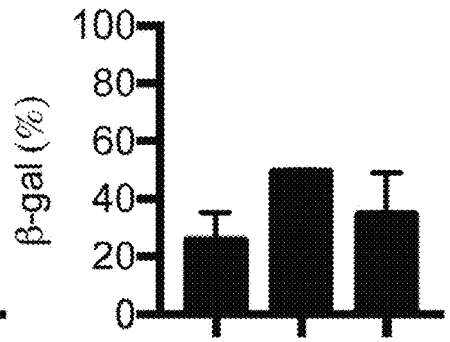
Figure 5B:
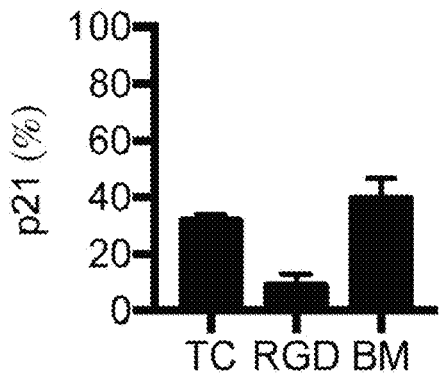
Figure 5D:
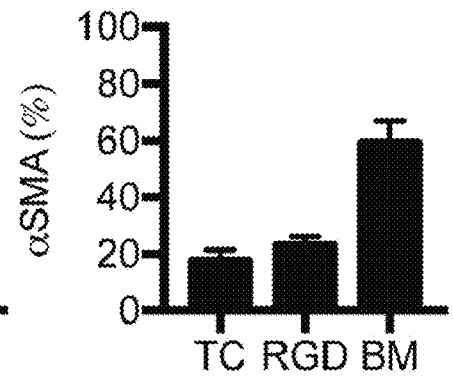
Figure 5E:
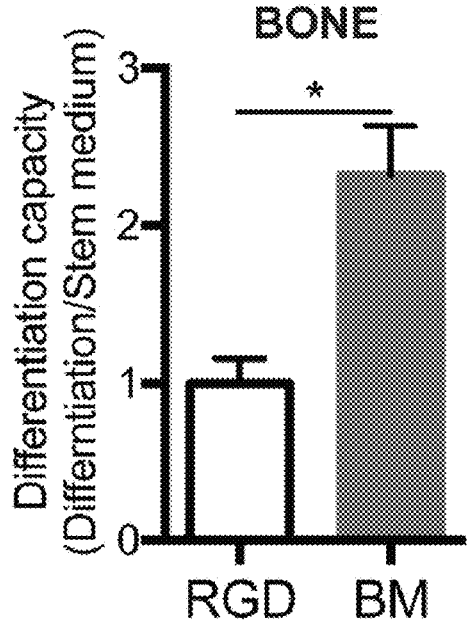
Figure 5F:
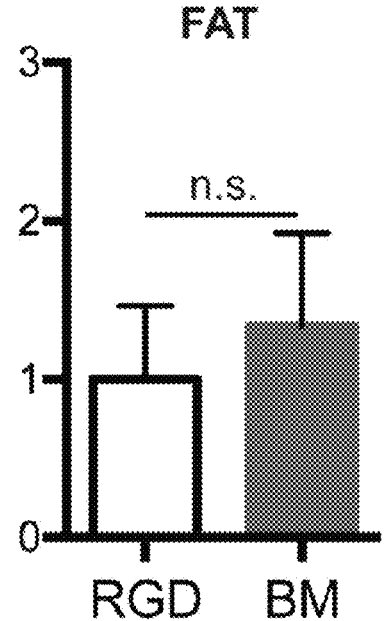
Figure 5G:
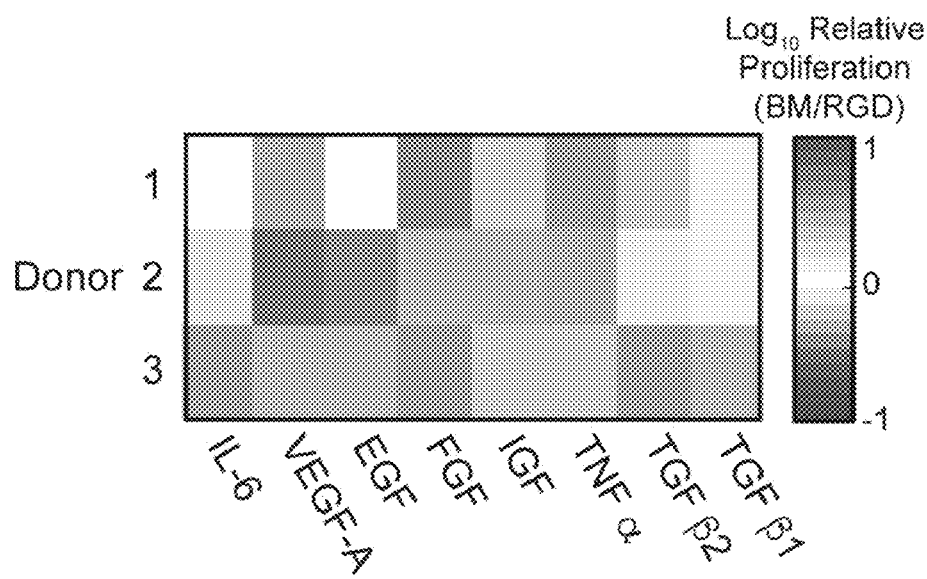
Figure 5H:
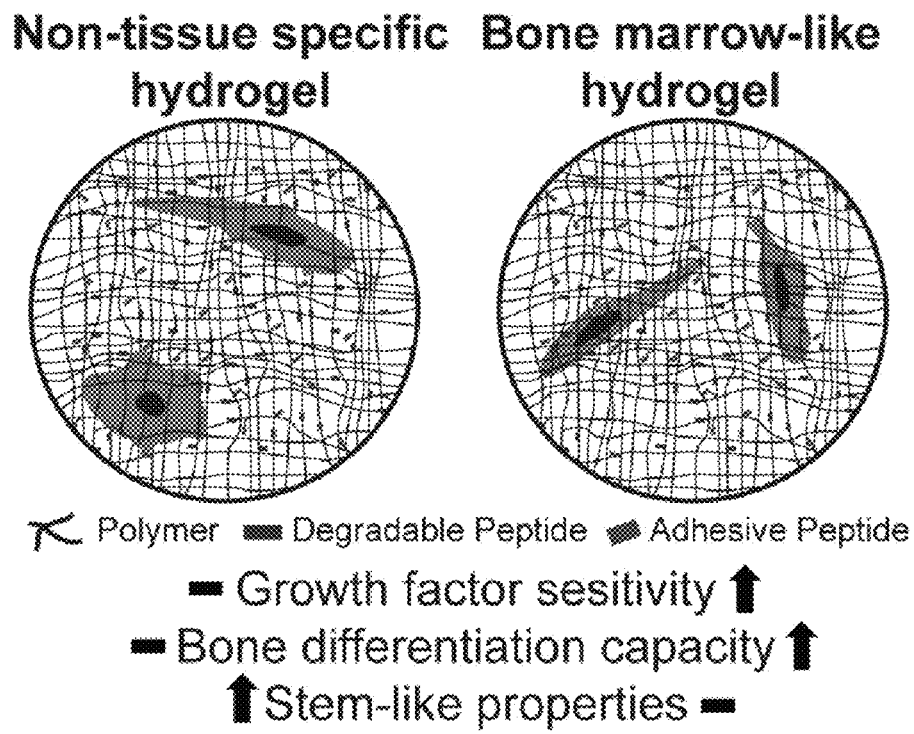
Figure 17A:
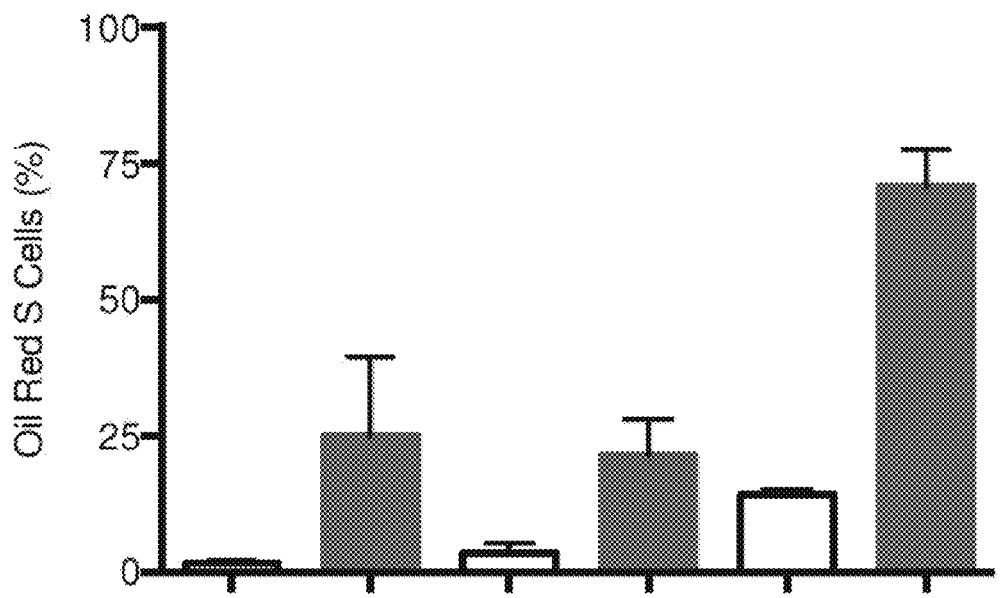
FIGS. 17A-17B. hMSC differentiate as reported in previous literature. 17A) Fat differentiation quantified by Oil Red S and 17B) bone differentiation quantified by OsteoImage across different biomaterials: tissue culture polystyrene (TCPS) and a glass coverslip (glass) or 2D hydrogel at 4 kPa with the bone marrow peptides coupled to the surface. All platforms cells were exposed to fat, bone, or stem cell medium for 21 days before analysis. Error bars represent SEM (N=3, n=2).
Figure 17B:
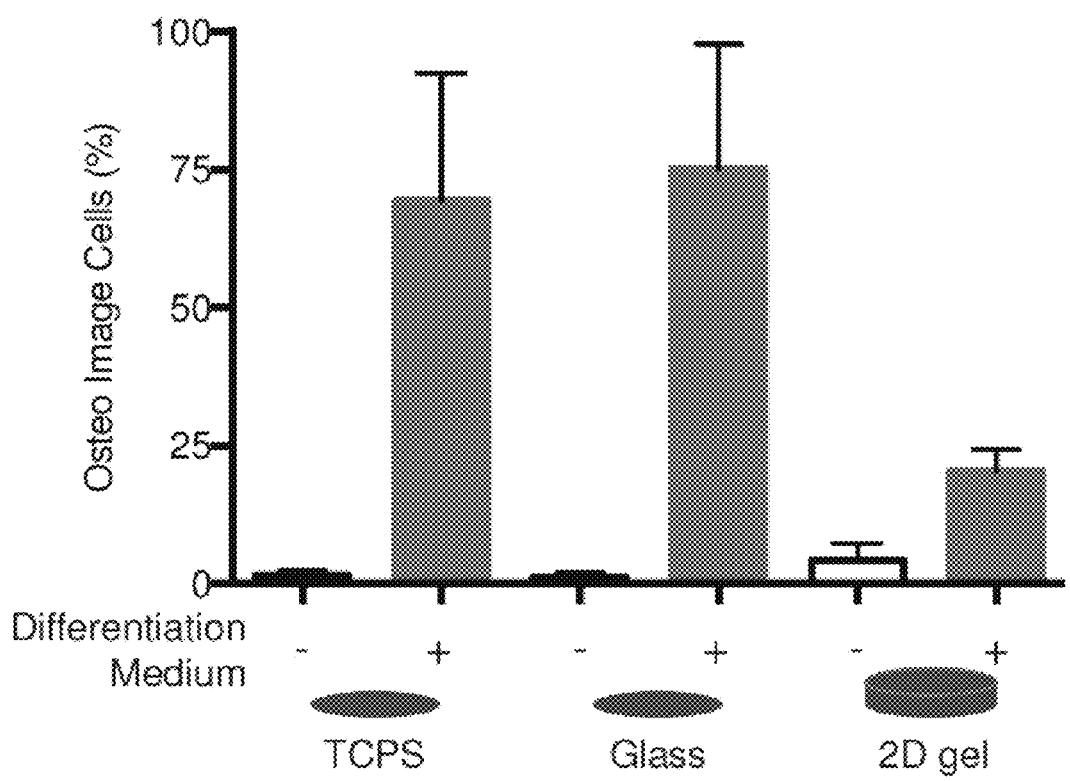
Figure 18A:
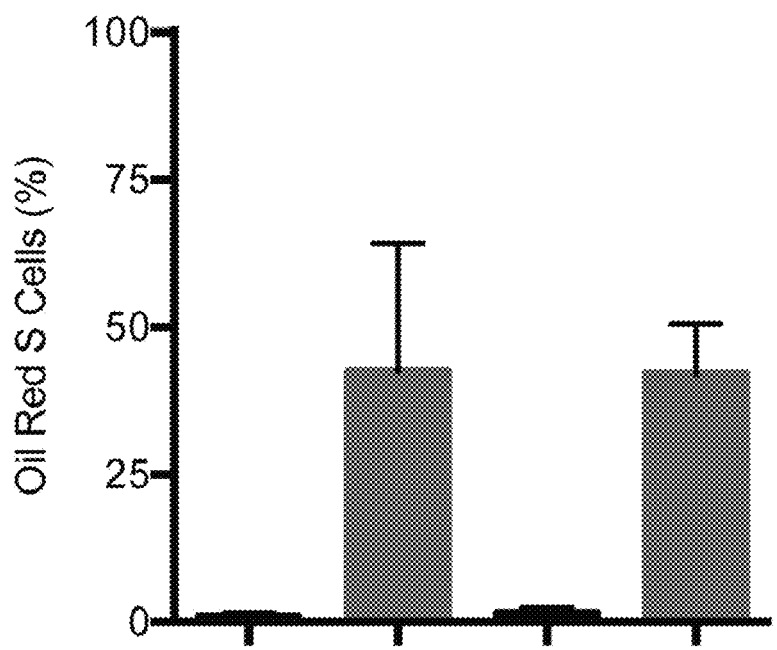
FIGS. 18A-18D. hMSC differentiation in 3D hydrogels. 18A) Fat differentiation quantified by Oil Red S and 18B) bone differentiation quantified by OsteoImage in a hydrogel with no degradability and 2 mM RGD (RGD) or the bone marrow hydrogel (BM). Representative images for hMSCs stained with 18C) Oil Red S for lipids or 18D) OsteoImage for hydroxyapatite in both 3D platforms, scale 50 μm (N=3, n=2).
Figure 18B:
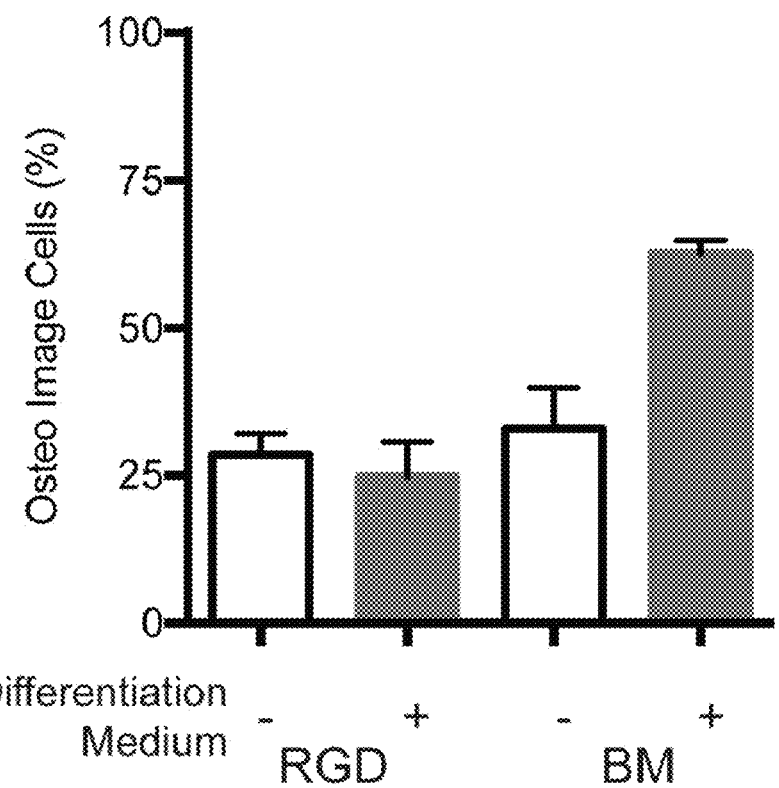
Figure 18C:
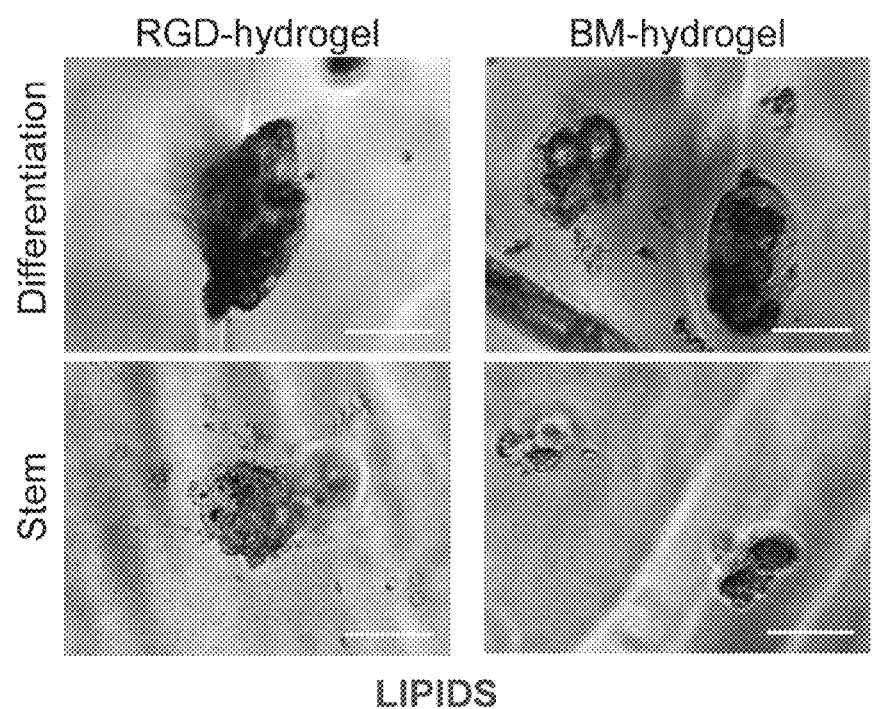
Figure 18D:
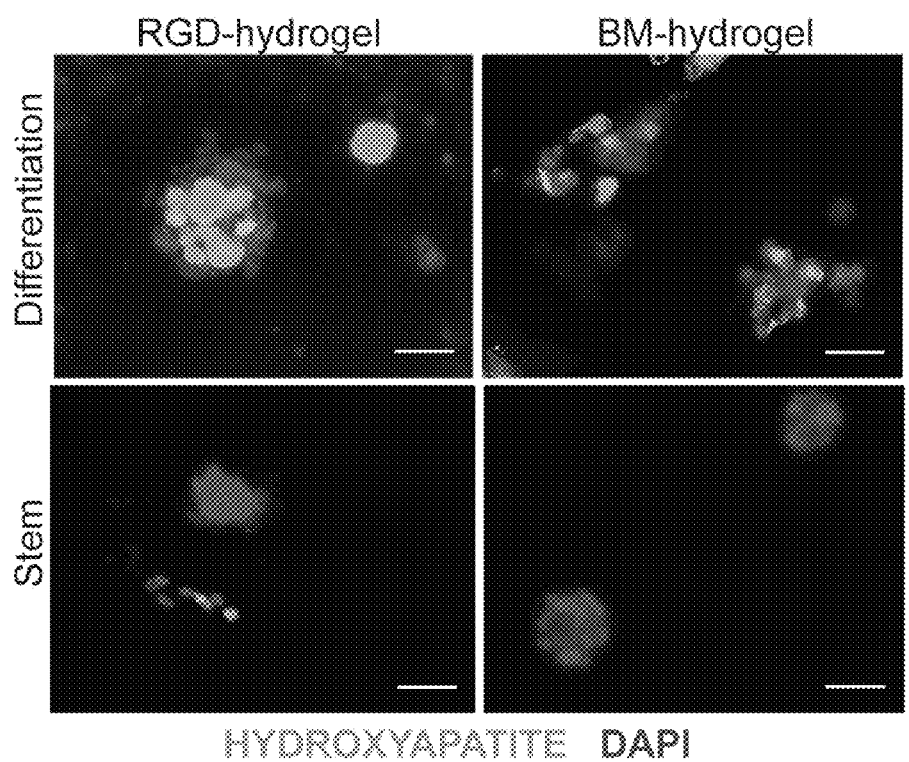

Mesenchymal Stem Cells have the Highest Differentiation Capacity in the Bone Marrow Hydrogel The results demonstrate an approach to identifying and validating matrix stiffness, cell-binding peptides, and matrix-degradable peptides for bone marrow tissue. As a final validation for this approach, the bone marrow-specific hydrogel was compared to the more commonly used RGD-functionalized PEG hydrogel and tissue culture plastic (TC). After one week of culture in the bone marrow Ki67 staining indicated these cells were slightly less proliferative in the RGD hydrogel (FIG. 5A). Heightened p21 was observed, indicating cell arrest, in the bone marrow hydrogel, but and β-galactosidase staining showed this was not because of increased cellular senescence (FIGS. 5B-5C). Finally, α-smooth muscle actin was highest in the bone marrow hydrogel, which suggests reduced clonogenicity and fat differentiation (FIG. 5D) (Talele et al., 2015). This suggests that hMSCs might be differentiating into either bone and/or fat cells spontaneously in response to the mimic. hMSCs were capable of differentiating into bone by staining for hydroxyapatite and fat by staining for lipids. hMSCs differentiate in a stiffness-dependent manner (FIG. 17) (Engler et al., 2006; Rape et al., 2015). In the 3D hydrogels hMSC differentiation capacity was measured by quantifying the ability for cells to differentiate in the presence or absence of differentiation medium. Only in the bone marrow gel did cells differentiate into bone when exposed to differentiation medium (FIG. 6E). In both gels spontaneous bone differentiation was observed, and there was no significant difference in fat differentiation between the hydrogels (FIG. 5E; FIG. 18). This suggested that the bone marrow hydrogel environment is providing a niche for hMSCs to differentiation and response to various soluble cues. In fact, hMSCs were generally more responsive to a panel of soluble proteins when encapsulated in the bone marrow gel over the RGD hydrogel (FIG. 5G). This could be because the bone marrow microenvironment supports sensitivity to soluble proteins to help traffic stromal cells from the marrow to different areas in bodies (Cornelissen et al., 2015).

Both stiffness and amount of protein play a role in stem cell differentiation, and here it was shown that the types of proteins and binding cites is also important. Although there may be materials that are better suited for the mass production of either bone and/or fat cells, because of its high tunability, the bone marrow hydrogel described herein is suited for probing underlying mechanisms as to why these cells differentiate, or not, in response to the extracellular environment and soluble cues. Heighten soluble protein sensitivity was observed as well as an increase in the number of cells differentiating into bone when provided with the appropriate signals in this environment. This shows a unique biological response that is only seen by combining both the physical and chemical properties of real bone marrow tissue.

In summary, this is apparently the first attempt to top-down engineer a material using tissue proteomic data and mechanical testing. Many make engineered tissue by functionalizing 1-2 proteins from that tissue into a material and using bone-marrow cells (Herron et al., 2016; Bersini et al., 2014). While not all biological studies require a complicated tissue-specific system, current models greatly underrepresent the chemical diversity seen in native tissue. The only other materials that are capable of tissue protein complexity employ decellularization techniques and are not batch controlled, potentially leading to inconsistent cell phenotypes (Marinkovic et al., 2016; Villasante et al., 2014). The hematopoietic environment is very cell rich, and that cellular diversity is greatly underrepresented in this model compared to others (Torisawa et al., 2014). Overall, an approach to synthetically capture tissue-specific properties was shown and the described bone marrow hydrogel can be used to elucidate tissue-specific mechanisms in cells that other systems miss.

REFERENCES

Baker, B. M. & Chen, C. S. Deconstructing the third dimension: how 3D culture microenvironments alter cellular cues. J. Cell Sci. 125, 3015-24 (2012).

Baker, B. M. et al. Cell-mediated fibre recruitment drives extracellular matrix mechanosensing in engineered fibrillar microenvironments. Nat. Mater. (2015). doi:10.1038/nmat4444

Barney, L. E. et al. The predictive link between matrix and metastasis. Curr. Opin. Chem. Eng. 11, 85-93

Berre, L. et al. Confinement and Low Adhesion Induce Fast Amoeboid Migration of Slow Mesenchymal Cells Graphical Abstract Article Confinement and Low Adhesion Induce Fast Amoeboid Migration of Slow Mesenchymal Cells. Cell 160, 659-672 (2015).

Bersini, S. et al. A Microfluidic 3D In Vitro Model for Specificity of Breast Cancer Metastasis to Bone Access. Biomaterials 36, 2454-2461 (2014).

Calvo. F. et al. Mechanotransduction and YAP-dependent matrix remodelling is required for the generation and maintenance of cancer-associated fibroblasts. Nat. Cell Biol. 15, 637-46 (2013).

Chaudhuri, O. et al. Hydrogels with tunable stress relaxation regulate stem cell fate and activity. Nat. Mater. advance on. (2015).

Choi. J. S. & Harley, B. A. Challenges and Opportunities to Harnessing the (Hematopoietic) Stem Cell Niche. Curr Stem Cell Rep 2, 85-94 (2016).

Choi, J. S. & Harley, B. Marrow-inspired matrix cues rapidly affect early fate decisions of hematopoietic stem and progenitor cells. (2017).

Cornelissen, A. S., Maijenburg, M. W. & Voermans, M. A. N. E. C. Organ-specific migration of mesenchymal stromal cells: Who, when, where and why?Immunol. Lett. (2015). doi:10.1016/j.imlet.2015.06.019

Engler, A. J., Sen, S., Sweeney, H. L. & Discher, D. E. Matrix elasticity directs stem cell lineage specification. Cell 126, 677-89 (2006).

Gilbert, P. et al. Substrate elasticity regulates skeletal muscle stem cell self-renewal in culture. Science (80-.), 329, 1078-1081 (2010).

Gjorevski, N. et al. Designer matrices for intestinal stem cell and organoid culture. Nat. Publ. Gr. 539, 560-564 (2016).

Herrick, W. G. et al. Smooth Muscle Stiffness Sensitivity is Driven by Soluble and Insoluble ECM Chemistry. Cell. Mol. Bioeng. (2015). doi:10.1007/s12195-015-0397-4

Herroon, M. K., Diedrich, J. D. & Podgorski, I. New 3D-culture approaches to study interactions of bone marrow adipocytes with metastatic prostate cancer cells. Front. Endocrinol. (Lausanne), 7, (2016).

Holzapfel, B. M. et al. Tissue engineered humanized bone supports human hematopoiesis in vivo. Biomaterials 61, 103-114 (2015).

Jansen, L. E., Birch, N. P., Schiffman. J. D., Crosby. A. J. & Peyton, S. R. Mechanics of intact bone marrow. J. Mech. Behav. Biomed. Mater. 50, 299-307 (2015).

Kloxin, A. M., Kloxin, C. J., Bowman, C. N. & Anseth, K. S. Mechanical properties of cellularly responsive hydrogels and their experimental determination. Adv. Mater. 22, 3484-94 (2010).

Lee, J. et al. Implantable microenvironments to attract hematopoietic stem/cancer cells. Proc. Natl. Acad. Sci. 109, 19638-19643 (2012).

Levental, K. R. et al. Matrix Crosslinking Forces Tumor Progression by Enhancing Integrin Signaling. Cell 139, 891-906 (2009).

Löffek, S., Schilling, O. & Franzke, C. W. Biological role of matrix metalloproteinases: A critical balance. Eur. Respir. J. 38, 191-208 (2011).

Marinkovic, M. et al. One size does not fit all: developing a cell-specific niche for in vitro study of cell behavior. Matrix Biol. 1-16 (2016). doi:10.1016/j.matbio.2016.01.004

Naba, a. et al. The Matrisome: In Silico Definition and In Vivo Characterization by Proteomics of Normal and Tumor Extracellular Matrices. Mol. Cell. Proteomics 11, M111.014647-M 111.014647 (2012).

Nguyen, T. V., Sleiman, M., Moriarty. T., Herrick, W. G. & Peyton, S. R. Sorafenib resistance and JNK signaling in carcinoma during extracellular matrix stiffening. Biomaterials 35, 5749-5759 (2014).

Nichols, J. E. et al. In vitro analog of human bone marrow from 3D scaffolds with biomimetic inverted colloidal crystal geometry. Biomaterials 30, 1071-1079 (2010).

Patterson, J. & Hubbell, J. a. Enhanced proteolytic degradation of molecularly engineered PEG hydrogels in response to MMP-1 and MMP-2. Biomaterials 31, 7836-45 (2010).

Peyton, S. R. et al. Marrow-derived stem cell motility in 3D synthetic scaffold is governed by geometry along with adhesivity and stiffness. Biotechnol. Bioeng. 108, 1181-93 (2011).

Phelps, E. a et al. Maleimide Cross-Linked Bioactive PEG Hydrogel Exhibits Improved Reaction Kinetics and Cross-Linking for Cell Encapsulation and In Situ Delivery. Adv. Mater. 24, 64-+(2012).

Ranga, A. et al. 3D niche microarrays for systems-level analyses of cell fate. Nat. Commun. 5, 4324 (2014).

Rape, A. D., Zibinsky. M., Murthy. N. & Kumar, S. A synthetic hydrogel for the high-throughput study of cell-ECM interactions. Nat. Commun. 6, 8129 (2015).

Talele, N. P., Fradette, J., Davies, J. E., Kapus, A. & Hinz, B. Expression of alpha-Smooth Muscle Actin Determines the Fate of Mesenchymal Stromal Cells. Stem Cell Reports 4, 1016-1030 (2015).

Tibbitt, M. W. & Anseth, K. S. Hydrogels as extracellular matrix mimics for 3D cell culture. Biotechnol. Bioeng. 103, 655-63 (2009).

Torisawa, Y.-S. et al. Bone marrow-on-a-chip replicates hematopoietic niche physiology in vitro. Nat. Methods 11, 663-9 (2014).

Uhlén, M. et al. Tissue-based map of the human proteome. 347, (2015).

Van Vlierberghe, S., Dubruel, P. & Schacht, E. Biopolymer-Based Hydrogels As Scaffolds for Tissue Engineering Applications: A Review. Biomacromolecules 12, 1387-1408 (2011).

Villasante, A., Marturano-Kruik, A. & Vunjak-Novakovic, G. Bioengineered human tumor within a bone niche. Biomaterials 35, 5785-94 (2014).

Wen, J. H. et al. Interplay of matrix stiffness and protein tethering in stem cell differentiation. Nat. Mater. advance on, 1-21 (2014).

Yang, C., Tibbitt, M. W., Basta. L. & Anseth, K. S. Mechanical memory and dosing influence stem cell fate. Nat. Mater. 13, 645-52 (2014).

Zaman, M. H. et al. Migration of tumor cells in 3D matrices is governed by matrix stiffness along with cell-matrix adhesion and proteolysis. Proc. Natl. Acad. Sci. U.S.A. 103, 15-16 (2006).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A hydrogel comprising a polymer matrix comprising a plurality of peptides, wherein one of the peptides comprises VTCG (SEQ ID NO:26) and another peptide comprises LRE and the hydrogel optionally includes peptides from two or more of entactin/nidogen; vitronectin; vWF; netrin 1; fibronectin; collagen 1; fibrinogen alpha; osteopontin; fibrinogen gamma; thrombospondin; collagen IX; tenascin C; laminin-alpha; laminin-beta; laminin gamma; MMP-1, MMP-14, MMP-2, MMP-3, MMP-7, MMP-9, or MMP-13, wherein the peptide comprising LRE in the hydrogel is about 1% to about 2% and the peptide comprising VTCG (SEQ ID NO:26) is about 4% to about 6%.

2. The hydrogel of claim 1 wherein the peptides further include one or more of peptides comprising RGD, YIGSR (SEQ ID NO: 22), IKVAV (SEQ ID NO: 23), AEIDGIEL (SEQ ID NO: 24), DGEA (SEQ ID NO: 25), YSMKKTTM-KIIPFNRLTIG (SEQ ID NO: 27), SVVYLR (SEQ ID NO: 28), GPR, GFXaaGER (SEQ ID NO: 74), PHSRN(G)6RGD (SEQ ID NO: 73), or QWRDTWARRL-RICFQQREKKGKCRKA (SEQ ID NO: 31).

3. The hydrogel of claim 2, wherein the peptide comprising RGD is about 25% to about 35%, comprising YIGSR (SEQ ID NO: 22) is about 1% to about 3%, comprising IKVAV (SEQ ID NO: 23) is about 2% to about 4%, comprising AEIDGIEL (SEQ ID NO: 24) is about 2% to about 4%, comprising DGEA (SEQ ID NO: 25) is about 2% to about 4%, the YSMKKTTMKIIPFNRLTIG (SEQ ID NO: 27) is about 4% to about 6%, comprising SVVYLR (SEQ ID NO: 28) is about 7% to about 9%, comprising GPR is about 7% to about 9%, comprising GFXaaGER (SEQ ID NO: 74) is about 7% to about 9%, comprising PHSRN(G)6RGD is about 10% to about 12%, or comprising QWRDTWARRL-RICFQQREKKGKCRKA (SEQ ID NO: 31) is about 10% to about 12%.

4. The hydrogel of claim 1 wherein the peptides further include one or more peptides comprising VPMSMRGG (SEQ ID NO: 32), SGESPAYYTA (SEQ ID NO: 33), RPFSMIMG (SEQ ID NO: 34), VPLSLTMG (SEQ ID NO: 35), VPLSLYSG (SEQ ID NO: 36), GPLGLWAR (SEQ ID NO: 37), or IPESLRAG (SEQ ID NO: 38).

5. A hydrogel comprising a polymer matrix comprising a plurality of peptides, wherein the peptides comprise VTCG (SEQ ID NO:26) and LRE and one or more of VPMSMRGG (SEQ ID NO: 32), SGESPAYYTA (SEQ ID NO: 33), RPFSMIMG (SEQ ID NO: 34), VPLSLTMG (SEQ ID NO: 35), VPLSLYSG (SEQ ID NO: 36), GPLGLWAR (SEQ ID NO: 37), or IPESLRAG (SEQ ID NO: 38), wherein the VPMSMRGG (SEQ ID NO: 32) is about 15% to about 20%, SGESPAYYTA (SEQ ID NO: 33) is about 15% to about 25%, RPFSMIMG (SEQ ID NO: 34) is about 15% to about 25%, VPLSLTMG (SEQ ID NO: 35) is about 10% to about 20%, VPLSLYSG (SEQ ID NO: 36) is about 5% to about 15%, GPLGLWAR (SEQ ID NO: 37) is about 7% to about 13%, or IPESLRAG (SEQ ID NO: 38) is about 7% to about 13%.

6. The hydrogel of claim 1, wherein the polymer matrix comprises PEG, agarose, collagen, fibrin, silk, or methylcellulose.

7. The hydrogel of claim 1 wherein the polymer matrix is cross-linked.

8. The hydrogel of claim 1 which has peptides from laminin A/C, laminin β1, laminin γ, fibrinogen α, fibrinogen β, fibrinogen γ, thrombospondin-1, vitronectin, fibronectin, collagen α1, collagen 1, collagen αI, collagen II, collagen III, collagen IV, collagen α21, collagen I, collagen V, collagen IV, vWf, fibrinogen α, fibrinogen β, fibrinogen γ, vitronectin, and/or fibronectin, tenascin R, or Galectin 1.

9. The hydrogel of claim 1 which has peptides from collagen αI, collagen II, collagen III, collagen IV, collagen α21, collagen I, collagen V, collagen IV, vWf, fibrinogen α, fibrinogen β, fibrinogen γ, vitronectin, and/or fibronectin, tenascin R, or Galectin 1.

10. The hydrogel of claim 1 wherein the peptides in the hydrogel further include one or more of IPVSLRSGDRCG (SEQ ID NO:52), RPFSMIMG (SEQ ID NO:34), VPLSLTMG (SEQ ID NO: 35), VPLSLYSG (SEQ ID NO:36), IPESLRAG (SEQ ID NO:38), DGEA (SEQ ID NO:25), IKVAV (SEQ ID NO:23), YIGSR (SEQ ID NO:22), PHSRN-RGD (SEQ ID NO:30), GPR or RGD.

* * * * *